(12) United States Patent
Springer et al.

(10) Patent No.: US 11,136,383 B2
(45) Date of Patent: Oct. 5, 2021

(54) METHODS AND COMPOSITIONS FOR MODULATON OF TRANSFORMING GROWTH FACTOR BETA-REGULATED FUNCTIONS

(71) Applicant: THE CHILDREN'S MEDICAL CENTER CORPORATION, Boston, MA (US)

(72) Inventors: Timothy Alan Springer, Chestnut Hill, MA (US); Chafen Lu, Chestnut Hill, MA (US); Yan Qin, Andover, MA (US); Aiping Jiang, Brookline, MA (US)

(73) Assignee: THE CHILDREN'S MEDICAL CENTER CORPORATION, Boston, MA (US)

(*) Notice: Subject to any disclaimer, the term of this patent is extended or adjusted under 35 U.S.C. 154(b) by 31 days.

(21) Appl. No.: 16/344,311

(22) PCT Filed: Oct. 25, 2017

(86) PCT No.: PCT/US2017/058318
§ 371 (c)(1),
(2) Date: Apr. 23, 2019

(87) PCT Pub. No.: WO2018/081287
PCT Pub. Date: May 3, 2018

(65) Prior Publication Data
US 2019/0270798 A1 Sep. 5, 2019

Related U.S. Application Data

(60) Provisional application No. 62/413,221, filed on Oct. 26, 2016.

(51) Int. Cl.
| | |
|---|---|
| *A61K 39/395* | (2006.01) |
| *C07K 16/28* | (2006.01) |
| *C07K 16/22* | (2006.01) |
| *A61P 35/00* | (2006.01) |
| *A61K 39/00* | (2006.01) |

(52) U.S. Cl.
CPC .......... *C07K 16/22* (2013.01); *A61K 39/3955* (2013.01); *A61P 35/00* (2018.01); *C07K 16/28* (2013.01); *C07K 16/2818* (2013.01); *C07K 16/2863* (2013.01); *A61K 2039/507* (2013.01); *C07K 2317/20* (2013.01); *C07K 2317/33* (2013.01)

(58) Field of Classification Search
CPC ....... A61K 39/395; C07K 16/22; C07K 16/28
See application file for complete search history.

(56) References Cited

U.S. PATENT DOCUMENTS

| | | | |
|---|---|---|---|
| 2014/0099254 A1* | 4/2014 | Chang | C07K 16/30 424/1.11 |
| 2015/0337034 A1 | 11/2015 | Schurpf et al. | |
| 2016/0051672 A1 | 2/2016 | Stewart et al. | |

FOREIGN PATENT DOCUMENTS

| | | | | |
|---|---|---|---|---|
| WO | 2014182676 A2 | 11/2014 | | |
| WO | WO-2014182676 A2 * | 11/2014 | ............. | C07K 16/22 |
| WO | 2016115345 A1 | 7/2016 | | |

OTHER PUBLICATIONS

Knappik et al., J. Mol. Biol., 2000, vol. 296(1):57-86.*
Nair et al., 2002, J. Immunol., vol. 168(5):2371-2382.*
Lu et al., J. Immunol., 2004, vol. 173(6):3972-3978.*
Rabia et al., Biochem. Eng. J., 2018, vol. 137:365-374.*
Su et al., "Epigenetically modulated LRRC33 acts as a negative physiological regulator for multiple Toll-like receptors." Journal of Leukocyte Biology 96(1):17-26 (2014).

* cited by examiner

*Primary Examiner* — Xiaozhen Xie
(74) *Attorney, Agent, or Firm* — Nixon Peabody LLP; David S. Resnick; Mark J. FitzGerald

(57) ABSTRACT

Disclosed are compositions and methods for modulating the activity of TGF-β. More particularly, compositions and methods for modulating the release of active TGF-β from an LRRC33-TGF-β prodomain-TGF-β ternary complex are provided, as are and methods of treatment based upon such modulation.

10 Claims, 28 Drawing Sheets
Specification includes a Sequence Listing.

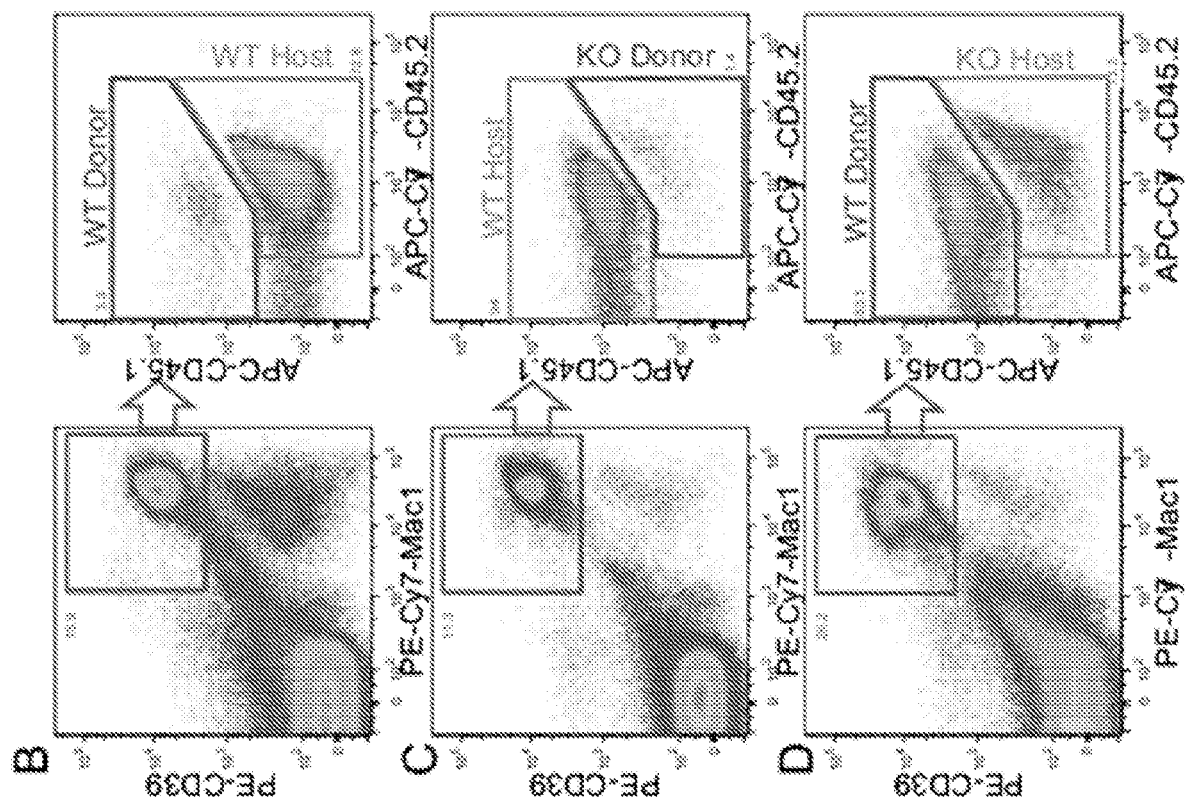
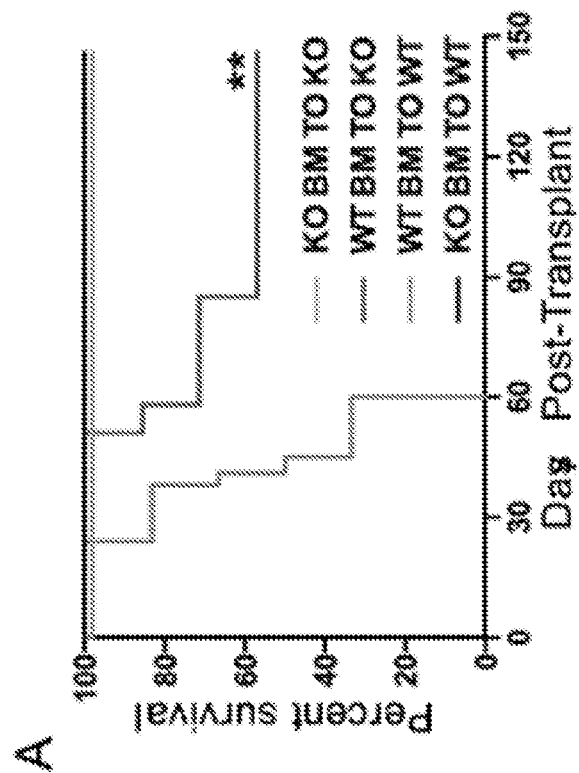
FIGs. 5A-5D

SEQUENCE LISTING

<160> NUMBER OF SEQ ID NOS: 18

<210> SEQ ID NO 1
<211> LENGTH: 692
<212> TYPE: PRT
<213> ORGANISM: Homo sapiens

<400> SEQUENCE: 1

```
Met Glu Leu Leu Pro Leu Trp Leu Cys Leu Gly Phe His Phe Leu Thr
1               5                   10                  15

Val Gly Trp Arg Asn Arg Ser Gly Thr Ala Thr Ala Ala Ser Gln Gly
            20                  25                  30

Val Cys Lys Leu Val Gly Gly Ala Ala Asp Cys Arg Gly Gln Ser Leu
        35                  40                  45

Ala Ser Val Pro Ser Ser Leu Pro Pro His Ala Arg Met Leu Thr Leu
    50                  55                  60

Asp Ala Asn Pro Leu Lys Thr Leu Trp Asn His Ser Leu Gln Pro Tyr
65                  70                  75                  80

Pro Leu Leu Glu Ser Leu Ser Leu His His Cys His Leu Glu Arg Ile
                85                  90                  95

Ser Arg Gly Ala Phe Gln Glu Gln Gly His Leu Arg Ser Leu Val Leu
            100                 105                 110

Gly Asp Asn Cys Leu Ser Glu Asn Tyr Glu Glu Thr Ala Ala Ala Leu
        115                 120                 125

His Ala Leu Pro Gly Leu Arg Arg Leu Asp Leu Ser Gly Asn Ala Leu
    130                 135                 140

Thr Glu Asp Met Ala Ala Leu Met Leu Gln Asn Leu Ser Ser Leu Arg
145                 150                 155                 160

Ser Val Ser Leu Ala Gly Asn Thr Ile Met Arg Leu Asp Asp Ser Val
                165                 170                 175
```

-continued

```
Phe Glu Gly Leu Glu Arg Leu Arg Glu Leu Asp Leu Gln Arg Asn Tyr
                180                 185                 190
Ile Phe Glu Ile Glu Gly Gly Ala Phe Asp Gly Leu Ala Glu Leu Arg
                195                 200                 205
His Leu Asn Leu Ala Phe Asn Asn Leu Pro Cys Ile Val Asp Phe Gly
            210                 215                 220
Leu Thr Arg Leu Arg Val Leu Asn Val Ser Tyr Asn Val Leu Glu Trp
225                 230                 235                 240
Phe Leu Ala Thr Gly Gly Glu Ala Ala Phe Glu Leu Glu Thr Leu Asp
                245                 250                 255
Leu Ser His Asn Gln Leu Leu Phe Phe Pro Leu Leu Pro Gln Tyr Ser
            260                 265                 270
Lys Leu Arg Thr Leu Leu Leu Arg Asp Asn Asn Met Gly Phe Tyr Arg
            275                 280                 285
Asp Leu Tyr Asn Thr Ser Ser Pro Arg Glu Met Val Ala Gln Phe Leu
            290                 295                 300
Leu Val Asp Gly Asn Val Thr Asn Ile Thr Thr Val Ser Leu Trp Glu
305                 310                 315                 320
Glu Phe Ser Ser Ser Asp Leu Ala Asp Leu Arg Phe Leu Asp Met Ser
                325                 330                 335
Gln Asn Gln Phe Gln Tyr Leu Pro Asp Gly Phe Leu Arg Lys Met Pro
            340                 345                 350
Ser Leu Ser His Leu Asn Leu His Gln Asn Cys Leu Met Thr Leu His
            355                 360                 365
Ile Arg Glu His Glu Pro Pro Gly Ala Leu Thr Glu Leu Asp Leu Ser
            370                 375                 380
His Asn Gln Leu Ser Glu Leu His Leu Ala Pro Gly Leu Ala Ser Cys
385                 390                 395                 400
Leu Gly Ser Leu Arg Leu Phe Asn Leu Ser Ser Asn Gln Leu Leu Gly
                405                 410                 415
Val Pro Pro Gly Leu Phe Ala Asn Ala Arg Asn Ile Thr Thr Leu Asp
            420                 425                 430
Met Ser His Asn Gln Ile Ser Leu Cys Pro Leu Pro Ala Ala Ser Asp
            435                 440                 445
Arg Val Gly Pro Pro Ser Cys Val Asp Phe Arg Asn Met Ala Ser Leu
450                 455                 460
Arg Ser Leu Ser Leu Glu Gly Cys Gly Leu Gly Ala Leu Pro Asp Cys
465                 470                 475                 480
Pro Phe Gln Gly Thr Ser Leu Thr Tyr Leu Asp Leu Ser Ser Asn Trp
                485                 490                 495
Gly Val Leu Asn Gly Ser Leu Ala Pro Leu Gln Asp Val Ala Pro Met
            500                 505                 510
Leu Gln Val Leu Ser Leu Arg Asn Met Gly Leu His Ser Ser Phe Met
            515                 520                 525
Ala Leu Asp Phe Ser Gly Phe Gly Asn Leu Arg Asp Leu Asp Leu Ser
            530                 535                 540
Gly Asn Cys Leu Thr Thr Phe Pro Arg Phe Gly Gly Ser Leu Ala Leu
545                 550                 555                 560
Glu Thr Leu Asp Leu Arg Arg Asn Ser Leu Thr Ala Leu Pro Gln Lys
                565                 570                 575
Ala Val Ser Glu Gln Leu Ser Arg Gly Leu Arg Thr Ile Tyr Leu Ser
            580                 585                 590
Gln Asn Pro Tyr Asp Cys Cys Gly Val Asp Gly Trp Gly Ala Leu Gln
```

```
                595                 600                 605
His Gly Gln Thr Val Ala Asp Trp Ala Met Val Thr Cys Asn Leu Ser
    610                 615                 620

Ser Lys Ile Ile Arg Val Thr Glu Leu Pro Gly Gly Val Pro Arg Asp
625                 630                 635                 640

Cys Lys Trp Glu Arg Leu Asp Leu Gly Leu Leu Tyr Leu Val Leu Ile
                645                 650                 655

Leu Pro Ser Cys Leu Thr Leu Val Ala Cys Thr Val Ile Val Leu
            660                 665                 670

Thr Phe Lys Lys Pro Leu Leu Gln Val Ile Lys Ser Arg Cys His Trp
    675                 680                 685

Ser Ser Val Tyr
    690

<210> SEQ ID NO 2
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Phe Gln Leu Gln Gln Ser Gly Pro Glu Leu Val Lys Pro Gly Ala
1               5                   10                  15

Ser Val Lys Met Ser Cys Lys Ala Ser Gly Tyr Ser Phe Thr Asp Ser
            20                  25                  30

Tyr Met Asp Trp Val Lys Gln Ser Asn Gly Lys Thr Leu Glu Trp Ile
        35                  40                  45

Gly Leu Ile Asn Pro Lys Tyr Gly Thr Thr Tyr Asn Gln Lys Phe
    50                  55                  60

Lys Gly Lys Ala Thr Leu Thr Val Asp Gln Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Ser Leu Tyr Tyr Asp Tyr Ser Ala Trp Phe Ala Tyr Trp Gly Gln
            100                 105                 110

Gly Thr Leu Val Thr Val Ser Ala
        115                 120

<210> SEQ ID NO 3
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Ile Ile Thr Gly Ala
```

```
                65                  70                  75                  80
Gln Thr Glu Asp Glu Ala Ile Tyr Phe Cys Gly Leu Trp Phe Ser Asn
                    85                  90                  95

Arg Trp Val Phe Gly Gly Gly Thr Lys Leu Thr Val Val
                100                 105

<210> SEQ ID NO 4
<211> LENGTH: 390
<212> TYPE: PRT
<213> ORGANISM: Homo sapiens

<400> SEQUENCE: 4

Met Pro Pro Ser Gly Leu Arg Leu Leu Leu Leu Leu Pro Leu Leu
1               5                   10                  15

Trp Leu Leu Val Leu Thr Pro Gly Arg Pro Ala Ala Gly Leu Ser Thr
                20                  25                  30

Cys Lys Thr Ile Asp Met Glu Leu Val Lys Arg Lys Arg Ile Glu Ala
                35                  40                  45

Ile Arg Gly Gln Ile Leu Ser Lys Leu Arg Leu Ala Ser Pro Pro Ser
        50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
                100                 105                 110

Met Val Glu Thr His Asn Glu Ile Tyr Asp Lys Phe Lys Gln Ser Thr
                115                 120                 125

His Ser Ile Tyr Met Phe Phe Asn Thr Ser Glu Leu Arg Glu Ala Val
        130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
                180                 185                 190

Pro Glu Trp Leu Ser Phe Asp Val Thr Gly Val Val Arg Gln Trp Leu
                195                 200                 205

Ser Arg Gly Gly Glu Ile Glu Gly Phe Arg Leu Ser Ala His Cys Ser
        210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
                260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
        290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335
```

```
Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
            355                 360                 365

Tyr Val Gly Arg Lys Pro Lys Val Glu Gln Leu Ser Asn Met Ile Val
            370                 375             380

Arg Ser Cys Lys Cys Ser
385             390

<210> SEQ ID NO 5
<211> LENGTH: 414
<212> TYPE: PRT
<213> ORGANISM: Homo sapiens

<400> SEQUENCE: 5

Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
            35                  40                  45

Lys Leu Thr Ser Pro Pro Glu Asp Tyr Pro Glu Pro Glu Glu Val Pro
        50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
            100                 105                 110

Pro Ser Glu Asn Ala Ile Pro Pro Thr Phe Tyr Arg Pro Tyr Phe Arg
            115                 120                 125

Ile Val Arg Phe Asp Val Ser Ala Met Glu Lys Asn Ala Ser Asn Leu
130                 135                 140

Val Lys Ala Glu Phe Arg Val Phe Arg Leu Gln Asn Pro Lys Ala Arg
145                 150                 155                 160

Val Pro Glu Gln Arg Ile Glu Leu Tyr Gln Ile Leu Lys Ser Lys Asp
                165                 170                 175

Leu Thr Ser Pro Thr Gln Arg Tyr Ile Asp Ser Lys Val Val Lys Thr
            180                 185                 190

Arg Ala Glu Gly Glu Trp Leu Ser Phe Asp Val Thr Asp Ala Val His
            195                 200                 205

Glu Trp Leu His His Lys Asp Arg Asn Leu Gly Phe Lys Ile Ser Leu
        210                 215                 220

His Cys Pro Cys Cys Thr Phe Val Pro Ser Asn Asn Tyr Ile Ile Pro
225                 230                 235                 240

Asn Lys Ser Glu Glu Leu Glu Ala Arg Phe Ala Gly Ile Asp Gly Thr
                245                 250                 255

Ser Thr Tyr Thr Ser Gly Asp Gln Lys Thr Ile Lys Ser Thr Arg Lys
            260                 265                 270

Lys Asn Ser Gly Lys Thr Pro His Leu Leu Leu Met Leu Leu Pro Ser
            275                 280                 285

Tyr Arg Leu Glu Ser Gln Gln Thr Asn Arg Arg Lys Lys Arg Ala Leu
        290                 295                 300

Asp Ala Ala Tyr Cys Phe Arg Asn Val Gln Asp Asn Cys Cys Leu Arg
305                 310                 315                 320
```

```
Pro Leu Tyr Ile Asp Phe Lys Arg Asp Leu Gly Trp Lys Trp Ile His
            325                 330                 335

Glu Pro Lys Gly Tyr Asn Ala Asn Phe Cys Ala Gly Ala Cys Pro Tyr
            340                 345                 350

Leu Trp Ser Ser Asp Thr Gln His Ser Arg Val Leu Ser Leu Tyr Asn
            355                 360                 365

Thr Ile Asn Pro Glu Ala Ser Ala Ser Pro Cys Cys Val Ser Gln Asp
            370                 375                 380

Leu Glu Pro Leu Thr Ile Leu Tyr Tyr Ile Gly Lys Thr Pro Lys Ile
385                 390                 395                 400

Glu Gln Leu Ser Asn Met Ile Val Lys Ser Cys Lys Cys Ser
            405                 410

<210> SEQ ID NO 6
<211> LENGTH: 412
<212> TYPE: PRT
<213> ORGANISM: Homo sapiens

<400> SEQUENCE: 6

Met Lys Met His Leu Gln Arg Ala Leu Val Val Leu Ala Leu Leu Asn
1               5                   10                  15

Phe Ala Thr Val Ser Leu Ser Leu Ser Thr Cys Thr Thr Leu Asp Phe
            20                  25                  30

Gly His Ile Lys Lys Lys Arg Val Glu Ala Ile Arg Gly Gln Ile Leu
            35                  40                  45

Ser Lys Leu Arg Leu Thr Ser Pro Pro Glu Pro Thr Val Met Thr His
50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Gly Cys Thr Gln Glu Asn Thr
            85                  90                  95

Glu Ser Glu Tyr Tyr Ala Lys Glu Ile His Lys Phe Asp Met Ile Gln
            100                 105                 110

Gly Leu Ala Glu His Asn Glu Leu Ala Val Cys Pro Lys Gly Ile Thr
            115                 120                 125

Ser Lys Val Phe Arg Phe Asn Val Ser Ser Val Glu Lys Asn Arg Thr
130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
            165                 170                 175

Asp Glu His Ile Ala Lys Gln Arg Tyr Ile Gly Gly Lys Asn Leu Pro
            180                 185                 190

Thr Arg Gly Thr Ala Glu Trp Leu Ser Phe Asp Val Thr Asp Thr Val
            195                 200                 205

Arg Glu Trp Leu Leu Arg Arg Glu Ser Asn Leu Gly Leu Glu Ile Ser
            210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
            245                 250                 255

Asp Asp His Gly Arg Gly Asp Leu Gly Arg Leu Lys Lys Gln Lys Asp
            260                 265                 270

His His Asn Pro His Leu Ile Leu Met Met Ile Pro Pro His Arg Leu
```

```
                275                 280                 285
Asp Asn Pro Gly Gln Gly Gln Arg Lys Lys Arg Ala Leu Asp Thr
            290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
                325                 330                 335

Lys Gly Tyr Tyr Ala Asn Phe Cys Ser Gly Pro Cys Pro Tyr Leu Arg
            340                 345                 350

Ser Ala Asp Thr Thr His Ser Thr Val Leu Gly Leu Tyr Asn Thr Leu
                355                 360                 365

Asn Pro Glu Ala Ser Ala Ser Pro Cys Cys Val Pro Gln Asp Leu Glu
            370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
                405                 410

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaacccagga catctggaaa                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgagtgacag catcctggag                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcgcaacgca attaatgata                                               20

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Tyr Ser Phe Thr Asp Ser Tyr Met Asp
1               5                   10
```

```
<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asn Pro Lys Tyr Gly Thr
1               5

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Tyr Tyr Asp Tyr Ser Ala Trp Phe Ala Tyr
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ser Ser Thr Gly Ala Val Thr Thr Ser Asn Tyr Ala Asn
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Thr Asn Asn Arg Ala Pro
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Leu Trp Phe Ser Asn Arg Trp Val
1               5

<210> SEQ ID NO 16
<211> LENGTH: 674
<212> TYPE: PRT
<213> ORGANISM: Homo sapiens

<400> SEQUENCE: 16

Trp Arg Asn Arg Ser Gly Thr Ala Thr Ala Ala Ser Gln Gly Val Cys
```

```
1               5                   10                  15
Lys Leu Val Gly Gly Ala Ala Asp Cys Arg Gly Gln Ser Leu Ala Ser
            20                  25                  30

Val Pro Ser Ser Leu Pro Pro His Ala Arg Met Leu Thr Leu Asp Ala
            35                  40                  45

Asn Pro Leu Lys Thr Leu Trp Asn His Ser Leu Gln Pro Tyr Pro Leu
    50                  55                  60

Leu Glu Ser Leu Ser Leu His Ser Cys His Leu Glu Arg Ile Ser Arg
65                  70                  75                  80

Gly Ala Phe Gln Glu Gln Gly His Leu Arg Ser Leu Val Leu Gly Asp
                85                  90                  95

Asn Cys Leu Ser Glu Asn Tyr Glu Glu Thr Ala Ala Ala Leu His Ala
            100                 105                 110

Leu Pro Gly Leu Arg Arg Leu Asp Leu Ser Gly Asn Ala Leu Thr Glu
            115                 120                 125

Asp Met Ala Ala Leu Met Leu Gln Asn Leu Ser Ser Leu Arg Ser Val
    130                 135                 140

Ser Leu Ala Gly Asn Thr Ile Met Arg Leu Asp Asp Ser Val Phe Glu
145                 150                 155                 160

Gly Leu Glu Arg Leu Arg Glu Leu Asp Leu Gln Arg Asn Tyr Ile Phe
                165                 170                 175

Glu Ile Glu Gly Gly Ala Phe Asp Gly Leu Ala Glu Leu Arg His Leu
            180                 185                 190

Asn Leu Ala Phe Asn Asn Leu Pro Cys Ile Val Asp Phe Gly Leu Thr
    195                 200                 205

Arg Leu Arg Val Leu Asn Val Ser Tyr Asn Val Leu Glu Trp Phe Leu
210                 215                 220

Ala Thr Gly Gly Glu Ala Ala Phe Glu Leu Glu Thr Leu Asp Leu Ser
225                 230                 235                 240

His Asn Gln Leu Leu Phe Phe Pro Leu Leu Pro Gln Tyr Ser Lys Leu
                245                 250                 255

Arg Thr Leu Leu Leu Arg Asp Asn Asn Met Gly Phe Tyr Arg Asp Leu
            260                 265                 270

Tyr Asn Thr Ser Ser Pro Arg Glu Met Val Ala Gln Phe Leu Leu Val
    275                 280                 285

Asp Gly Asn Val Thr Asn Ile Thr Thr Val Ser Leu Trp Glu Glu Phe
290                 295                 300

Ser Ser Ser Asp Leu Ala Asp Leu Arg Phe Leu Asp Met Ser Gln Asn
305                 310                 315                 320

Gln Phe Gln Tyr Leu Pro Asp Gly Phe Leu Arg Lys Met Pro Ser Leu
                325                 330                 335

Ser His Leu Asn Leu His Gln Asn Cys Leu Met Thr Leu His Ile Arg
            340                 345                 350

Glu His Glu Pro Pro Gly Ala Leu Thr Glu Leu Asp Leu Ser His Asn
    355                 360                 365

Gln Leu Ser Glu Leu His Leu Ala Pro Gly Leu Ala Ser Cys Leu Gly
370                 375                 380

Ser Leu Arg Leu Phe Asn Leu Ser Asn Gln Leu Leu Gly Val Pro
385                 390                 395                 400

Pro Gly Leu Phe Ala Asn Ala Arg Asn Ile Thr Thr Leu Asp Met Ser
                405                 410                 415

His Asn Gln Ile Ser Leu Cys Pro Leu Pro Ala Ala Ser Asp Arg Val
            420                 425                 430
```

Gly Pro Pro Ser Cys Val Asp Phe Arg Asn Met Ala Ser Leu Arg Ser
            435                 440                 445

Leu Ser Leu Glu Gly Cys Gly Leu Gly Ala Leu Pro Asp Cys Pro Phe
        450                 455                 460

Gln Gly Thr Ser Leu Thr Tyr Leu Asp Leu Ser Ser Asn Trp Gly Val
465                 470                 475                 480

Leu Asn Gly Ser Leu Ala Pro Leu Gln Asp Val Ala Pro Met Leu Gln
                485                 490                 495

Val Leu Ser Leu Arg Asn Met Gly Leu His Ser Ser Phe Met Ala Leu
            500                 505                 510

Asp Phe Ser Gly Phe Gly Asn Leu Arg Asp Leu Asp Leu Ser Gly Asn
        515                 520                 525

Cys Leu Thr Thr Phe Pro Arg Phe Gly Gly Ser Leu Ala Leu Glu Thr
    530                 535                 540

Leu Asp Leu Arg Arg Asn Ser Leu Thr Ala Leu Pro Gln Lys Ala Val
545                 550                 555                 560

Ser Glu Gln Leu Ser Arg Gly Leu Arg Thr Ile Tyr Leu Ser Gln Asn
                565                 570                 575

Pro Tyr Asp Cys Cys Gly Val Asp Gly Trp Gly Ala Leu Gln His Gly
            580                 585                 590

Gln Thr Val Ala Asp Trp Ala Met Val Thr Cys Asn Leu Ser Ser Lys
        595                 600                 605

Ile Ile Arg Val Thr Glu Leu Pro Gly Gly Val Pro Arg Asp Cys Lys
    610                 615                 620

Trp Glu Arg Leu Asp Leu Gly Leu Leu Tyr Leu Val Leu Ile Leu Pro
625                 630                 635                 640

Ser Cys Leu Thr Leu Leu Val Ala Cys Thr Val Ile Val Leu Thr Phe
                645                 650                 655

Lys Lys Pro Leu Leu Gln Val Ile Lys Ser Arg Cys His Trp Ser Ser
            660                 665                 670

Val Tyr

<210> SEQ ID NO 17
<211> LENGTH: 643
<212> TYPE: PRT
<213> ORGANISM: Homo sapiens

<400> SEQUENCE: 17

His Gln Asp Lys Val Pro Cys Lys Met Val Asp Lys Lys Val Ser Cys
1               5                   10                  15

Gln Val Leu Gly Leu Leu Gln Val Pro Ser Val Leu Pro Pro Asp Thr
            20                  25                  30

Glu Thr Leu Asp Leu Ser Gly Asn Gln Leu Arg Ser Ile Leu Ala Ser
        35                  40                  45

Pro Leu Gly Phe Tyr Thr Ala Leu Arg His Leu Asp Leu Ser Thr Asn
    50                  55                  60

Glu Ile Ser Phe Leu Gln Pro Gly Ala Phe Gln Ala Leu Thr His Leu
65                  70                  75                  80

Glu His Leu Ser Leu Ala His Asn Arg Leu Ala Met Ala Thr Ala Leu
                85                  90                  95

Ser Ala Gly Gly Leu Gly Pro Leu Pro Arg Val Thr Ser Leu Asp Leu
            100                 105                 110

Ser Gly Asn Ser Leu Tyr Ser Gly Leu Leu Glu Arg Leu Leu Gly Glu
        115                 120                 125

```
Ala Pro Ser Leu His Thr Leu Ser Leu Ala Glu Asn Ser Leu Thr Arg
            130                 135                 140

Leu Thr Arg His Thr Phe Arg Asp Met Pro Ala Leu Glu Gln Leu Asp
145                 150                 155                 160

Leu His Ser Asn Val Leu Met Asp Ile Glu Asp Gly Ala Phe Glu Gly
                165                 170                 175

Leu Pro Arg Leu Thr His Leu Asn Leu Ser Arg Asn Ser Leu Thr Cys
            180                 185                 190

Ile Ser Asp Phe Ser Leu Gln Gln Leu Arg Val Leu Asp Leu Ser Cys
        195                 200                 205

Asn Ser Ile Glu Ala Phe Gln Thr Ala Ser Gln Pro Gln Ala Glu Phe
210                 215                 220

Gln Leu Thr Trp Leu Asp Leu Arg Glu Asn Lys Leu Leu His Phe Pro
225                 230                 235                 240

Asp Leu Ala Ala Leu Pro Arg Leu Ile Tyr Leu Asn Leu Ser Asn Asn
                245                 250                 255

Leu Ile Arg Leu Pro Thr Gly Pro Pro Gln Asp Ser Lys Gly Ile His
            260                 265                 270

Ala Pro Ser Glu Gly Trp Ser Ala Leu Pro Leu Ser Ala Pro Ser Gly
        275                 280                 285

Asn Ala Ser Gly Arg Pro Leu Ser Gln Leu Leu Asn Leu Asp Leu Ser
290                 295                 300

Tyr Asn Glu Ile Glu Leu Ile Pro Asp Ser Phe Leu Glu His Leu Thr
305                 310                 315                 320

Ser Leu Cys Phe Leu Asn Leu Ser Arg Asn Cys Leu Arg Thr Phe Glu
                325                 330                 335

Ala Arg Arg Leu Gly Ser Leu Pro Cys Leu Met Leu Leu Asp Leu Ser
            340                 345                 350

His Asn Ala Leu Glu Thr Leu Glu Leu Gly Ala Arg Ala Leu Gly Ser
        355                 360                 365

Leu Arg Thr Leu Leu Leu Gln Gly Asn Ala Leu Arg Asp Leu Pro Pro
370                 375                 380

Tyr Thr Phe Ala Asn Leu Ala Ser Leu Gln Arg Leu Asn Leu Gln Gly
385                 390                 395                 400

Asn Arg Val Ser Pro Cys Gly Gly Pro Asp Glu Pro Gly Pro Ser Gly
                405                 410                 415

Cys Val Ala Phe Ser Gly Ile Thr Ser Leu Arg Ser Leu Ser Leu Val
            420                 425                 430

Asp Asn Glu Ile Glu Leu Leu Arg Ala Gly Ala Phe Leu His Thr Pro
        435                 440                 445

Leu Thr Glu Leu Asp Leu Ser Ser Asn Pro Gly Leu Glu Val Ala Thr
450                 455                 460

Gly Ala Leu Gly Gly Leu Glu Ala Ser Leu Glu Val Leu Ala Leu Gln
465                 470                 475                 480

Gly Asn Gly Leu Met Val Leu Gln Val Asp Leu Pro Cys Phe Ile Cys
                485                 490                 495

Leu Lys Arg Leu Asn Leu Ala Glu Asn Arg Leu Ser His Leu Pro Ala
            500                 505                 510

Trp Thr Gln Ala Val Ser Leu Glu Val Leu Asp Leu Arg Asn Asn Ser
        515                 520                 525

Phe Ser Leu Leu Pro Gly Ser Ala Met Gly Gly Leu Glu Thr Ser Leu
530                 535                 540
```

-continued

```
Arg Arg Leu Tyr Leu Gln Gly Asn Pro Leu Ser Cys Cys Gly Asn Gly
545                 550                 555                 560

Trp Leu Ala Ala Gln Leu His Gln Gly Arg Val Asp Val Asp Ala Thr
                565                 570                 575

Gln Asp Leu Ile Cys Arg Phe Ser Ser Gln Glu Glu Val Ser Leu Ser
            580                 585                 590

His Val Arg Pro Glu Asp Cys Glu Lys Gly Gly Leu Lys Asn Ile Asn
        595                 600                 605

Leu Ile Ile Ile Leu Thr Phe Ile Leu Val Ser Ala Ile Leu Leu Thr
    610                 615                 620

Thr Leu Ala Ala Cys Cys Cys Val Arg Arg Gln Lys Phe Asn Gln Gln
625                 630                 635                 640

Tyr Lys Ala

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

His His His His His
1               5
```

METHODS AND COMPOSITIONS FOR MODULATON OF TRANSFORMING GROWTH FACTOR BETA-REGULATED FUNCTIONS

CROSS-REFERENCE TO RELATED APPLICATIONS

This application is a 35 U.S.C. § 371 National Phase Entry Application of International Application No. PCT/US2017/058318 filed Oct. 25, 2017, which designates the U.S. and claims benefit under 35 U.S.C. § 119(e) of U.S. Provisional Application No. 62/413,221 filed Oct. 26, 2016, the contents of which are incorporated herein by reference in their entireties.

GOVERNMENT SUPPORT

This invention was made with government support under Grant No. HL103526 and AI095686 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Nov. 22, 2017, is named 701039-086931-PCT_SL.txt and is 32,688 bytes in size.

TECHNICAL FIELD

The technology disclosed herein relates to the manipulation of biological regulatory pathways and its application to the treatment or prevention of disease.

BACKGROUND

The Transforming Growth Factor β (TGF-β) family of protein factors participates in a wide array of regulatory pathways in a wide array of different cell and tissue types, and at different stages of normal and pathological processes. The TGF-β family of genes first appears in the earliest metazoans. Bilaterians including *Drosophila* possess many family members orthologous to those in mammals including activins and bone morphogenetic proteins. However, TGF-β itself does not appear until the emergence of Deuterostomes. The Arg-Gly-Asp tripeptide RGD motif in the TGF-β prodomain required for activation by integrins is present in primitive deuterostomes with only a single TGF-β gene, and thus TGF-β appears to have evolved in a context in which it was activated by integrins. TGF-β is regulated quite differently than other family members such as bone morphogenetic proteins or activins, for which a large number of antagonistic proteins evolved. Little is known about how TGF-β, despite its relatively late evolutionary emergence, was able to evolve in vertebrates such a wide range of functions, many of which appear contradictory.

SUMMARY

The technology described herein is based, in part, on the discovery that the polypeptide Leucine-Rich Repeat-Containing 33 (LRRC33) covalently binds the TGF-β prodomain (also referred to herein as "pro-TGF-β") and influences the availability of mature, active TGF-β. LRRC33 is expressed in a tightly-regulated manner, being exclusively expressed in white blood cells, particularly in macrophages, dendritic cells and B cells. In the central nervous system (CNS), its expression is restricted largely to microglia, a resident macrophage population in the CNS. It is demonstrated herein that LRRC33, via its covalent interaction with pro-TGF-β, modulates the immune activity of macrophages. The methods and compositions described herein exploit the discovery of this function of LRRC33 to manipulate TGF-β-mediated functions in microglia, other macrophages and other cells of the myeloid lineage. More specifically, the discovery that LRRC33 participates in the cell-type specific regulation of TGF-β-mediated modulation of the innate immune system provides therapeutic approaches to both increase and decrease the activity of macrophages. Modulation of macrophage activity has therapeutic application in, for example, disorders involving immuno-suppression (e.g., cancer, chronic infection, etc.) as well as in disorders involving inappropriate immune activity (e.g., autoimmune disease and fibrosis, among others). As described herein, reagents that are specific to LRRC33 and its complex with pro-TGF-β can be beneficial in the treatment of disorders involving both immunosuppression and inappropriate immune activity.

Thus in one aspect, described herein is a method of preventing release of active TGF-β from an LRRC33-TGF-β prodomain-TGF-β complex, the method comprising contacting a cell that comprises an LRRC33-TGF-β prodomain-TGF-β complex, with an agent that stabilizes the LRRC33-TGF-β prodomain-TGF-β complex, wherein the stabilizing prevents release of active TGF-β from the LRRC33-TGF-β prodomain-TGF-β complex.

In one embodiment, the agent comprises an antibody or antigen-binding fragment thereof. In another embodiment, the antibody or antigen-binding fragment thereof specifically binds an LRRC33 epitope. Such an antibody or antigen-binding fragment will not bind or cross-react with human GARP polypeptide.

In another embodiment, the antibody or antigen-binding fragment thereof specifically binds an epitope comprised only by the LRRC33-TGF-β prodomain-TGF-β complex. When used in the context of an epitope, terms such as "comprised only by the 'N complex'" mean that the epitope in question is formed only when the recited complex is formed; an antibody that recognizes such an epitope will not specifically bind either of the three components of the complex in isolation.

In another embodiment, the cell is a macrophage.

In another aspect, described herein is a method of promoting macrophage activity, the method comprising contacting a macrophage with an agent that stabilizes the interaction of an LRRC33-TGF-β prodomain complex with TGF-β. In one embodiment, the agent comprises an antibody or antigen-binding fragment thereof. In another embodiment, the antibody or antigen-binding fragment thereof specifically binds an LRRC33 epitope. In another embodiment, the antibody or antigen-binding fragment thereof specifically binds an epitope comprised only by the LRRC33-TGF-β prodomain-TGF-β complex.

In another aspect, described herein is a method of enhancing immune activity in a subject in need thereof, the method comprising, administering an agent that stabilizes the interaction of an LRRC33-TGF-β prodomain complex with TGF-β, thereby enhancing immune activity in the subject. In one embodiment, the agent comprises an antibody or antigen-binding fragment thereof. In another embodiment, the antibody or antigen-binding fragment thereof specifically binds an epitope on LRRC33. In another embodiment, the antibody or antigen-binding fragment thereof specifically binds an epitope comprised only by the LRRC33-TGF-β prodomain-TGF-β complex.

In another embodiment, the subject has cancer or a chronic infection.

In another aspect, described herein is a method of promoting cell surface clearance or endocytosis of an LRRC33-TGF-β prodomain-TGF-β complex from a cell, the method comprising contacting the cell with an agent that specifically binds LRRC33. In one embodiment, the agent comprises an antibody. In another embodiment, the antibody specifically binds LRRC33. In another embodiment, the antibody specifically binds the ectodomain of LRRC33.

In another aspect, described herein is a method of promoting cell surface clearance or endocytosis of an LRRC33-TGF-β prodomain-TGF-β complex from a cell, the method comprising contacting the cell with an agent that specifically binds an LRRC33-TGF-β prodomain-TGF-β complex. In one embodiment, the agent comprises an antibody. In another embodiment, the antibody specifically binds an epitope comprised only by the LRRC33-TGF-β prodomain-TGF-β complex.

In another aspect, described herein is a method of promoting release of active TGF-β from an LRRC33-TGF-β prodomain-TGF-β complex, the method comprising contacting a cell that comprises an LRRC33-TGF-β prodomain-TGF-β complex, with an agent that destabilizes the LRRC33-TGF-β prodomain-TGF-β complex, wherein destabilization of the complex promotes release of active TGF-β from the LRRC33-TGF-β prodomain-TGF-β complex. In one embodiment, the agent is an antibody or an antigen binding fragment thereof. In another embodiment, the antibody or antigen-binding fragment thereof binds an LRRC33 polypeptide epitope. In another embodiment, the antibody or antigen-binding fragment thereof specifically binds an epitope comprised only by the LRRC33-TGF-β prodomain complex.

In another embodiment, the cell is a macrophage.

In another aspect, described herein is a method of promoting immunosupression in a subject in need thereof, the method comprising, administering an agent that destabilizes an LRRC33-TGF-β prodomain-TGF-β complex, wherein the administering promotes release of active TGF-β from the complex, thereby promoting immunosuppression. In one embodiment, the agent is an antibody or an antigen-binding fragment thereof. In another embodiment, the antibody or an antigen binding fragment thereof specifically binds an LRRC33 polypeptide epitope. In another embodiment, the antibody or antigen-binding fragment thereof specifically binds an epitope comprised only by the LRRC33-TGF-β prodomain complex.

In another embodiment, the subject has a disease or disorder selected from the group consisting of chronic inflammation, autoimmune disease or fibrosis.

In another aspect, described herein is a composition comprising a fragment of an LRRC33 polypeptide that binds to TGF-β prodomain. In one embodiment, the fragment of LRRC33 comprises the LRRC33 ectodomain. In one embodiment, the composition further comprises a checkpoint inhibitor. In another embodiment, the composition further comprises an anti-PD-1 agent. In yet another embodiment, the composition further comprises anti-PD-1 antibody clone RMP1-14.

In another aspect, described herein is an isolated nucleic acid sequence encoding an LRRC33 polypeptide fragment that binds to TGF-β prodomain. In another embodiment, the isolated nucleic acid sequence is operably linked to a regulatory element. In another embodiment, the regulatory element permits tissue- or cell-specific expression of the nucleic acid sequence encoding the fragment of an LRRC33 polypeptide.

Also provided herein is a vector comprising an isolated nucleic acid sequence encoding an LRRC33 polypeptide fragment that binds to TGF-β prodomain.

Also provided herein is a cell comprising a nucleic acid sequence encoding an LRRC33 polypeptide fragment that binds to TGF-β prodomain or comprising a vector encoding such sequence. In one embodiment, the fragment of an LRRC33 polypeptide is expressed on the cell's surface. In another embodiment, the cell is a mammalian cell. In another embodiment, the cell is a human cell.

In another aspect, described herein is an antibody or an antigen-binding fragment thereof comprising the variable heavy chain sequence of SEQ ID NO: 2, wherein the antibody specifically binds to an LRRC33 polypeptide of SEQ ID NO: 1.

In another aspect, described herein is an antibody or antigen-binding fragment thereof comprising the variable light chain sequence of SEQ ID NO: 3, wherein the antibody specifically binds to an LRRC33 polypeptide of SEQ ID NO: 1.

In another aspect, described herein is an antibody or an antigen-binding fragment thereof comprising the variable heavy chain sequence of SEQ ID NO: 2 and the variable light chain sequence of SEQ ID NO: 3, wherein the antibody specifically binds to an LRRC33 polypeptide of SEQ ID NO: 1.

In one embodiment of any of the antibodies described herein, the antigen-binding fragment is an Fab, Fab', F(ab')2, Fv or single chain Fv (ScFv).

In another aspect, described herein is a composition comprising a fragment of an LRRC33 polypeptide that binds TGF-β prodomain, bound to a TGF-β prodomain polypeptide. In one embodiment, the LRRC33 polypeptide fragment is covalently linked to the TGF-β prodomain polypeptide. In another embodiment, the LRRC33 polypeptide fragment is covalently linked to the TGF-β prodomain polypeptide via disulfide bonds. In one embodiment, the composition further comprises a checkpoint inhibitor. In another embodiment, the composition further comprises an anti-PD-1 agent. In yet another embodiment, the composition further comprises anti-PD-1 antibody clone RMP1-14. In another embodiment, the composition further comprises an adjuvant.

In another aspect, described herein is a method of treating cancer comprising administering to subject in need thereof an agent that stabilizes LRRC33-TGF-β prodomain complex, and a checkpoint inhibitor. In one embodiment, the agent comprises an antibody or antigen-binding fragment thereof. In another embodiment, the antibody or antigen-binding fragment thereof specifically binds an epitope on LRRC33. In another embodiment, the antibody or antigen-binding fragment thereof specifically binds an epitope comprised only by the LRRC33-TGF-β prodomain-TGF-β complex.

In one embodiment, the cancer is carcinoma. In another embodiment, the cancer is melanoma or colon cancer. In another embodiment, the cancer is resistant to anti-PD-1 agent.

In one embodiment, the checkpoint inhibitor is selected from the group consisting of: an anti-PD-1 agent, an anti-PDL-1 agent, an anti-CTLA4 agent, an anti-LAG3 agent, and an anti-TIM3 agent. In another embodiment, the anti-PD-1 agent is anti-PD-1 antibody clone RMP1-14.

In another aspect, described herein is a method of treating melanoma or colon cancer comprising administering to subject in need thereof an agent that stabilizes LRRC33-TGF-β prodomain complex and a checkpoint inhibitor.

In another aspect, described herein is a method of treating melanoma or colon cancer comprising administering to subject in need thereof an agent that stabilizes LRRC33-TGF-β prodomain complex and anti-PD-1 agent.

In yet another aspect, described herein is a method of treating melanoma or colon cancer comprising administering to subject in need thereof an agent that stabilizes LRRC33-TGF-β prodomain complex and anti-PD-1 antibody clone RMP1-14.

In another aspect, described herein is a composition comprising an agent that stabilizes LRRC33-TGF-β prodomain complex and a checkpoint inhibitor. In one embodiment, the agent comprises an antibody or antigen-binding fragment thereof. In another embodiment, the antibody or antigen-binding fragment thereof specifically binds an epitope on LRRC33. In yet another embodiment, the antibody or antigen-binding fragment thereof specifically binds an epitope comprised only by the LRRC33-TGF-β prodomain-TGF-β complex.

In one embodiment, the checkpoint inhibitor is selected from the group consisting of: an anti-PD-1 agent, an anti-PDL-1 agent, an anti-CTLA4 agent, and an anti-TIM3 agent. In another embodiment, the anti-PD-1 agent is anti-PD-1 antibody clone RMP1-14.

In another aspect, described herein is a composition comprising an agent that stabilizes LRRC33-TGF-β prodomain complex and an anti-PD-1 agent.

In another aspect, described herein is a composition comprising an agent that stabilizes LRRC33-TGF-β prodomain complex and anti-PD-1 antibody clone RMP1-14.

In another aspect, described herein is a composition comprising any of the antibodies or antigen binding fragments described herein and a checkpoint inhibitor.

In another aspect, described herein is a composition comprising any of the antibodies or antigen binding fragments described herein and an anti-PD-1 agent.

In another aspect, described herein is a composition comprising any of the antibodies or antigen binding fragments described herein and anti-PD-1 antibody clone RMP1-14.

In another aspect, described herein is the use of any composition described herein for the treatment of cancer.

In another aspect, described herein is the use of any composition described herein for the treatment of carcinoma.

In another aspect, described herein is the use of any composition described herein for the treatment of melanoma or colon cancer.

DEFINITIONS

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to an embodiment, yet open to the inclusion of unspecified elements, whether useful or not.

As used herein the term "consisting essentially of" refers to those elements required for a given embodiment. The term permits the presence of elements that do not materially affect the basic and novel or functional characteristic(s) of that embodiment of the invention.

As used herein the term "consisting of" refers to compositions, methods, and respective components thereof as described herein, which are exclusive of any element not recited in that description of the embodiment.

The terms "disease", "disorder", or "condition" are used interchangeably herein, refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, or affectation.

The term "in need thereof" when used in the context of a therapeutic or prophylactic treatment, means having a disease, being diagnosed with a disease, or being in need of preventing a disease, e.g., for one at risk of developing the disease. Thus, a subject in need thereof can be a subject in need of treating or preventing a disease.

As used herein, the terms "treat," "treatment," "treating," or "amelioration" refer to therapeutic treatments, wherein the object is to reverse, alleviate, ameliorate, inhibit, slow down or stop the progression or severity of a disease or disorder. The term "treating" includes reducing or alleviating at least one adverse effect or symptom of a disorder. Treatment is generally "effective" if one or more symptoms or clinical markers are reduced. Alternatively, or in addition, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality. For example, treatment is considered effective if the condition is stabilized, or the elevated blood glucose levels are normalized. The term "treatment" of a disease also includes providing relief from the symptoms or side-effects of the disease (including palliative treatment).

As used herein, the term "administering," refers to the placement of a compound as disclosed herein into a subject by a method or route that results in at least partial delivery of the agent at a desired site. Pharmaceutical compositions comprising the compounds disclosed herein can be administered by any appropriate route which results in an effective treatment in the subject, including but not limited to intravenous, intraarterial, injection or infusion directly into a tissue parenchyma, etc. Where necessary or desired, administration to the CNS can include, for example, intracerebroventricular ("icv") administration, intranasal administration, intracranial administration, intracelial administration, intracerebellar administration, or intrathecal administration.

As used herein, a "subject", "patient", "individual" and like terms are used interchangeably and refers to a vertebrate, preferably a mammal, more preferably a primate, still more preferably a human. Mammals include, without limitation, humans, primates, rodents, wild or domesticated animals, including feral animals, farm animals, sport animals, and pets. Primates include, for example, chimpanzees, cynomologous monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, and canine species, e.g., dog, fox, wolf, avian species, e.g., chicken, emu, ostrich, and fish, e.g., trout, catfish and salmon. The terms, "individual," "patient" and "subject" are used interchangeably herein. A subject can be male or female.

Preferably, the subject is a mammal. The mammal can be a human, non-human primate, mouse, rat, dog, cat, horse, or cow, but is not limited to these examples. Mammals other than humans can be advantageously used as subjects that represent animal models of conditions or disorders associated with or involving activities of the innate immune system. Non-limiting examples include murine tumor models, and murine models of autoimmune disease. In addition, the compositions and methods described herein can be used to treat domesticated animals and/or pets.

A subject can be one who has been previously diagnosed with or identified as suffering from a TGF-β associated disorder or a disorder involving or characterized by dysregulated or inappropriate activity of cells of the myeloid lineage, including, but not limited to microglia and other macrophages. A subject can be one who is diagnosed and currently being treated for, or seeking treatment, monitoring, adjustment or modification of an existing therapeutic treatment, or is at a risk of developing a given disorder.

As used herein, the terms "protein", "peptide" and "polypeptide" are used interchangeably to designate a series of amino acid residues connected to each other by peptide bonds between the alpha-amino and carboxy groups of adjacent residues. The terms "protein", "peptide" and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein", "peptide" and "polypeptide" are used interchangeably herein when referring to a gene product and fragments thereof.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically acceptable carrier" means a pharmaceutically-acceptable material, composition or vehicle, such as a liquid or solid filler, diluent, excipient, manufacturing aid or solvent encapsulating material necessary or used in formulating an active ingredient or agent for delivery to a subject. Each carrier must be "acceptable" in the sense of being compatible with the other ingredients of the formulation and not injurious to the patient.

The terms "increased", "increase", or "enhance" are all used herein to generally mean an increase by a statically significant amount; for the avoidance of doubt, the terms "increased", "increase", or "enhance", mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The terms, "decrease", "reduce", "reduction", "lower" or "lowering," or "inhibit" are all used herein generally to mean a decrease by a statistically significant amount. For example, "decrease", "reduce", "reduction", or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

An "antibody", as used herein refers to an immunoglobulin molecule capable of specific binding to a target, (e.g, LRRC33 polypeptide or a fragment thereof), through at least one antigen recognition site, located in the variable region of the immunoglobulin molecule. As used herein, the term encompasses not only intact polyclonal or monoclonal antibodies, but also fragments thereof (such as Fab, Fab', F(ab')2, Fv), single chain (ScFv), mutants thereof, fusion proteins comprising an antibody portion, and any other modified configuration of the immunoglobulin molecule that comprises an antigen recognition site. An antibody includes an antibody of any class, such as IgG, IgA, IgD, IgE or IgM (or sub-class thereof), and the antibody need not be of any particular class.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature, 256:495, or may be made by recombinant DNA methods such as described in U.S. Pat. No. 4,816,567. The monoclonal antibodies may also be isolated from phage libraries generated using the techniques described in McCafferty et al., 1990, Nature, 348:552-554, for example.

As used herein, "humanized" antibodies refer to forms of non-human (e.g. murine) antibodies that are specific chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody.

"An isolated antibody"—As used herein, an "isolated antibody" is one that has been separated and/or recovered from a component of its natural environment. Contaminant components of its natural environment are materials that would interfere with diagnostic or therapeutic uses of the antibody, and may include enzymes, hormones, and other proteinaceous or non proteinaceous components. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity as shown by SDS-PAGE under reducing or non-reducing conditions and using Coomassie blue or, preferably, silver staining. Isolated antibody includes the antibody in situ within recombinant cells since at least one component of the antibody's natural environment will not be present. Ordinarily, however, isolated antibody will be prepared by at least one purification step.

"Affinity variants"—As used herein, the term "affinity variant" refers to a variant antibody which exhibits one or more changes in amino acid sequence compared to a reference antibody, wherein the affinity variant exhibits an altered affinity for a given antigen in comparison to the reference antibody. Typically, affinity variants will exhibit an improved affinity the antigen, as compared to the reference antibody. The improvement may be either a lower $K_D$ for the antigen, or a faster off-rate, or an alteration in the pattern of cross-reactivity with antigen homologues. Affinity variants typically exhibit one or more changes in amino acid sequence in the CDRs, as compared to the reference antibody. Such substitutions may result in replacement of the original amino acid present at a given position in the CDRs with a different amino acid residue, which may be a naturally occurring amino acid residue or a non-naturally occurring amino acid residue. The amino acid substitutions may be conservative or non-conservative.

"Epitope"—As used herein, the term "epitope" refers to a specific arrangement of amino acids located on a peptide or protein or proteins to which an antibody binds. Epitopes often consist of a chemically active surface grouping of molecules such as amino acids or sugar side chains, and have specific three dimensional structural characteristics as well as specific charge characteristics. Epitopes can be linear or conformational, i.e., involving two or more sequences of amino acids in various regions of the antigen that may not necessarily be contiguous.

"Fragment"—As used herein, the term "fragment" when applied to an antibody refers to a part or region of an antibody or antibody chain comprising fewer amino acid residues than an intact or complete antibody or antibody chain. The term "antigen-binding fragment" refers to a polypeptide fragment of an immunoglobulin or antibody that binds antigen or competes with intact antibody (i.e., with the intact antibody from which they were derived) for antigen binding (i.e., specific binding to human LRRC33). As used herein, the term "fragment" of an antibody molecule includes antigen-binding fragments of antibodies, for example, an antibody light chain variable domain (VL), an antibody heavy chain variable domain (VH), a single chain antibody (scFv), a F(ab')2 fragment, a Fab fragment, an Fd fragment, an Fv fragment, a single domain antibody fragment (DAb), a one-armed (monovalent) antibody, diabodies or any antigen-binding molecule formed by combination, assembly or conjugation of such antigen binding fragments. Fragments can be obtained, e.g., via chemical or enzymatic treatment of an intact or complete antibody or antibody chain or by recombinant means.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. Molec. Biol. 273:927-948)). As used herein, a CDR may refer to CDRs defined by either approach or by a combination of both approaches.

A "constant region" of an antibody refers to the constant region of the antibody light chain or the constant region of the antibody heavy chain, either alone or in combination. The constant region does not vary with respect to antigen specificity.

"Heavy chain region"—As used herein, the term "heavy chain region" includes amino acid sequences derived from the constant domains of an immunoglobulin heavy chain. A polypeptide comprising a heavy chain region comprises at least one of: a CH1 domain, a hinge (e.g., upper, middle, and/or lower hinge region) domain, a CH2 domain, a CH3 domain, or a variant or fragment thereof. In an embodiment, an antibody or an antigen binding fragment thereof may comprise the Fc region of an immunoglobulin heavy chain (e.g., a hinge portion, a CH2 domain, and a CH3 domain). In another embodiment, an antibody or an antigen binding fragment thereof lacks at least a region of a constant domain (e.g., all or part of a CH2 domain). In certain embodiments, at least one, and preferably all, of the constant domains are derived from a human immunoglobulin heavy chain. For example, in one preferred embodiment, the heavy chain region comprises a fully human hinge domain. In other preferred embodiments, the heavy chain region comprising a fully human Fc region (e.g., hinge, CH2 and CH3 domain sequences from a human immunoglobulin). In certain embodiments, the constituent constant domains of the heavy chain region are from different immunoglobulin molecules. For example, a heavy chain region of a polypeptide may comprise a domain derived from an IgG1 molecule and a hinge region derived from an IgG3 or IgG4 molecule. In other embodiments, the constant domains are chimeric domains comprising regions of different immunoglobulin molecules. For example, a hinge may comprise a first region from an IgG1 molecule and a second region from an IgG3 or IgG4 molecule. As set forth above, it will be understood by one of ordinary skill in the art that the constant domains of the heavy chain region may be modified such that they vary in amino acid sequence from the naturally occurring (wild-type) immunoglobulin molecule. That is, the polypeptides of the invention disclosed herein may comprise alterations or modifications to one or more of the heavy chain constant domains (CH1, hinge, CH2 or CH3) and/or to the light chain constant domain (CL). Exemplary modifications include additions, deletions or substitutions of one or more amino acids in one or more domains.

"Hinge region"—As used herein, the term "hinge region" includes the region of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al. J. Immunol. 1998 161:4083).

The terms "hypervariable loop" and "complementarity determining region" are not strictly synonymous, since the hypervariable loops (HVs) are defined on the basis of structure, whereas complementarity determining regions (CDRs) are defined based on sequence variability (Kabat et al., Sequences of Proteins of Immunological Interest, 5th Ed. Public Health Service, National Institutes of Health, Bethesda, Md., 1983) and the limits of the HVs and the CDRs may be different in some VH and VL domains. The CDRs of the VL and VH domains can typically be defined as comprising the following amino acids: residues 24-34 (CDRL1), 50-56 (CDRL2) and 89-97 (CDRL3) in the light chain variable domain, and residues 31-35 or 31-35b (CDRH1), 50-65 (CDRH2) and 95-102 (CDRH3) in the heavy chain variable domain; (Kabat et al., Sequences of Proteins of Immunological Interest, 5th Ed. Public Health Service, National Institutes of Health, Bethesda, Md. (1991)). Thus, the HVs may be comprised within the corresponding CDRs and references herein to the "hypervariable loops" of VH and VL domains should be interpreted as also encompassing the corresponding CDRs, and vice versa, unless otherwise indicated. The more highly conserved regions of variable domains are called the framework region (FR), as defined below. The variable domains of native heavy and light chains each comprise four FRs (FR1, FR2, FR3 and FR4, respectively), largely adopting a [beta]-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., J. Mol. Biol. 227: 799-817 (1992)); Tramontano et al., J. Mol. Biol, 215: 175-182 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

"Fv"—As used herein, the term "Fv" is the minimum antibody fragment that contains a complete antigen-recognition and -binding site. This fragment consists of a dimer of one heavy- and one light-chain variable region domain in tight, non-covalent association.

From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Isolated nucleic acid"—As used herein, is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man. The term "polypeptide" is used in its conventional meaning, i.e., as a sequence of amino acids.

"In the context of an antibody or antigen-binding fragment thereof, the term "specificity" or "specific for" refers to the number of different types of antigens or antigenic determinants to which a particular antibody or antigen-binding fragment thereof can bind. The specificity of an antibody or antigen-binding fragment or portion thereof can be determined based on affinity and/or avidity. The affinity, represented by the equilibrium constant for the dissociation ($K_D$) of an antigen with an antigen-binding protein, is a measure for the binding strength between an antigenic determinant and an antigen-binding site on the antigen-binding protein: the lesser the value of the $K_D$, the stronger the binding strength between an antigenic determinant and the antigen-binding molecule. Alternatively, the affinity can also be expressed as the affinity constant ($K_A$), which is $1/K_D$). As will be clear to the skilled person, affinity can be determined in a manner known per se, depending on the specific antigen of interest. Accordingly, an antibody or antigen-binding fragment thereof as defined herein is said to be "specific for" a first target or antigen compared to a second target or antigen when it binds to the first antigen with an affinity (as described above, and suitably expressed, for example as a $K_D$ value) that is at least 50 times, such as at least 100 times, and preferably at least 1000 times, and up to 10,000 times or more better than the affinity with which said amino acid sequence or polypeptide binds to another target or polypeptide. Preferably, when an antibody or antigen-binding fragment thereof is "specific for" a target or antigen, compared to another target or antigen, it can bind the target or antigen, but does not bind the other target or antigen.

However, as understood by one of ordinary skill in the art, in some embodiments, where a binding site on a target is shared or partially shared by multiple, different ligands, an antibody or antigen binding fragment thereof can specifically bind to a target, such as LRRC33, and have the functional effect of inhibiting/preventing binding of multiple, different ligands.

Avidity is the measure of the strength of binding between an antigen-binding molecule and the pertinent antigen. Avidity is related to both the affinity between an antigenic determinant and its antigen binding site on the antigen-binding molecule, and the number of pertinent binding sites present on the antigen-binding molecule. Typically, antigen-binding proteins will bind to their cognate or specific antigen with a dissociation constant ($K_D$ of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ $M^{-1}$) is generally considered to indicate non-specific binding. The $K_D$ for biological interactions which are considered meaningful (e.g., specific) are typically in the range of $10^{-10}$ M (0.1 nM) to $10^{-5}$ M (10000 nM). The stronger an interaction is, the lower is its $K_D$. Preferably, a binding site on an anti-LAP antibody or antigen-binding fragment thereof described herein will bind with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Immunology by Werner Luttmann, published by Elsevier, 2006. Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other than in the operating examples, or where otherwise indicated, all numbers expressing quantities of ingredients or reaction conditions used herein should be understood as modified in all instances by the term "about." The term "about" when used in connection with percentages means±1% of the value being referred to. For example, about 100 means from 99 to 101.

Although methods and materials similar or equivalent to those described herein can be used in the practice or testing of this disclosure, suitable methods and materials are described below. The abbreviation, "e.g.," is derived from the Latin exempli gratia, and is used herein to indicate a non-limiting example. Thus, the abbreviation "e.g.," is synonymous with the term "for example."

As used in this specification and appended claims, the singular forms "a," "an", and "the" include plural references unless the context clearly dictates otherwise. Thus for example, reference to "the method" included one or more methods, and/or steps of the type described herein and/or which will become apparent to those persons skilled in the art upon reading this disclosure and so forth.

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

BRIEF DESCRIPTION OF THE DRAWINGS

FIGS. 5A-5H show whole bone marrow transplantation rescues neurological defects. (A) Kaplan-Meier survival curve of transplanted mice, **P<0.01 (MantelCox) test. (B-D) Donor/Host chimerism in transplanted animals. Representative FACS analysis of microglia cells stained for CD45.1 and CD45.2 among Mac1+ and CD39HIGH cells at 5 month post BMT (n=4); (E-F) Clinical scores. (G-H) Percent and absolute numbers of microglia in transplanted recipients.

DETAILED DESCRIPTION

As noted above, the technology described herein is based, in part, on the discovery that LRRC33 polypeptide covalently binds proTGF-β and influences the availability of mature, active TGF-β. The manipulation of LRRC33 and its interaction with proTGF-β can be exploited to modulate TGF-β-regulated processes. The cell-type-specific expression of LRRC33 indicates that the manipulation of LRRC33 activity and/or expression can be useful for the treatment or prevention of TGF-β-mediated disorders.

The following describes methods and compositions that apply the discovery that LRRC33 covalently interacts with and regulates the activity of pro-TGF-β in vivo.

Leucine-Rich Repeat-Containing Protein 33 (LRRC33)

Figure 1A:
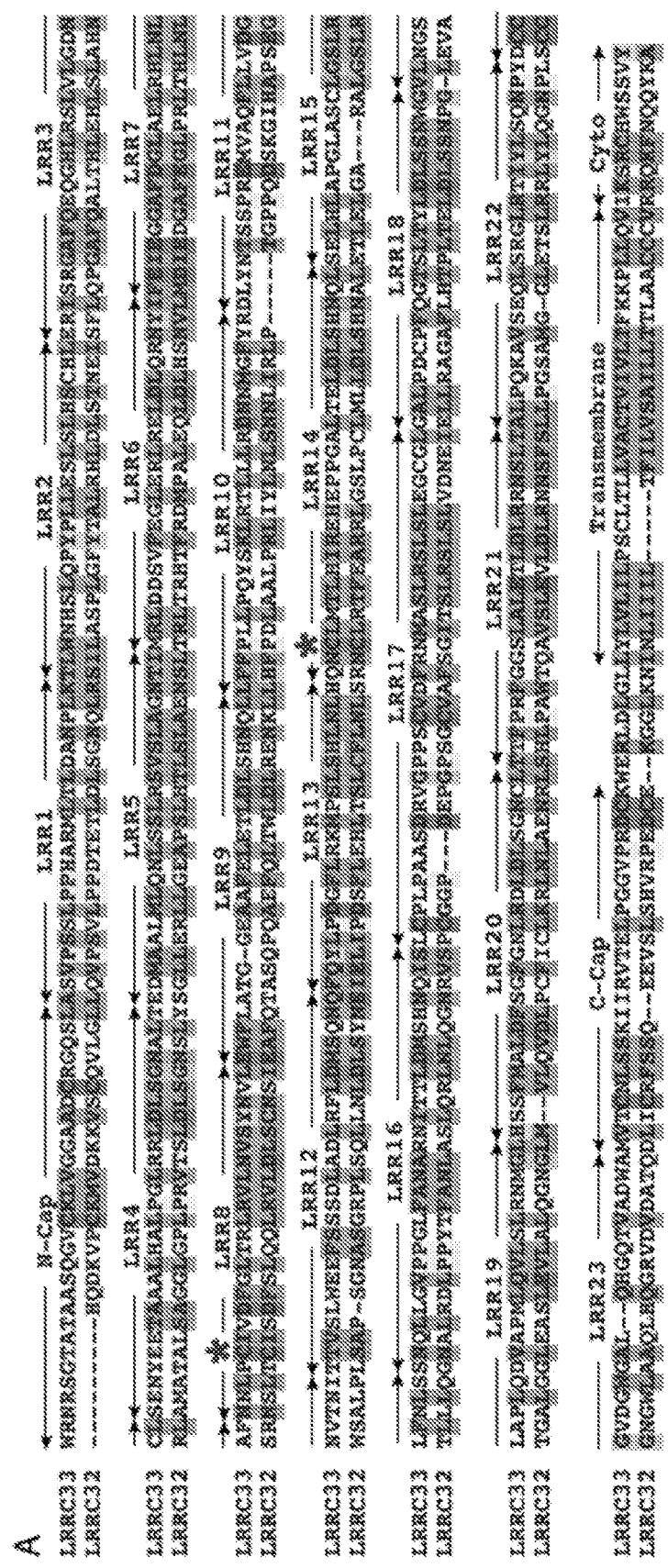
FIGS. 1A-1H show LRRC33 is a homolog of GARP. (A) LRRC33 sequence alignment. Asterisks (*) mark two cysteines that disulfide link to pro-TGF-β1 {Wang, 2012 #20133}. X1 and X5 mark GARP/LRRC33 chimaera exchange positions. (B) Phylogenetic tree showing relationship of LRRC33 to top human BLAST hits with similar numbers of LRR. Branch lengths are to the scale shown. Proteins in the same branch in >95% of bootstrap replicates appear in teardrop highlights. Ectodomains were aligned with MAFFT G-INS-i strategy with gap insertion and extension penalties of 3 and 1, respectively {Katoh, 2013 #24511}. Trees were calculated on the same MAFFT server with the NJ method using all gap-free sites, the JTT model, estimation of a, and 1000 bootstrap samples. (C) Microarray analysis of LRRC33 mRNA expression in different cell types in murine hematopoietic system. (D) LRRC33 and TGF-β1 mRNA levels positively correlate in normal human tissue, datasets from BioGPS. (E) LRRC33 and TGF-β1 mRNA expression in human cancer cell lines, datasets from CCLE (cancer cell line encyclopedia); darker dots represent cancer cell lines from haematopoietic and lymphoid tissue; lighter dots represent cancer cell lines from solid tissue. (F, G) X-gal staining showing LacZ expression in 4-month-old WT, Lrrc33 and Garp heterozygous mice. (H) Mouse brain RNA-Seq data {Zhang, 2014 #24481}; heat map displays genes that were preferentially expressed in different cell types in CNS.

Leucine-Rich Repeat-Containing Protein 33 (LRRC33) or Negative Regulator Of Reactive Oxygen Species (NRROS) is a 76 kDa homolog of Glycoprotein A Repetitions Predominant (GARP). It is a member of the leucine-rich repeat (LRR) family of proteins. The protein comprises an N-terminal signal peptide, an ectodomain containing 23 LRRs, a transmembrane domain, and an 11 residue cytoplasmic domain (FIG. 1A). Human and mouse LRRC33 share more than 80% amino acid identity. As used herein "LRRC33" refers to a full length human LRRC33 polypeptide or fragment thereof. In some embodiments, "LRRC33" refers to an ortholog of human LRRC33 polypeptide or fragment thereof. The "LRRC33" can be mammalian LRRC33 polypeptide. The "LRRC33" can also be a functional isoform of the full length LRRC33 polypeptide or fragment thereof. In some embodiments, the "LRRC33" includes or is derived from human LRRC33 polypeptide The complete amino acid sequence of the human LRRC33 is;

(SEQ ID NO: 1)

```
  1    mellplwlcl gfhfltvgwr nrsgtataas qgvcklvgga adcrggslas vpsslpphar
 61    mltldanplk tlwnhslqpy plleslslhs chlerisrga fgegghlrsl vlgdnclsen
121    yeetaaalha lpglrrldls gnaltedmaa lmlqnlsslr syslagntim rlddsvfegl
181    erlreldlqr nyifeiegga fdglaelrhl nlafnnlpci vdfgltrlry lnvsynvlew
241    flatggeaaf eletldlshn qllffpllpq ysklrtlllr dnnmgfyrdl yntsspremv
301    aqfllvdgnv tnittvslwe efsssdladl rfldmsqnqf qylpdgflrk mpslshlnlh
361    qnclmtlhir eheppgalte ldlshnqlse lhlapglasc lgslrlfnls snqllgvppg
421    lfanarnitt ldmshngisl cplpaasdry gppscvdfrn maslrslsle gcglgalpdc
481    pfqgtsltyl dlssnwgvin gslaplqdva pmlqvlslrn mglhssfmal dfsgfgnlrd
541    ldlsgncltt fprfggslal etldlrrnsl talpqkayse qlsrglrtiy lsqnpydccg
```

```
-continued
601  vdgwgalqhg qtvadwamvt cnlsskiiry telpggvprd ckwerldlgl lylvlilpsc 661  ltllvactvi vltfkkpllq viksrchwss vy
```

(See GenBank Accession NP_940967.1, which is incorporated herein in its entirety). Signal peptide, amino acids 1-18 of SEQ ID NO: 1; extracellular/ectodomain, amino acids 19-650 of SEQ ID NO: 1; transmembrane domain, amino acids 651-671 of SEQ ID NO: 1; cytoplasmic domain, amino acids 672-692 of SEQ ID NO: 1.

The minimum, central biological activity, and/or biological effect of the LRRC33 polypeptide or a fragment thereof as it relates to the methods and composition herein includes its ability to bind to pro-TGF-β. Polypeptide comprising conservative substitutions, deletions or additions to sequence of SEQ ID NO:1 that do not affect the ability of LRRC33 to bind to pro-TGF-β are also contemplated. Strongly similar amino acids can include, for example, conservative substitutions known in the art. Percent identity and/or homology can be calculated using alignment methods known in the art. For instance, alignment of the sequences can be conducted using publicly available software such as BLAST, Align and ClustalW2. Those skilled in the art can determine the appropriate parameters for alignment, but the default parameters for BLAST are specifically contemplated. In some embodiments, the LRRC33 polypeptide retains at least 85%, at least 90%, at least 91%, at least 92%, at least 93%, at least 94%, at least 95%, at least 96%, at least 97%, at least 98% or at least 99% of the biological activity of human LRRC33 of SEQ ID NO:1.

The LRRC33 polypeptide can be recombinant, purified, isolated, naturally occurring or synthetically produced. The term "recombinant" when used in reference to a nucleic acid, protein, cell or a vector indicates that the nucleic acid, protein, vector or cell containing them have been modified by introduction of a heterologous nucleic acid or protein or the alteration of a native nucleic acid or a protein, or that the cell is derived from a cell so modified. The term "heterologous" (meaning "derived from a different organism") refers to the fact that often the transferred protein was initially derived from a different cell type or a different species from the recipient. Typically the protein itself is not transferred, but instead the genetic material coding for the protein (often the complementary DNA or cDNA) is added to the recipient cell. Methods of generating and isolating recombinant polypeptides are known to those skilled in the art and can be performed using routine techniques in the field of recombinant genetics and protein expression. For standard recombinant methods, see Sambrook et al, Molecular Cloning: A Laboratory Manual, Cold Spring Harbor Laboratory Press, N Y (1989); Deutscher, Methods in Enzymology 182:83-9 (1990); Scopes, Protein Purification: Principles and Practice, Springer-Verlag, NY (1982). In some embodiments, the LRRC33 is in complex with pro-TGF-β.

Variants and fragments of LRRC33 are specifically contemplated herein, and can find use, for example, as (competitive) inhibitors of LRRC33 (e.g., for molecules that bind pro-TGF-β but, due to the lack of one or more functions or domains of the native LRRC33 protein, fail to mediate the effects of wild-type LRRC33 on TGF-β regulation), or alternatively, as activators or mimics of LRRC33 activity. Variants specifically contemplated include, for example, variants lacking either or both of cysteine residues Cys-200 and Cys-344 of SEQ ID NO: 1 shown herein to participate in disulfide bonding with pro-TGF-β, variants lacking the transmembrane domain, with or without the short intracellular domain, variants lacking one or more of the leucine-rich repeat domains, variants engineered to include additional or different leucine-rich repeats, variants engineered to lack one or more of the known or predicted glycosylation sites possessed by the wild-type polypeptide, or variants engineered to include one or more additional glycosylation sites relative to the wild-type polypeptide.

Agents

The term "agents" refer to any molecules capable of modulating the release (or retention) of TGF-β from the ternary complex of LRRC33-TGF-β prodomain-TGF-β. Agents can be for example, antagonists or agonists of the release of TGF-β from the ternary complex. The term "antagonist" as used herein, includes any molecule capable of binding to LRRC33 polypeptide to partially or fully inhibit biological activity of LRRC33 polypeptide, wherein the biological activity involves binding of LRRC33 with TGF-β prodomain to form the ternary complex of LRRC33-TGF-β prodomain-TGF-β or modulation of activation or release of active TGF-β from the ternary complex. Conversely, an "agonist" is a molecule that promotes or stimulates such biological activity of the LRRC33 polypeptide.

Agents that inhibit the expression of the LRRC33 gene include, for example, siRNA, shRNA, micro-RNA, aptamers, and antisense oligonucleotide. An inhibitor of gene expression can inhibit transcription, translation, RNA processing or some combination of these. "Effective inhibition of expression of a gene" will result in a decrease in gene product to a level sufficient e.g., to modulate the level of TGF-β released from the LRRC33-TGF-β prodomain-TGF-β complex.

In some embodiments, can be a small molecule. In some embodiments, the small molecule prevents or inhibits release of TGF-β from the LRRC33-TGF-β prodomain-TGF-β complex. In other embodiments, the small molecule promotes or increases the release of TGF-β from the LRRC33-TGF-β prodomain-TGF-β complex. The term "small molecule" refers to an organic or inorganic molecule, either natural (i.e., found in nature) or non-natural (i.e., not found in nature), which can include, but is not limited to a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" J. Am. Chem. Soc. 120:8565, 1998; incorporated herein by reference). In certain other preferred embodiments, natural-product-like small molecules are utilized.

Generally, small molecules have molecular weights of less than 10 kDa (e.g., less than: 10 kDa; 9 kDa; 8 kDa; 7 kDa; 6 kDa; 5 kDa; 4 kDa; 3 kDa; 2 kDa; or 1 kDa).

In some embodiments "agents" as described herein can be antibody or antigen-binding fragment thereof. Antibodies or antigen binding fragments thereof useful in the methods and compositions described herein are described below.

In embodiments of various aspects, "agent" refers a molecule capable of modulating a checkpoint molecule. Checkpoint inhibitors useful in the methods and compositions described herein are described below.

Compositions

Provided herein are compositions useful for modulating the release (or retention) of TGF-β for the ternary LRRC33-TGF-β prodomain-TGF-β complex. These can be beneficial in the treatment of disorders involving both immunosuppression and inappropriate immune activity.

In one aspect, the composition comprises an agent capable of binding LRRC33 polypeptide, LRRC33 polypeptide in complex with TGF-β prodomain, or the LRRC33-TGF-β prodomain-TGF-β complex. Compositions as described herein can also include a molecule capable of stabilizing the TGF-β growth factor within the LRRC33-TGF-β prodomain-TGF-β complex to inhibit TGF-β release, or capable of destabilizing LRRC33-TGF-β prodomain-TGF-β complex so that the TGF-β growth factor is released.

In one aspect, provided herein is a composition comprising a fragment of an LRRC33 polypeptide that binds to TGF-β prodomain. A fragment is necessarily less than the entire mature LRRC33 polypeptide. It is recognized that LRRC33 is produced as a polypeptide with a signal sequence. The mature polypeptide lacks the signal sequence, but a mature polypeptide lacking only the signal sequence is not a "fragment" as the term is used herein. Rather, a fragment is a polypeptide with less than the entire mature LRRC33 polypeptide that retains the ability to bind TGF β prodomain. A fragment consisting of the LRRC33 ectodomain is but one example of an LRRC33 fragment as the term is used herein.

In one embodiment, the compositions described herein further comprises a checkpoint inhibitor. In another embodiment, the composition described herein further comprises an anti-PD-1 inhibitor. In yet another embodiment, the composition described herein further comprises anti-PD-1 antibody clone RMP1-14.

As demonstrated herein, LRRC33 interacts with the ectodomain of the TGF-β prodomain polypeptide. Thus, a fragment of LRRC33 comprising the ectodomain is specifically contemplated for use in influencing the activities and interactions of the TGF-β prodomain polypeptide. The human LRRC33 extodomain comprises amino acids 19-650 of the polypeptide of SEQ ID NO: 1.

In one aspect, an isolated nucleic acid sequence encoding the LRRC33 polypeptide or fragment is provided. In some embodiments, the nucleic acid sequence can be operably linked to a regulatory element. In some embodiments, the isolated nucleic acid sequence is operably linked to a regulatory element. As used herein, "regulatory element" refers to a nucleic acid fragment that modulates the expression of a transcribable nucleic acid sequence that is operably linked to the regulatory element. When operably linked to a transcribable nucleic acid sequence, a regulatory element affects the transcriptional pattern of the transcribable nucleic acid sequence. Examples of a regulatory element include a promoter, an enhancer and a suppressor. In some embodiments, the regulatory element is a promoter e.g., a constitutive or an inducible promoter. In some embodiments, the regulatory element permits tissue or cell specific expression of the nucleic acid sequence to which it operably linked. In one aspect, provided herein are vectors comprising the nucleic acid sequence encoding an LRRC33 polypeptide or a fragment of an LRRC33 polypeptide, that binds to TGF-β prodomain. A vector includes a construct which is capable of delivering, and preferably expressing, one or more gene(s) or nucleic acid sequence(s) of interest in a cell of interest or host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

In some embodiments, provided herein is a cell comprising a heterologous nucleic acid sequence encoding an LRRC33 polypeptide, or a fragment of an LRRC33 polypeptide, that binds to TGF-β prodomain. In some embodiments, the cell is a myeloid cell selected from the group consisting of monocytes, neutrophils, macrophages, and dendritic cells. In some embodiments, the macrophage is an M2 macrophage. In some embodiments, the macrophage is a microglial cell. In some embodiments, the LRRC33 polypeptide or fragment of an LRRC33 polypeptide is expressed on the cell's surface. Nucleic acid encoding an LRRC33 polypeptide or fragment can be introduced to the cell using conventional procedures known in the art, including, without limitation, electroporation, DEAE Dextran transfection, calcium phosphate transfection, monocationic liposome fusion, polycationic liposome fusion, protoplast fusion, creation of an in vivo electrical field, DNA-coated microprojectile bombardment, injection with recombinant replication-defective viruses, homologous recombination, gene therapy, viral vectors, and naked DNA transfer, or any combination thereof. Viral and non-viral-based gene transfer methods can be used to introduce nucleic acids encoding polypeptides to cells or target tissues of the subject. Such methods can be used to administer nucleic acids encoding polypeptides to cells in vitro. Alternatively, or in addition, such polynucleotides can be administered for in vivo or ex vivo gene therapy uses. Non-viral vector delivery systems include DNA plasmids, naked nucleic acid, and nucleic acid complexed with, for example, a liposome or other delivery vehicle. Viral vector delivery systems include both DNA and RNA viruses, and can have either episomal or integrated genomes after delivery to the cell. Gene therapy procedures are described, for example, in Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds) (1995); and Yu et al., Gene Therapy 1:13-26 (1994).

RNA or DNA viral based systems can be used to target the delivery of polynucleotides carried by the virus to specific cells in the body and deliver the polynucleotides to the nucleus. Viral vectors can be administered directly to patients (in vivo) or they can be used to transfect cells in vitro. In some cases, the transfected cells are administered to patients (ex vivo). Conventional viral based systems for the delivery of polypeptides of the invention could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene, and high transduction efficiencies.

In one aspect, a composition comprises an agent that stabilizes LRRC33 polypeptide and a checkpoint inhibitor. In one embodiment, the composition further comprises an adjuvant.

In another aspect, a composition comprises an agent that stabilizes LRRC33 polypeptide and an anti-PD-1 agent. In one embodiment, the composition further comprises an adjuvant.

In one aspect, a composition comprises an agent that stabilizes LRRC33 polypeptide and anti-PD-1 antibody clone RMP1-14. In one embodiment, the composition further comprises an adjuvant.

In another aspect, a composition comprises any of the antibodies or fragments thereof described herein and a checkpoint inhibitor. In one embodiment, the composition further comprises an adjuvant.

In another aspect, a composition comprises any of the antibodies or fragments thereof described herein and an anti-PD-1 agent. In one embodiment, the composition further comprises an adjuvant.

In another aspect, a composition comprises any of the antibodies or fragments thereof described herein and anti-PD-1 antibody clone RMP1-14. In one embodiment, the composition further comprises an adjuvant.

In some embodiments of any of the aspects, a checkpoint inhibitor can be a small molecule, inhibitory RNA/RNAi molecule (both single and double stranded), an antibody, antibody reagent, or an antigen-binding fragment thereof that specifically binds to at least one immune checkpoint protein. Common checkpoints that are targeted for therapeutics include, but are not limited to PD-1, CTLA4, TIM3, LAG3 and PD-L1. Inhibitors of their checkpoint regulators are known in the art.

Non-limiting examples of checkpoint inhibitors (with checkpoint targets and manufacturers noted in parentheses) can include:

MGA271 (B7-H3: MacroGenics); ipilimumab (CTLA-4; Bristol Meyers Squibb); pembrolizumab (PD-1; Merck); nivolumab (PD-1; Bristol Meyers Squibb); atezolizumab (PD-L1; Genentech); galiximab (B7.1; Biogen); IMP321 (LAG3: Immuntep); BMS-986016 (LAG3; Bristol Meyers Squibb); SMB-663513 (CD137; Bristol-Meyers Squibb); PF-05082566 (CD137; Pfizer); IPH2101 (KIR; Innate Pharma); KW-0761 (CCR4; Kyowa Kirin); CDX-1127 (CD27; CellDex); MEDI-6769 (Ox40; MedImmune); CP-870,893 (CD40; Genentech); tremelimumab (CTLA-4; Medimmune); pidilizumab (PD-1; Medivation); MPDL3280A (PD-L1; Roche); MEDI4736 (PD-L1; AstraZeneca); MSB0010718C (PD-L1; EMD Serono); AUNP12 (PD-1; Aurigene); avelumab (PD-L1; Merck); durvalumab (PD-L1; Medimmune); TSR-022 (TIM3; Tesaro).

Programmed cell death 1 (PD-1) limits the activity of T cells in peripheral tissues at the time of an inflammatory response to infection and limits autoimmunity. PD-1 blockade in vitro enhances T-cell proliferation and cytokine production in response to a challenge by specific antigen targets or by allogeneic cells in mixed lymphocyte reactions. A strong correlation between PD-1 expression and response was shown with blockade of PD-1 (Pardoll, Nature Reviews Cancer, 12: 252-264, 2012). PD-1 blockade can be accomplished by a variety of mechanisms including antibodies that bind PD-1 or its ligand, PD-L1. Examples of PD-1 and PD-L1 blockers are described in U.S. Pat. Nos. 7,488,802; 7,943,743; 8,008,449; 8,168,757; 8,217,149, and PCT Published Patent Application Nos: WO03042402, WO2008156712, WO2010089411, WO2010036959, WO2011066342, WO2011159877, WO2011082400, and WO2011161699; which are incorporated by reference herein in their entireties. In certain embodiments the PD-1 inhibitors include anti-PD-L1 antibodies. PD-1 inhibitors include anti-PD-1 antibodies and similar binding proteins such as anti-PD-1 antibody clone RMP1-14, nivolumab (MDX 1106, BMS 936558, ONO 4538), a fully human IgG4 antibody that binds to and blocks the activation of PD-1 by its ligands PD-L1 and PD-L2; lambrolizumab (MK-3475 or SCH 900475), a humanized monoclonal IgG4 antibody against PD-1; CT-011 a humanized antibody that binds PD-1; AMP-224, a fusion protein of B7-DC; an antibody Fc portion; BMS-936559 (MDX-1105-01) for PD-L1 (B7-H1) blockade.

Pre-clinical and early clinical studies have shown synergistic effects with lymphocyte activation gene 3 protein (LAG3; also known as CD223) and T-cell immunoglobulin and mucin domain-containing 3 (TIM3; also known as HAVCR2) in combination with PD-1 inhibitors.

One aspect, described herein is a use of any of the compositions described herein for the treatment of cancer. Another aspect, described herein is a use of any of the compositions described herein for the treatment of carcinoma. Yet another aspect, described herein is a use of any of the compositions described herein for the treatment of melanoma or colon cancer. Administration, dosage, and assessment of the efficacy of the treatment is described herein below.

Antibodies and fragments thereof useful in the methods and compositions described herein.

Provided herein are antibodies or antibody binding fragments thereof capable of binding an epitope comprising one or more amino acids of LRRC33 polypeptide or an epitope of LRRC33 modified as a result of LRRC33 being complexed with TGF-β prodomain or with TGF-β prodomain and TGF-β. In some embodiments, the antibody can be for example, a whole antibody, a humanized antibody, a single chain antibody, a dimeric single chain antibody, a Fv, a Fab, a F(ab)'2, a defucosylated antibody, a bi-specific antibody, a diabody, a triabody, a tetrabody; or an antibody fragment selected from the group consisting of a unibody, a domain antibody, and a nanobody; or an antibody mimetic selected from the group consisting of an affibody, an affilin, an affitin, an adnectin, an atrimer, an evasin, a DARPin, an anticalin, an avimer, a fynomer, a versabody and a duocalin. In some embodiments, the antibody is a monoclonal antibody. In some embodiments, the antibody is a polyclonal antibody. In some embodiments, the antibody or the antigen binding fragment thereof binds an epitope on the LRRC33 polypeptide; e.g. one or more amino acid residues of LRRC33 of SEQ ID NO: 1. In one embodiment, the antibody or antigen binding fragment thereof binds to a conformational epitope. In one embodiment, the conformational epitope comprises one or more non-contiguous amino acids of LRRC33 of SEQ ID NO: 1. In another embodiment, a conformational epitope comprises structure of LRRC33 and structure of TGF-β prodomain, i.e., a conformational epitope formed by complex formation between LRRC33 and TGF-β prodomain. In another embodiment, a conformational epitope comprises structure of LRRC33, structure of TGF-β prodomain, and structure of TGF-β, i.e., a conformational epitope formed by ternary complex formation between LRRC33, TGF-β prodomain and TGF-β.

In another embodiment, the epitope is a binding-induced conformational epitope and comprises amino acids from LRRC33 only, but where the LRRC33 polypeptide adopts a different conformation in the presence of TGF-β prodomain. In some embodiments, the epitope comprises the residues Cys-200 and/or Cys-344 of human amino acid sequence (SEQ ID NO: 1).

In some embodiments, the antibody or antigen binding fragment thereof stabilizes the LRRC33-TGF-β prodomain-TGF-β complex and prevents activation and/or release of active TGF-β from the complex. In some embodiments, the antibody or antigen binding fragment thereof destabilizes the LRRC33-TGF-β prodomain-TGF-β complex and promotes release of active TGF-β from the complex.

In one embodiment, an antibody or antigen binding fragment thereof comprises the variable heavy chain sequence of SEQ ID NO: 2 and binds LRRC33 polypeptide of SEQ ID NO: 1.

SEQ ID NO: 2: VH (variable heavy chain):

```
                                               (SEQ ID NO: 2)
EFQLQQSGPELVKPGASVKMSCKASGYSFTDSYMDWVKQSNGKTLEW

IGLINPKYGTTTYNQKFKGKATLTVDQSSSTAYMQLNSLTSEDSAVY

FCASLYYDYSAWFAYWGQGTLVTVSA
```

CDR1 sequence (SEQ ID NO: 10 (amino acids 26-35 of SEQ ID NO: 2)).

```
                                              (SEQ ID NO: 10)
           GYSFTDSYMD
```

CDR2 sequence (SEQ ID NO: 11 (amino acids 52-57 of SEQ ID NO: 2)).

```
                                              (SEQ ID NO: 11)
           NPKYGT
```

CDR3 sequence (SEQ ID NO: 12 (amino acids 99-109 of SEQ ID NO: 2)).

```
                                              (SEQ ID NO: 12)
           LYYDYSAWFAY
```

In one embodiment, the antibody or antigen binding fragment thereof comprises the variable light chain sequence of SEQ ID NO: 3 and binds LRRC33 polypeptide of SEQ ID NO: 1.

SEQ ID NO: 3: VL (variable light chain)

```
                                               (SEQ ID NO: 3)
QAVVTQESALTTSPGETVTLTCRSSTGAVTTSNYANWVQEKPDHLFT

GLIGGTNNRAPGVPARFSGSLIGDKAALIITGAQTEDEAIYFCGLWF

SNRWVEGGGTKLTVV
```

CDR1 sequence (SEQ ID NO: 13 (amino acids 23-36 of SEQ ID NO: 3)).

```
                                              (SEQ ID NO: 13)
           RSSTGAVTTSNYAN
```

CDR2 sequence (SEQ ID NO: 14 (amino acids 52-58 of SEQ ID NO: 3)).

```
                                              (SEQ ID NO: 14)
           GTNNRAP
```

CDR3 sequence (SEQ ID NO: 15 (amino acids 91-99 of SEQ ID NO: 3)).

```
                                              (SEQ ID NO: 15)
           GLWFSNRWV.
```

CDRs of the VH and VL domains described herein are annotated per the numbering scheme of Chothia and Lesk (Chothia C, and Lesk A M. J Mol Biol. 1987; 196(4):901-17), which is incorporated herein by reference in its entirety.

Antibody Variants

In some embodiments, the antibody and/or antigen-binding portion thereof described herein can be a variant of a sequence described herein, e.g. a conservative substitution variant of an antibody polypeptide. Examples of substitution variants include conservative substitution of amino acids, e.g. in a VH or VL, domain, that do not alter the sequence of a CDR. A conservative substitution in a sequence not comprised by a CDR can be a substitution relative to a wild-type or naturally-occurring sequence, e.g. human or murine framework and/or constant regions of an antibody sequence. A variant amino acid or DNA sequence preferably is at least 90%, at least 91%, at least 92%, at least 93%, at least 94%, at least 95%, at least 96%, at least 97%, at least 98%, at least 99%, or more, identical to a native or reference sequence.

In one embodiment, an antibody or antigen-binding fragment thereof that competes with an antibody bearing the heavy and light chain variable domains of SEQ ID Nos 2 and 3, respectively, for binding to a polypeptide of SEQ ID NO:1 would be expected to have function similar to that of the antibody that includes SEQ ID NOs 2 and 3. Competition assays are known to those of ordinary skill in the art.

In another embodiment, an antibody useful in the compositions and methods described herein is a humanized antibody or antigen-binding fragment thereof that comprises one or more, e.g., two or more, three or more, four or more, five or more, or even all six CDRs of the antigen binding domain of an antibody bearing the heavy and light chain variable domains of SEQ ID Nos 2 and 3. The methodology for making humanized antibodies is well known to those of ordinary skill in the art, and once the CDRs of a non-human, e.g., murine or rat antibody are grafted onto the appropriate framework regions of a human antibody scaffold, the humanized antigen-binding domain can be engineered into any of a number of different antibody construct conformations as described herein, e.g., an scFv, a Fab, Fab', F(ab')2, or a diabody, among others.

It should be understood that one of ordinary skill in the art can use the antigen-binding domain of an antibody bearing the heavy and light chain variable domains of SEQ ID Nos 2 and 3, respectively, to generate new antibody constructs that bind an epitope formed by the binding of LRRC33 to the TGF-β prodomain or the LRRC33-TGF-β prodomain-TGF-β complex. In one embodiment, a random or systematic mutagenesis approach can provide, for example, variants of the parent antigen binding domain that bind the same epitope with similar, equal, or preferably, greater binding affinity relative to the parent antibody. Such methods can generate a library of variants encoded by phage vectors, and recombinant phage expressing variants that bind the chosen target can be selected by binding of phage displaying the encoded variants on their outer capsids. Phage display and in vitro affinity maturation of antibodies are described, for example, in Chowdhury & Pastan, Nature Biotech. 17: 568-572 (1999), Hawkins et al., J. Mol. Biol. 226: 889-896 (1992) and Gram et al., Proc. Natl. Acad. Sci. U.S.A. 89: 3576-3580 (1992), each of which is incorporated herein by reference. In one embodiment, an antibody as described herein includes an affinity matured variant of an antibody that binds the LRRC33-TGF-β prodomain-TGF-β complex. An affinity matured variant will bind its target epitope with at least 2× greater affinity relative to the starting antibody. In various embodiments, an affinity matured variant will bind its target epitope with at least 5× greater, 10× greater, 15× greater, 20× greater, 25× greater, 50× greater, 75× greater, 100× greater or more relative to the starting antibody.

In one embodiment, an affinity matured variant binds the LRRC33-TGF-β prodomain-TGF-β complex at the epitope bound by an antibody bearing the antigen-binding domains of the heavy and light chains of SEQ ID Nos 2 and 3. Such an affinity matured variant will compete with an antibody bearing the antigen-binding domains of the heavy and light chains of SEQ ID Nos 2 and 3 for binding to that epitope. Such variants will have alterations in their CDRs, and can have alterations in their framework regions relative to the starting antibody. The alterations can be, but are not necessarily conservative. The variants can have, for example, at least 80% identity in their CDRs relative to those of SEQ ID Nos 2 and 3. In alternative embodiments, the variants can have at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or greater identity in their CDRs relative to those of SEQ ID Nos 2 and 3.

CDR lengths vary from about 5 to about 16 amino acids. When considering a single CDR, variation by one amino acid will represent 20% (one in about 5) to 6.25% (one in about 16). It is contemplated, then, that affinity matured variants as described herein will have at least one variation in a CDR, which, depending upon the CDR in question, will represent 20% to 6.25% difference, or 80% to 93.75% identity, depending upon the CDR. Similarly, two amino acid differences will represent 40% to 12.5% variation, or 60% to 87.5% identity in the individual CDRs. When considering all CDRs in a variable heavy chain, there are about 29 amino acids, and one amino acid difference represents about 3.4%, or 96.6% identity. Similarly, when considering all CDRs in a variable light chain, there are about 27 amino acids, and a single variation represents about 3.7%, or 96.3% identity. Thus, a light chain variant that retains about 80% identity in its CDRs will have 5 or fewer amino acid changes in its CDRs, collectively, relative to the starting or reference heavy or light chain In embodiments wherein an antibody as described herein comprises at least one CDR which is not identical to the sequence of SEQ ID NOs: 10-15, the amino acid sequence of that at least one CDR can be selected by methods known to one of skill in the art. For example, Fujii, 2004, "Antibody affinity maturation by random mutagenesis" in Methods in Molecular Biology: Antibody Engineering 248: 345-349 (incorporated by reference herein in its entirety), particularly at FIG. 2 and Section 3.3, describes methods of generating a library for any CDR of interest. This allows one of ordinary skill in the art to identify alternative CDRs, including conservative substitution variants, as well as non-conservative variants, of the specific CDR sequences described herein, which, when present in an antibody or antigen-binding fragment thereof as described herein, provide an antibody or antigen-binding fragment which will bind an LRRC33 polypeptide or an epitope formed by the binding of LRCC33 to TGFβ prodomain. In some embodiments, the antibody or antigen-binding fragment thereof can inhibit sMIC. The method described in Fujii et al. also permits one of ordinary skill in the art to screen for a light chain sequence which will give the desired binding behavior when combined with a known heavy chain fragment and vice versa.

In one embodiment, the antibody binds native LRRC33 polypeptide. In another embodiment, the antibody recognizes native LRRC33 polypeptide and permits detection of, e.g., microglial cells or other LRRC33-expressing cells by FACS. An LRRC33 antibody as described herein does not cross-react with GARP.

Many methods of making antibodies are known. See e.g., J. Janin, Nature, 277:491-492 (1979); Wolfenden et al., Biochemistry, 20:849-855 (1981); Kyte and Doolite, J. Mol. Biol., 157:105-132 (1982); and Rose et al., Science, 229: 834-838 (1985). The following discussion is presented as a general overview of the techniques available; however, one of skill will recognize that many variations upon the following methods are known.

A number of immunogens can be used to produce antibodies specifically reactive with a target. Desirable targets as they relate to the methods and compositions described herein can include, but are not limited to LRRC33 polypeptide or a fragment thereof, LRRC33 polypeptide in complex with TGF-β prodomain, and a complex of LRRC33 or a fragment thereof with TGF-β prodomain and TGF-β. An immunogen can be for example an isolated recombinant, synthetic, or native LRRC33 polypeptide or a fragment thereof, LRRC33 polypeptide or a fragment thereof bound to TGF-β prodomain, or a complex of LRRC33 polypeptide, TGF-β prodomain and TGF-β. An immunogen can also include a polynucleotide encoding LRRC33 polypeptide or a fragment thereof, or even a fusion protein including determinants of LRRC33 and TGF-β prodomain with or without TGF-β. An immunogen can also include cells expressing such polypeptides. Polypeptides are optionally denatured, and optionally reduced for screening antibody libraries or other assays in which a putative target is expressed or denatured in a non-native secondary, tertiary, or quarternary structure.

In addition, antibodies can be raised to a desired target site, including individual, allelic, strain, or species variants of such target sites, both in its naturally occurring (full-length) form and in a recombinant form. Antibodies can be raised to a target site in either its native configuration or in a non-native configuration.

The desirable target (e.g., analyte, antigen, protein, etc.) as it relates to the methods and compositions described herein, is then injected into an animal capable of producing antibodies. Either monoclonal or polyclonal antibodies can be generated for subsequent use in the methods and compositions herein. Preferably, monoclonal antibodies are utilized.

Methods of producing polyclonal antibodies are known to those of skill in the art. In brief, an antigen, analyte, or target site, such as a purified protein, a protein coupled to an appropriate carrier (e.g., GST, keyhole limpet hemanocyanin, etc.), or a protein incorporated into an immunization vector such as a recombinant vaccinia virus (see U.S. Pat. No. 4,722,848), is mixed with an adjuvant and animals are immunized with the mixture. The animal's immune response to the immunogen preparation is monitored by taking test bleeds and determining the titer of reactivity to the protein of interest. When appropriately high titers of antibody to the immunogen are obtained, blood is collected from the animal and antisera are prepared. Further fractionation of the antisera to enrich for antibodies reactive to the protein is performed where desired (See e.g., Coligan, Current Protocols in Immunology, Wiley/Greene, N Y (1991); and Harlow and Lane, Antibodies: A Laboratory Manual, Cold Spring Harbor Press, NY (1989)).

Monoclonal antibodies are prepared from hybrid cells secreting the desired antibody. Monoclonal antibodies are screened for binding to a protein from which the antigen was derived. Specific monoclonal and polyclonal antibodies will usually have an antibody binding site with an affinity constant for its cognate monovalent antigen at least between $10^6$-$10^7$, usually at least $10^8$, preferably at least $10^9$, more preferably at least $10^{10}$, and most preferably at least $10^{11}$ liters/mole.

A variety of immunoassay formats can be used to select antibodies (monoclonal or polyclonal) specifically reactive with a particular target site. For example, solid-phase ELISA immunoassays are routinely used to select monoclonal antibodies specifically immunoreactive with a protein. See Harlow and Lane, Antibodies, A Laboratory Manual, Cold Spring Harbor Publications, New York (1988), for a description of immunoassay formats and conditions that can be used to determine selective reactivity. Other exemplary and well known in the art immunoassay formats include competitive immunoassays, radioimmunoassays, Western blots, indirect immunofluorescent assays, and the like.

In some instances, it is desirable to prepare monoclonal antibodies from various mammalian hosts, such as mice, rodents, primates, humans, etc. A description of techniques for preparing such monoclonal antibodies is found in, e.g., Basic and Clinical Immunology, 9th ed., Stites et al., Eds. (Appleton & Lange Publications, San Mateo, Calif., 1998), and references cited therein; Harlow and Lane, Antibodies, A Laboratory Manual, Cold Spring Harbor Publications, New York (1988); Goding, Monoclonal Antibodies: Principles and Practice, 2nd ed. (Academic Press, New York, N.Y. 1986); and Kohler and Milstein, Nature, 256:495-497 (1975). Summarized briefly, this method proceeds by injecting an animal with an antigen (i.e., target site or analyte). The animal is then sacrificed and cells are taken from its spleen, which are fused with myeloma cells. The result is a hybrid cell or "hybridoma" that is capable of reproducing in vitro. The population of hybridomas is then screened to isolate individual clones, each of which secrete a single antibody species to the target site or antigen. In this manner, the individual antibody species obtained are the products of immortalized and cloned single B cells from the immune animal generated in response to a specific site recognized on the antigenic substance.

Other suitable techniques involve selection of libraries of recombinant antibodies in phage or similar vectors (see e.g., Huse et al., Science, 246:1275-1281 (1989); Ward et al., Nature, 341:544-546 (1989); and Vaughan et al., Nature Biotechnology, 14:309-314 (1996)). Alternatively, high avidity human monoclonal antibodies can be obtained from transgenic mice comprising fragments of the unrearranged human heavy and light chain Ig loci (i.e., minilocus transgenic mice). See Fishwild et al., Nature Biotech., 14: 845-851 (1996). Also, recombinant immunoglobulins may be produced. See Cabilly, U.S. Pat. No. 4,816,567; and Queen et al., Proc. Nat'l Acad. Sci., 86:10029-10033 (1989).

Finally, a fragment of an antibody protein which includes the antigen-binding portions but not the Fc section can be produced by treating whole antibodies with proteases that will specifically cleave off the Fc section.

Antibodies as described herein can be either inhibitory or activating. As the term is used herein in the context of TGF-β signaling and release, an inhibitory antibody inhibits the release of active TGF-β from the LRRC33-TGF-β prodomain-TGF-β complex. Such an antibody will recognize an epitope present on and formed by the ternary LRRC33-TGF-β prodomain-TGF-β complex. Binding of an antibody that recognizes an epitope present only on the LRRC33-TGF-β prodomain-TGF-β complex will tend to stabilize the complex and thereby prevent the release of active TGF-β. As the term is used herein in the context of TGF-β signaling and release, an "activating antibody" destabilizes the interaction of the LRRC33-TGF-β prodomain with TGF-β and promotes the release of active TGF-β.

To identify an antibody that stabilizes the LRRC33-TGF-β prodomain-TGF-β complex (i.e., an inhibitory antibody) antibodies or antigen binding fragment thereof can be screened for reactivity with LRRC33-TGF-β prodomain, LRRC33-TGF-β prodomain-TGF-β complex and TGF-β alone. Antibodies capable of binding to LRRC33-TGF-β prodomain-TGF-β complex but not LRRC3-TGF-β prodomain or TGF-β alone can stabilize the complex and prevent activation and release of active TGF-β (i.e., inhibiting or inactivating antibodies).

To identify an antibody that destabilizes the LRRC33-TGF-β prodomain-TGF-β complex (i.e., an activating antibody), one can screen for antibodies capable of binding LRRC33-TGF-β prodomain but not LRRC33-TGF-β prodomain-TGF-β complex or TGF-β alone. Such an antibody can promote activation and release of active TGF-β.

The identified antibodies can be further functionally validated as antagonist (prevents activation and release of active TGF-β) or agonist (promotes activation and release of active TGF-β) antibodies. Assays for measuring TGF-β activation and release are well known in the art. An exemplary assay of TGF-β activation and release can include, for example, incubating cells expressing the LRRC33-TGF-β prodomain-TGF-β complex with αvβ6 integrin bearing cells and candidate antibody for about 48 hr. After the treatment the cells are spun down and media supernatant is collected. The supernatant can be assayed for TGF-β release, for example, by immunoassay with antibodies specific for active TGF-β. TGF-β release assays are known in the art, for example, the TGF-β Release Co-culture Assay; bioprotocol; Vol 4, Iss 23. (2014), Pharmaceutically acceptable excipients that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol polyacrylates, waxes, polyethylene-polyoxypropylene-block polymers and polyethylene glycol.

TGF-β

"Active TGF-β" is a multifunctional cytokine protein that controls proliferation, differentiation and other functions in many cell types. For example, TGF-β has important roles in development, tissue repair, immune defense, inflammation and tumorigenesis (Roberts, 1998). Moreover, TGF-β is involved in the interactions between epithelia and the surrounding mesenchyme, promoting epithelial-to-mesenchymal transition (EMT) (Massague et al., 2000).

The transforming growth factor superfamily comprises at least 3 isoforms: TGF-β1, TGF-β2 and TGF-β3. Typically, TGF-β protein is synthesized as a precursor protein (Massague, 1990; Annes et al., 2003). The precursor protein is the full-length, native amino acid sequence or translation product and includes a signal sequence, N-terminal "pro-domain" region and C-terminal "TGF-β" region. The amino acid sequences of the "precursor protein" for each of the 3 isoforms and the pro-domain and TGF-β isoform derived therefrom, from different species, are known in the art and are publically available, e.g., in NCBI database.

The pro-domain (also denoted "prodomain" herein) or "latency associated peptide" of TGF-β refers to a polypeptide of ~250 amino acids, derived from the N-terminal region of the TGF-β precursor protein. As it relates to the methods and compositions described herein, the TGF-β pro-domain can bind non-covalently to the TGF-β growth factor, forming a latent TGF-β complex. Latent TGF-β is activated by processes involving binding by αv-containing integrins. The latent TGF-β complex maintains the TGF-β growth factor in a form or conformation that prevents interaction of the growth factor with such integrins, thereby preventing activation and release of the active TGF-β growth factor from the complex. TGF-β growth factor is a polypeptide of 110 amino acids, derived from the C-terminus of the TGF-β precursor protein.

As demonstrated herein, LRRC33 polypeptide forms a covalent complex with TGF-β prodomain via disulfide linkages. TGF-β growth factor in complex with TGF-β prodomain and LRRC33 is not available to interact with TGF-β receptors and does not exert an effect on receptor-bearing cells. "Active TGF-β" as used herein describes the TGF-β protein released from the pro-TGF-β or LRRC33-pro-TGF-β complex and capable of interacting with TGF-β receptors to exert effects on proliferation, differentiation, angiogenesis, etc., depending upon cellular and/or tissue context. Active TGF-β does not generally have a significant circulating concentration, but tends to act, rather, on cells or tissues close to its site of activation, e.g., in a paracrine or even autocrine manner. Thus, the interaction with LRRC33 demonstrated herein provides, through cell-specific expression of LRRC33, a way to effect the context-specific regulation of TGF-β-influenced processes. While LRRC33 expression is tightly regulated, it is also contemplated that LRRC33 or an analog or fragment thereof can be expressed from a tissue- or cell-type-specific promoter or regulatory sequence to effect expression in other tissues and thereby influence the activity of TGF-b in other cell or tissue contexts.

Exemplary sequences of human TGF-β precursor protein and residues corresponding to the signal peptide, pro-domain and TGF-β region are presented below.

The sequence of human precursor TGF-β1 is SEQ ID NO: 4

```
                                                        (SEQ ID NO: 4)
  1   mppsglrlll lllpllwllv ltpgrpaagl stcktidmel vkrkrieair gqilsklrla
 61   sppsqgevpp gplpeavlal ynstrdrvag esaepepepe adyyakevtr vlmvethnei
121   ydkfkgsths iymffntsel reavpepvll sraelrllrl klkveqhvel yqkysnnswr
181   ylsnrllaps dspewlsfdv tgvvrqwlsr ggeiegfrls ahcscdsrdn tlqvdingft
241   tgrrgdlati hgmnrpflll matpleraqh lqssrhrral dtnycfsste knccvrglyi
301   dfrkdlgwkw ihepkgyhan fclgpcpyiw sldtgyskvl alynqhnpga saapccvpqa
361   leplpivyyv grkpkveqls nmivrsckcs
```

(See UniProtKB/Swiss-Prot: P01137.2, the contents of which are incorporated herein in their entirety). Signal peptide, amino acids 1-29 of SEQ ID NO: 4; Pro-domain, amino acids 30-278 of SEQ ID NO: 4; TGF-β, amino acids 279-390 of SEQ ID NO: 4.

The sequence of human precursor TGF-β2 is SEQ ID NO: 5

```
                                                        (SEQ ID NO: 5)
  1   mhycvlsafl ilhlvtvals lstcstldmd qfmrkrieai rgqilsklkl tsppedypep
 61   eevppevisi ynstrdllqe kasrraaace rersdeeyya kevykidmpp ffpsenaipp
121   tfyrpyfriv rfdvsamekn asnlvkaefr vfrlqnpkar vpegrielyq ilkskdltsp
181   tqryidskvv ktraegewls fdvtdavhew lhhkdrnlgf kislhcpcct fvpsnnyiip
241   nkseelearf agidgtstyt sgdqktikst rkknsgktph lllmllpsyr lesqqtnrrk
301   kraldaaycf rnvgdncclr plyidfkrdl gwkwihepkg ynanfcagac pylwssdtqh
361   srvlslynti npeasaspcc vsqdleplti lyyigktpki eqlsnmivks ckcs
```

(See UniProtKB/Swiss-Prot: P61812.1, the contents of which are incorporated herein in their entirety). Signal peptide, amino acids 1-20 of SEQ ID NO: 5; Pro-domain, amino acids 21-302 of SEQ ID NO: 5; TGF-β, amino acids 303-414 of SEQ ID NO: 5.

The sequence of precursor human TGF-β3 is SEQ ID NO: 6.

```
                                                          (SEQ ID NO: 6)
  1    mkmhlgralv  vlallnfatv  slslstcttl  dfghikkkry  eairgqilsk  lrltsppept 61    vmthvpyqvl  alynstrell  eemhgereeg  ctgentesey  yakeihkfdm  iqglaehnel 121    avcpkgitsk  vfrfnvssve  knrtnlfrae  frvlrvpnps  skrnegriel  fqilrpdehi 181    akqryiggkn  lptrgtaewl  sfdvtdtvre  wllrresnlg  leisihcpch  tfqpngdile 241    nihevmeikf  kgvdneddhg  rgdlgrlkkg  kdhhnphlil  mmipphrldn  pgqggqrkkr 301    aldtnycfrn  leenccvrpl  yidfrqdlgw  kwvhepkgyy  anfcsgpcpy  lrsadtthst 361    vlglyntlnp  easaspccvp  qdlepltily  yvgrtpkveq  lsnmvvksck  cs
```

(See UniProtKB/Swiss-Prot: P10600.1, the contents of which are incorporated herein in their entirety). Signal peptide, amino acids 1-23 of SEQ ID NO: 6; Pro-domain, amino acids 24-300 of SEQ ID NO: 6; TGF-β, amino acids 301-412 of SEQ ID NO: 6.

TGF-β Related Disorders

The methods and compositions described herein are directed to modulation of the stability of the LRRC33-TGF-β prodomain-TGF-β complex, providing increased or decreased release of active TGF-β and subsequent increase or decrease in downstream TGF-β-mediated signaling and biological effects. Modulation includes the control or influence, directly or indirectly, of TGF-b signaling. By way of non-limiting examples, modulation can alternatively mean inhibit or stimulate, agonize or antagonize, hinder or promote, and strengthen or weaken. Accordingly, the methods and compositions described herein can find applications in prevention and treatment of TGF-β related disorders. "TGF-β-related disorders," as used herein, include both disorders related to aberrantly high levels of TGF-β signaling (e.g., hypertension, cancer, fibrosis), and disorders related to aberrantly low levels of TGF-β signaling (e.g., inflammatory diseases and immune related diseases). A non-limited list of disorders included within the definition of "TGF-β-related disorders" is hypertension (including pulmonary hypertension (e.g., Familial Primary Pulmonary Hypertension, or "FPPH")), cancer, fibrosis, wound healing, Marfan Syndrome, tumor metastasis, congenital heart disease, bone and muscle degenerative diseases, and Arterial Tortuosity Syndrome (ATS) (an autosomal recessive disorder characterized by tortuosity, elongation, stenosis and aneurysm formation in the major arteries owing to disruption of elastic fibers in the medial layer of the arterial wall), and neurodegenerative disorders.

Enhancing Immune Response—Among the effects of TGF-β on the immune system are inhibition of IL-2-receptor induction, IL-1-induced thymocyte proliferation, and blocking of gamma interferon-induced macrophage activation. Methods and compositions described herein can be directed towards inhibiting the release of active TGF-β, in order to enhance immune response in a subject in need thereof for e.g., for immunotherapy in a cancer patient or for enhancing macrophage activation or for treatment of disease associated with high levels of TGF-β activity, e.g., fibrosis.

TGF-β has at least two important roles in cancer. It inhibits the growth of many cells, so that loss of responsiveness to TGF-β (e.g., through mutation of receptor or SMAD proteins) results in uncontrolled proliferation. Second, it is highly immunosuppressive, so that tumor cells which no longer respond to TGF-β themselves up-regulate the expression of TGF-β to protect themselves from the immune system. Increased expression of TGF-β may also enhance the ability of the tumor cells to migrate to new sites via metastasis. Accordingly, provided herein are methods for inhibition of release of active TGF-β from the LRRC33-TGF-β prodomain-TGF-β complex. These methods and compositions can benefit subjects in need of enhanced immune activity or response, e.g., subjects suffering from cancer or chronic infection or in subjects suffering from, e.g., cardiovascular disease or neurodegenerative disease mediated by or involving TGF-β signaling.

Fibrosis and other related diseases—In one aspect, methods and compositions described herein can benefit subjects suffering from TGF-β mediated fibrosis and related disorders.

Because TGF-β plays a role in the development of fibrosis, provided herein is a method of prevention and/or treatment of fibrosis stimulated by TGF-β in pathology by administering to the site of potential fibrosis an amount of an agent that inhibits LRRC33-pro-TGF-β complex formation and/or release of active TGF-β from the LRRC33-pro-TGF-β complex, resulting in reduced fibrosis. "Reduced fibrosis," as used herein, is a statistically significant reduction in the level of abnormal formation of fibrous tissue. Fibrosis is determined, for example, by histological analysis. Fibrosis can also be quantitated in terms of tensile strength, and total protein and collagen content can also be used to monitor the level of abnormal formation of fibrous tissue in the presence and absence of treatment as described herein. In a clinical application, as but one example, a composition comprising an agent capable of preventing the release of active TGF-β from the LRRC33-TGF-β prodomain-TGF-β complex (for example, an antibody), can be used to impregnate bandages or as part of an ointment to be applied to wound areas for the purpose of enhancing wound healing or preventing fibrosis. A skilled clinician would be able to determine, more specifically, the amount of composition and length of treatment necessary to enhance wound healing or inhibit fibrosis. In related aspects, the methods and compositions as described herein also find utility in fibrosis-related disorders, such as fibroproliferative disorders including diabetic nephropathy, kidney disease, proliferative vitreoretinopathy, liver cirrhosis, biliary fibrosis, and myelofibrosis.

In some embodiments, the methods and compositions can be used for treatment of chronic infection. The promotion of macrophage activity by stabilization of LRRC33-TGF-β prodomain-TGF-β complexes with ensuing inhibition of active TGF-β release can facilitate clearance of infecting pathogens.

TGF-β can promote vascular abnormalities in cerebral blood vessels, possibly through its effects on TGF-β receptors on endothelial or smooth muscle cells and pericytes. TGF-β is upregulated in glial cells in response to brain lesioning, deafferentation, lesioning with excitatory amino acids, or transient forebrain ischemia in rodent brains and after stroke in human brains. Accordingly, in some embodiments, the methods and compositions disclosed herein can be used for treatment of neurodegenerative and vascular diseases.

Other conditions associated with excess TGF-β levels include idiopathic pulmonary fibrosis and myelofibrosis. To inhibit the effects of excess TGF-β activation and to slow the development of excess fibrous tissue, compositions disclosed herein that stabilize the LRRC33-TGF-β prodomain-TGF-β complex are contemplated for administration in these conditions.

The methods and compositions described herein can be used to treat collagen vascular disorders that are associated with overproduction of TGF-β. It is currently believed that there is an overproduction of TGF-β in collagen vascular disorders, such as progressive systemic sclerosis (PSS), polymyositis, scleroderma, dermatomyositis, eosinophilic fascitis, and morphea. Collagen vascular disorders may also be associated with the occurrence of Raynaud's syndrome. Among other effects, TGF-β overproduction can also be involved in interstitial pulmonary fibrosis, an end-stage lung disorder which is associated with autoimmune disorders such as systemic lupus erythematosus (SLE) and scleroderma (Deguchi, (1992) Ann. Rheum. Dis. 51:362-65); or it can be caused by chemical contact, allergies to dust and hay fever. A therapeutically effective amount of the compositions disclosed herein can be administered to counter or prevent release of active TGF-β to treat or prevent unwanted fibrosis.

Agents as described herein can be used in preventing overproduction of scarring in patients who are known to form keloids or hypertrophic scars. For example, compositions as described herein can be administered to prevent scarring or overproduction of scarring during healing of various types of wounds including surgical incisions and traumatic lacerations. The compositions can be applied, for example, to skin wounds before they are closed to help in healing without scar formation. Compositions disclosed herein can be placed in surgical abdominal wounds to help prevent adhesion formation which commonly occurs after that type of surgery. Local administration of the compositions described herein can counter local active TGF-β overproduction and prevent inappropriate activity of healing processes. TGF-β excess also has been reported in nasal polyposis, a condition characterized by multiple polyps (Ohno et al. (1992) J. Clin. Invest. 89: 1662-68). Compositions and methods disclosed herein can help lower active TGF-β levels and slow the hyperproliferation that results in polyps.

Methods and compositions described herein can also be applied or administered following coronary angioplasty, e.g., by placement of compositions that contain or release an agent that stabilizes the LRRC33-TGF-β prodomain-TGF-β complex along the inside of the affected arteries. According to Karas et al., ((1991) Clin. Cardiol. 14:791-801) restenosis or scarring and reclosing of arteries following coronary angioplasty is seen in approximately one-third of patients operated on. Because the fibrous network which ultimately develops into a scar normally accumulates rapidly, early administration of, for instance, an agent to prevent release of active TGF-β would reduce excess TGF-β in this area and slow excessive proliferation of connective tissue and restenosis. In this and other instances, extended release formulations including the agent can be beneficial.

TGF-β excess has also been observed in cardiac fibrosis after infarction and in hypertensive vasculopathy. To aid in proper healing without excess scar or fibrous tissue formation, agents as described herein can be administered in these conditions. TGF-β excess also has been observed in the tissues of patients receiving radiation therapy. Such tissue is characterized by excess connective tissue development, epithelial thinning and blood vessel occlusion associated with overgrowth of endothelial cells. In some embodiments, administration of an agent that stabilizes the LRRC33-TGF-β prodomain-TGF-β complex can inhibit TGF-b release and contribute to healing without excessive fibrosis.

Enhancing macrophage activation—TGF-β has the ability to inhibit cytokine-induced macrophage activation, and to suppress production of reactive oxygen and nitrogen intermediates. Accordingly, in one aspect, provided herein is a method of enhancing macrophage activation, the method comprising, contacting the macrophage with an agent stabilizes the LRRC33-TGF-β prodomain-TGF-β complex, such that it results in decreased release of active TGF-β, thereby relieving TGF-β-mediated macrophage suppression and enhancing macrophage activation. This approach is contemplated for use in any situation in which macrophage activation is of benefit, and particularly, for example in the treatment of cancer and chronic infection.

Activation (or re-activation) of macrophages is confirmed in vitro by various means involving measuring one or more of the various macrophage activities. For example, activated macrophages produce and secrete various cytokines, including Interleukin-6 (IL-6), Interleukin-1α and β (IL-1α, IL-1β), Tumor Necrosis Factor α, (TNF-α), Interleukin-8 (IL-8), Macrophage Inhibitory Peptide-1α (MIP-1α), Macrophage Inhibitory Peptide-1β (MIP-1β), and growth regulatory protein GRO. Activation can thus be determined by measuring the secretion of one or more of these cytokines, or by analyzing levels of transcription of mRNA for one or more of these cytokines. Moreover, macrophages can be observed in vitro (after activation either in vitro or in vivo) to determine effective phagocytosis of microbe organisms and/or production of TGF-β. Methods of measuring the production and release of reactive oxygen species are well-known in the art.

It is thus a matter of routine analysis to determine if the methods or compositions described herein facilitate activation (or re-activation) of macrophages/monocytes after incubation of the macrophages with a given agent in vitro. Similarly, it is also a matter of routine analysis to remove macrophages from a mammal that has been treated with such an agent, and determine if these macrophages are activated.

Cancer

One aspect of the technology relates to the methods of treating cancer comprising administering to a subject in need thereof an agent that stabilizes LRRC33-TGF-β prodomain complex.

"Cancer" is a hyperproliferation of cells that have lost normal cellular control, resulting in unregulated growth, lack of differentiation, local tissue invasion, and metastasis. Cancers are classified based on the histological type (e.g., the tissue in which they originate) and their primary site (e.g., the location of the body the cancer first develops). There are 6 major histological types of cancer: carcinoma, sarcoma, myeloma, leukemia, lymphoma, and mixed types (cancer that comprises various components within one histological type, or from two or more histological types).

A carcinoma is a cancer that originates in an epithelial tissue. Carcinomas account for approximately 80-90% of all cancers. Carcinomas can affect organs or glands capable of secretion (e.g., breasts, lung, prostate, colon, or bladder). There are two subtypes of carcinomas: adenocarcinoma, which develops in an organ or gland, and squamous cell carcinoma, which originates in the squamous epithelium. Adenocarcinomas generally occur in mucus membranes, and are observed as a thickened plaque-like white mucosa. They often spread easily through the soft tissue where they occur. Squamous cell carcinomas can originate from any region of the body. Examples of carcinomas include, but are not limited to, prostate cancer, colorectal cancer, microsatellite stable colon cancer, microsatellite instable colon cancer, hepatocellular carcinoma, breast cancer, lung cancer, small cell lung cancer, non-small cell lung cancer, lung adenocarcinoma, melanoma, basal cell carcinoma, squamous cell carcinoma, renal cell carcinoma, ductal carcinoma in situ, invasive ductal carcinoma.

Sarcomas are cancers that originate in supportive and connective tissues, for example bones, tendons, cartilage, muscle, and fat. Sarcoma tumors usually resemble the tissue in which they grow. Non-limiting examples of sarcomas include, Osteosarcoma or osteogenic sarcoma (originating from bone), Chondrosarcoma (originating from cartilage), Leiomyosarcoma (originating from smooth muscle), Rhabdomyosarcoma (originating from skeletal muscle), Mesothelial sarcoma or mesothelioma (originate from membranous lining of body cavities), Fibrosarcoma (originating from fibrous tissue), Angiosarcoma or hemangioendothelioma (originating from blood vessels), Liposarcoma (originating from adipose tissue), Glioma or astrocytoma (originating from neurogenic connective tissue found in the brain), Myxosarcoma (originating from primitive embryonic connective tissue), or Mesenchymous or mixed mesodermal tumor (originating from mixed connective tissue types).

Myelomas are cancers that originate in plasma cells of bone marrow. Non-limiting examples of myelomas include multiple myeloma, plasmacytoma and amyloidosis.

Leukemias (also known as "blood cancers") are cancers of the bone marrow, which is the site of blood cell production. Leukemia is often associated with the overproduction of immature white blood cells. Immature white blood cells do not function properly, rendering the patient prone to infection. Leukemia additionally affects red blood cells, and can cause poor blood clotting and fatigue due to anemia. Leukemia can be classified as being acute myeloid leukemia (AML), Chronic myeloid leukemia (CML), Acute lymphocytic leukemia (ALL), and Chronic lymphocytic leukemia (CLL). Examples of leukemia include, but are not limited to, Myelogenous or granulocytic leukemia (malignancy of the myeloid and granulocytic white blood cell series), Lymphatic, lymphocytic, or lymphoblastic leukemia (malignancy of the lymphoid and lymphocytic blood cell series), and Polycythemia vera or erythremia (malignancy of various blood cell products, but with red cells predominating).

Lymphomas develop in the glands or nodes of the lymphatic system (e.g., the spleen, tonsils, and thymus), which purifies bodily fluids and produces white blood cells, or lymphocytes. Unlike leukemia, lymphomas form solid tumors. Lymphoma can also occur in specific organs, for example the stomach, breast, or brain; this is referred to as extranodal lymphomas). Lymphomas are subclassified into two categories: Hodgkin lymphoma and Non-Hodgkin lymphoma. The presence of Reed-Sternberg cells in Hodgkin lymphoma diagnostically distinguishes Hodgkin lymphoma from Non-Hodgkin lymphoma. Non-limiting examples of lymphoma include Diffuse large B-cell lymphoma (DLBCL), Follicular lymphoma, Chronic lymphocytic leukemia (CLL), Small lymphocytic lymphoma (SLL), Mantle cell lymphoma (MCL), Marginal zone lymphomas, Burkitt lymphoma, hairy cell leukemia (HCL). In one embodiment, the cancer is DLBCL or Follicular lymphoma.

In one embodiment, the cancer is a solid tumor. Non-limiting examples of solid tumors include Adrenocortical Tumor, Alveolar Soft Part Sarcoma, Chondrosarcoma, Colorectal Carcinoma, Desmoid Tumors, Desmoplastic Small Round Cell Tumor, Endocrine Tumors, Endodermal Sinus Tumor, Epithelioid Hemangioendothelioma, Ewing Sarcoma, Germ Cell Tumors (Solid Tumor), Giant Cell Tumor of Bone and Soft Tissue, Hepatoblastoma, Hepatocellular Carcinoma, Melanoma, Nephroma, Neuroblastoma, Non-Rhabdomyosarcoma Soft Tissue Sarcoma (NRSTS), Osteosarcoma, Paraspinal Sarcoma, Renal Cell Carcinoma, Retinoblastoma, Rhabdomyosarcoma, Synovial Sarcoma, and Wilms Tumor. Solid tumors can be found in bones, muscles, or organs, and can be sarcomas or carinomas.

In one embodiment, the cancer is melanoma or colon cancer. Where these are both carcinoma, it is reasonable to expect that the methods and compositions described herein can be used to treat other carcinomas. Thus, in one embodiment, it is contemplated that cancers of similar types or origin (e.g., carinomas) could be treated using methods and compositions described herein. An agent that is effective in treating a particular cancer is likely to be effective in treating other tumors within the same histological type. Moreover, it is contemplated that to the extent that TGFβ signaling is involved in the continued growth or metastasis of the cancer, tumors or cancers with differing origins (e.g., sarcomas, or myeloma) can additionally be treated using the methods and compositions described herein.

In one embodiment, methods and compositions described herein are used to inhibit metastasis. As used herein, "metastasis" refers to the development of secondary malignant growths (secondary tumors) at a distance from the primary malignant growth (primary tumor). One skilled in the art can determine if a primary growth has metastasized, for example histologically. A tumor with hepatocellular carcinoma characteristics found outside the liver, for example, is a metastatic tumor. Certain cancers metastasize more frequently to certain sites than others. For example, breast cancer commonly is found to metastasize to the lungs or the brain, among other sites. Common sites for secondary tumors for specific cancers are known in the art. One skilled in the art can determine if a cancer has metastasized. In one embodiment, methods and compositions as described herein are used to inhibit invasion. As used herein, "invasion" refers to the capacity for a cell to become motile and infiltrate neighboring tissues. In another embodiment, methods and compositions described herein are used to inhibit extravasation. As used herein, "extravasation" refers to the movement of cancer cell out of the circulatory system and into tissues to for metastases.

It is demonstrated herein that tumors that are resistant to anti-PD-1 or anti-PD-L1 therapies become sensitive to these checkpoint inhibitor therapies when treated with an agent that stabilizes LRRC33-TGF-β-prodomain. It would be expected that treatment with an agent that stabilizes LRRC33-TGF-β-prodomain would be effective in rendering other anti-PD-1-resistant or anti-PD-L1-resistant tumors sensitive to anti-PD-1 therapies. Cancers that are susceptible to, and treated with, anti-PD-1 therapy include, but are not limited to melanoma, non-small cell lung cancer, kidney cancer, bladder cancer, head and neck cancer, gastric cancer, colon cancer, breast cancer, esophageal cancer, and Hodgkin lymphoma. It is contemplated herein that treatment with agents that stabilize LRRC33-TGF-β-prodomain would be effective to render other checkpoint inhibitor-resistant tumors sensitive to checkpoint inhibitor therapies.

Immunosuppression and Inhibiting Macrophage Activation

Since the methods and compositions disclosed herein are directed towards modulating the stability of LRRC33-TGF-β prodomain-TGF-β complex, such methods can also be applied to destabilize such complex, resulting in increased release of active TGF-β from the complex. In another aspect, the methods and compositions described herein can promote release of active TGF-β in order to promote TGF-β-mediated immunosuppression in a subject suffering from, e.g., chronic inflammation, inflammatory disease, or autoimmune disease, or to promote TGF-β mediated inhibition of macrophage activation.

In this aspect one can administer an agent that destabilizes an LRRC33-TGF-β prodomain-TGF-β complex to promote release of active TGF-β from the complex and promote immunosuppression. Examples of conditions treatable in this manner include, but are not limited to, include, e.g., organ allograft rejection and autoimmune diseases, such as systemic lupus erythematosus, rheumatoid arthritis, scleroderma dermatomyositis, polymyositis, unclassified connective diseases, autoimmune hemolytic anemia, idiopathic thrombocytopenic purpura, autoimmune thyroiditis, polyarteritis nodosum, glomerulonephritis, uveitis, etc.

Inflammatory disorders include inflammation-mediated maladies, whether or not also immune mediated. Thus, such diseases include those caused by the release of toxic oxygen products from phagocytes in inflammatory lesions. Examples include rheumatoid arthritis, adult respiratory distress syndrome, and septic shock.

Dosage and Administration

For the clinical use of the methods and uses described herein, administration of the compositions comprising agents that modulate LRRC33-TGF-β prodomain-TGF-β interactions, inhibitors of TGF-β release (e.g., agents that stabilize LRRC33-TGF-β prodomain-TGF-β complex) and potentiators of TGF-β release (e.g., agents that destabilize LRRC33-TGF-β prodomain-TGF-β complex) can include formulation into pharmaceutical compositions or pharmaceutical formulations for parenteral administration, e.g., intravenous; mucosal, e.g., intranasal; ocular, or other mode of administration. In some embodiments, the agents that modulate LRRC33-TGF-β prodomain-TGF-β complex can be administered along with any pharmaceutically acceptable carrier compound, material, or composition which results in an effective treatment in the subject. Thus, a pharmaceutical formulation for use in the methods described herein can contain an agent that modulates LRRC33-TGF-β prodomain-TGF-β complex as described herein in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of an agent that modulates LRRC33-TGF-β prodomain-TGF-β complex. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) excipients, such as cocoa butter and suppository waxes; (8) oils, such as peanut oil, cottonseed oil, safflower oil, sesame oil, olive oil, corn oil and soybean oil; (9) glycols, such as propylene glycol; (10) polyols, such as glycerin, sorbitol, mannitol and polyethylene glycol (PEG); (11) esters, such as ethyl oleate and ethyl laurate; (12) agar; (13) buffering agents, such as magnesium hydroxide and aluminum hydroxide; (14) alginic acid; (15) pyrogen-free water; (16) isotonic saline; (17) Ringer's solution; (19) pH buffered solutions; (20) polyesters, polycarbonates and/or polyanhydrides; (21) bulking agents, such as polypeptides and amino acids (22) serum components, such as serum albumin, HDL and LDL; (23) C2-C12 alcohols, such as ethanol; and (24) other non-toxic compatible substances employed in pharmaceutical formulations. Release agents, coating agents, preservatives, and antioxidants can also be present in the formulation. The terms such as "excipient", "carrier", "pharmaceutically acceptable carrier" or the like are used interchangeably herein.

An agent that modulates LRRC33-TGF-β prodomain-TGF-β complex or the release of active TGF-β from such complex as described herein can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (7) nasally. Additionally, an agent that modulates LRRC33-TGF-β prodomain-TGF-β complex or the release of active TGF-β can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960.

Further embodiments of the formulations and modes of administration of the compositions comprising an agent that modulates LRRC33-TGF-β prodomain-TGF-β complex or the release of active TGF-β that can be used in the methods described herein are described below.

Parenteral Dosage Forms

Parenteral dosage forms of an agent that modulates LRRC33-TGF-β prodomain-TGF-β complex or the release of active TGF-β can also be administered to a subject by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Aerosol Formulations

Where therapeutically indicated, an agent that modulates LRRC33-TGF-β prodomain-TGF-β complex or the release of active TGF-β can be packaged in a pressurized aerosol container together with suitable propellants, for example, hydrocarbon propellants like propane, butane, or isobutane with conventional adjuvants. An agent that modulates LRRC33-TGF-β prodomain-TGF-β complex or the release of active TGF-β can also be administered in a non-pressurized form such as in a nebulizer or atomizer. An agent that modulates LRRC33-TGF-β prodomain-TGF-β complex or the release of active TGF-β can also be administered directly to the airways in the form of a dry powder, for example, by use of an inhaler.

Suitable powder compositions include, by way of illustration, powdered preparations of an agent that modulates LRRC33-TGF-β prodomain-TGF-β complex or the release of active TGF-β described herein can be thoroughly intermixed with lactose, or other inert powders acceptable for intrabronchial administration. The powder compositions can be administered via an aerosol dispenser or encased in a breakable capsule which can be inserted by the subject into a device that punctures the capsule and blows the powder out in a steady stream suitable for inhalation. The compositions can include propellants, surfactants, and co-solvents and can be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic and diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

The formulations of an agent that modulates LRRC33-TGF-□ prodomain-TGF-□ complex or the release of active TGF-β described herein can further encompass anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprise a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Controlled and Delayed Release Dosage Forms

In some embodiments of the aspects described herein, an agent that modulates LRRC33-TGF-β prodomain-TGF-β complex or the release of active TGF-β can be administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound of formula (I)'s onset of action, duration of action, plasma levels within the therapeutic window, and peak blood levels. In particular, controlled- or extended-release dosage forms or formulations can be used to ensure that the maximum effectiveness of an agent that modulates LRRC33-TGF-β prodomain-TGF-β complex or the release of active TGF-β is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with an agent that modulates LRRC33-TGF-β prodomain-TGF-β complex or the release of active TGF-β described herein. Examples include, but are not limited to, those described in U.S. Pat. Nos. 3,845,770; 3,916,899; 3,536,809; 3,598,123; 4,008,719; 5,674,533; 5,059,595; 5,591, 767; 5,120,548; 5,073,543; 5,639,476; 5,354,556; 5,733,566; and 6,365,185, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, DUOLITE® A568 and DUOLITE® AP143 (Rohm&Haas, Spring House, Pa. USA).

In some embodiments of the methods described herein, an agent that modulates LRRC33-TGF-β prodomain-TGF-β complex or the release of active TGF-β for use in the methods described herein is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred when the disorder occurs continuously in the subject, for example where the subject has continuous or chronic symptoms of a viral infection. Each pulse dose can be reduced and the total amount of an agent that modulates LRRC33-TGF-β prodomain-TGF-β complex or the release of active TGF-β described herein administered over the course of treatment to the subject or patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals can be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

Efficacy

The efficacy of compositions as described herein in, e.g., the treatment of a condition described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g., tumor size or inflammatory cytokine levels. Efficacy can also be measured by a failure of an individual to worsen as assessed by hospitalization, or need for medical interventions (i.e., progression of the disease is halted). Methods of measuring these indicators are known to those of skill in the art and/or are described herein.

Efficacy can be assessed in animal models of a condition described herein, for example, a mouse model of cancer, a pathogenic infection model, or an appropriate animal model of autoimmune or inflammatory disease, as the case may be. When using an experimental animal model, efficacy of treatment is evidenced when a statistically significant change in a marker is observed, e.g. decrease in tumor size or change in inflammatory cytokines.

Effective treatment can include, for example, a reduction in tumor size, a reduction the rate of tumor growth, a reduction in metastasis (for example, a reduction of metastatic nodules), and/or a reduction of metastatic melanoma nodules on the lung in a subject.

In some embodiments, the methods and compositions described herein reduce the in a subject. In some embodiments, the methods and compositions described herein reduce the rate of growth for a tumor in a subject. In some embodiments, the methods and compositions described herein reduce number of metastatic nodules a subject. In some embodiments, the methods and compositions described herein reduce number of metastatic melanoma nodules on the lung in a subject.

Some embodiments of the technology described herein can be defined according to any of the following numbered paragraphs:

1. A method of preventing release of active TGF-β from an LRRC33-TGF-β prodomain-TGF-β complex, the method comprising contacting a cell that comprises an LRRC33-TGF-β prodomain-TGF-β complex, with an agent that stabilizes the LRRC33-TGF-β prodomain-TGF-β complex, wherein the stabilizing prevents release of active TGF-β from the LRRC33-TGF-β prodomain-TGF-β complex.
2. The method of paragraph 1, wherein the agent comprises an antibody or antigen-binding fragment thereof.
3. The method of paragraph 2, wherein the antibody or antigen-binding fragment thereof specifically binds an LRRC33 epitope.
4. The method of paragraph 2, wherein the antibody or antigen-binding fragment thereof specifically binds an epitope comprised only by the LRRC33-TGF-β prodomain-TGF-β complex.
5. The method of paragraph 1, wherein the cell is a macrophage.
6. A method of promoting macrophage activity, the method comprising contacting a macrophage with an agent that stabilizes the interaction of an LRRC33-TGF-β prodomain complex with TGF-β.
7. The method of paragraph 6, wherein the agent comprises an antibody or antigen-binding fragment thereof.
8. The method of paragraph 7, wherein the antibody or antigen-binding fragment thereof specifically binds an LRRC33 epitope.
9. The method of paragraph 7, wherein the antibody or antigen-binding fragment thereof specifically binds an epitope comprised only by the LRRC33-TGF-β prodomain-TGF-β complex.
10. A method of enhancing immune activity in a subject in need thereof, the method comprising, administering an agent that stabilizes the interaction of an LRRC33-TGF-β prodomain complex with TGF-β, thereby enhancing immune activity in the subject.
11. The method of paragraph 10, wherein the agent comprises an antibody or antigen-binding fragment thereof.

12. The method of paragraph 11, wherein the antibody or antigen-binding fragment thereof specifically binds an epitope on LRRC33.
13. The method of paragraph 11, wherein the antibody or antigen-binding fragment thereof specifically binds an epitope comprised only by the LRRC33-TGF-β prodomain-TGF-β complex.
14. The method of paragraph 10, wherein the subject has cancer or a chronic infection.
15. The method of paragraph 10, further comprising administering a checkpoint inhibitor.
16. The method of paragraph 15, wherein the checkpoint inhibitor is selected from the group consisting of: an anti-PD-1 agent, an anti-PDL-1 agent, an anti-CTLA4 agent, and an anti-TIM3 agent.
17. The method of paragraph 15, wherein the anti-PD-1 agent is anti-PD-1 antibody clone RMP1-14.
18. A method of promoting cell surface clearance or endocytosis of an LRRC33-TGF-β prodomain-TGF-β complex from a cell, the method comprising contacting the cell with an agent that specifically binds LRRC33.
19. The method of paragraph 18, wherein the agent comprises an antibody.
20. The method of paragraph 19, wherein the antibody specifically binds LRRC33.
21. The method of paragraph 20, wherein the antibody specifically binds the ectodomain of LRRC33.
22. A method of promoting cell surface clearance or endocytosis of an LRRC33-TGF-β prodomain-TGF-β complex from a cell, the method comprising contacting the cell with an agent that specifically binds an LRRC33-TGF-β prodomain-TGF-β complex.
23. The method of paragraph 22, wherein the agent comprises an antibody.
24. The method of paragraph 23, wherein the antibody specifically binds an epitope comprised only by the LRRC33-TGF-β prodomain-TGF-β complex.
25. A method of promoting release of active TGF-β from an LRRC33-TGF-β prodomain-TGF-β complex, the method comprising contacting a cell that comprises an LRRC33-TGF-β prodomain-TGF-β complex, with an agent that destabilizes the LRRC33-TGF-β prodomain-TGF-β complex, wherein destabilization of the complex promotes release of active TGF-β from the LRRC33-TGF-β prodomain-TGF-β complex.
26. The method of paragraph 25, wherein the agent is an antibody or an antigen binding fragment thereof
27. The method of paragraph 26, wherein the antibody or antigen-binding fragment thereof binds an LRRC33 polypeptide epitope.
28. The method of paragraph 26, wherein the antibody or antigen-binding fragment thereof specifically binds an epitope comprised only by the LRRC33-TGF-β prodomain complex.
29. The method of paragraph 28, wherein the cell is a macrophage.
30. A method of promoting immunosupression in a subject in need thereof, the method comprising, administering an agent that destabilizes an LRRC33-TGF-β prodomain-TGF-β complex, wherein the administering promotes release of active TGF-β from the complex, thereby promoting immunosuppression.
31. The method of paragraph 30, wherein the agent is an antibody or an antigen-binding fragment thereof.
32. The method of paragraph 31, wherein the antibody or an antigen binding fragment thereof specifically binds an LRRC33 polypeptide epitope.
33. The method of paragraph 30, wherein the antibody or antigen-binding fragment thereof specifically binds an epitope comprised only by the LRRC33-TGF-β prodomain complex.
34. The method of paragraph 30, wherein the subject has a disease or disorder selected from the group consisting of chronic inflammation, autoimmune disease or fibrosis.
35. The method of paragraph 30, further comprising administering a checkpoint inhibitor.
36. The method of paragraph 35, wherein the checkpoint inhibitor is selected from the group consisting of: an anti-PD-1 agent, an anti-PDL-1 agent, an anti-CTLA4 agent, an anti-LAG3 agent, and an anti-TIM3 agent.
37. The method of paragraph 35, wherein the anti-PD-1 agent is anti-PD-1 antibody clone RMP1-14.
38. A composition comprising a fragment of an LRRC33 polypeptide that binds to TGF-β prodomain.
39. The composition of paragraph 38, wherein the fragment of LRRC33 comprises the LRRC33 ectodomain.
40. An isolated nucleic acid sequence encoding the LRRC33 polypeptide fragment of paragraph 38.
41. The isolated nucleic acid sequence of paragraph 40, wherein the isolated nucleic acid sequence is operably linked to a regulatory element.
42. The isolated nucleic acid sequence of paragraph 41, wherein the regulatory element permits tissue or cell specific expression of the nucleic acid sequence encoding the fragment of an LRRC33 polypeptide.
43. A vector comprising an isolated nucleic acid sequence of any one of paragraphs 40-42.
44. A cell comprising a nucleic acid of any one of paragraphs 40-42 or a vector of paragraph 43.
45. The cell paragraph 44, wherein the fragment of an LRRC33 polypeptide is expressed on its surface.
46. The cell of paragraph 44, wherein the cell is a mammalian cell.
47. The cell of paragraph 44, wherein the cell is a human cell.
48. An antibody or an antigen-binding fragment thereof comprising the variable heavy chain sequence of SEQ ID NO: 2, wherein antibody specifically binds to an LRRC33 polypeptide.
49. An antibody or an antigen-binding fragment thereof comprising the variable light chain sequence of SEQ ID NO: 3, wherein the antibody specifically binds to an LRRC33 polypeptide.
50. An antibody or an antigen-binding fragment thereof comprising the variable heavy chain sequence of SEQ ID NO: 2 and the variable light chain sequence of SEQ ID NO: 3, wherein the antibody specifically binds to an LRRC33 polypeptide.
51. The antibody or an antigen-binding fragment of any one of paragraphs 48-50, wherein the LRRC33 polypeptide has the amino acid sequence SEQ ID NO: 1.
52. The antibody or an antigen-binding fragment of any one of paragraphs 48-51, wherein the antigen-binding fragment is an Fab, Fab', F(ab')2, Fv or single chain Fv (ScFv).
53. A composition comprising a fragment of an LRRC33 polypeptide that binds TGF-β prodomain, bound to a TGF-β prodomain polypeptide.
54. The composition of paragraph 53, wherein the LRRC33 polypeptide fragment is covalently linked to the TGF-β prodomain polypeptide.

55. The composition of paragraph 54 wherein the LRRC33 polypeptide fragment is covalently linked to the TGF-β prodomain polypeptide via disulfide bonds.
56. The composition of any one of paragraphs 53-55, further comprising an adjuvant.
57. A method of treating cancer, the method comprising administering to subject in need thereof an agent that stabilizes LRRC33-TGF-β prodomain complex and a checkpoint inhibitor.
58. The method of paragraph 57, wherein the agent comprises an antibody or antigen-binding fragment thereof.
59. The method of paragraph 58, wherein the antibody or antigen-binding fragment thereof specifically binds an epitope on LRRC33.
60. The method of paragraph 58, wherein the antibody or antigen-binding fragment thereof specifically binds an epitope comprised only by the LRRC33-TGF-β prodomain-TGF-β complex.
61. The method of paragraph 57, wherein the cancer is a carcinoma.
62. The method of paragraph 57, wherein the cancer is melanoma or colon cancer.
63. The method of paragraph 57, wherein the cancer is resistant to anti-PD-1 agent.
64. The method of paragraph 57, wherein the checkpoint inhibitor is selected from the group consisting of: an anti-PD-1 agent, an anti-PDL-1 agent, an anti-CTLA4 agent, an anti-LAG3 agent, and an anti-TIM3 agent.
65. The method of paragraph 64, wherein the anti-PD-1 agent is anti-PD-1 antibody clone RMP1-14.
66. A method of treating melanoma or colon cancer, the method comprising administering to subject in need thereof an agent that stabilizes LRRC33-TGF-β prodomain complex and a checkpoint inhibitor.
67. A method of treating melanoma or colon cancer, the method comprising administering to subject in need thereof an agent that stabilizes LRRC33-TGF-β prodomain complex and anti-PD-1 agent.
68. A method of treating melanoma or colon cancer, the method comprising administering to subject in need thereof an agent that stabilizes LRRC33-TGF-β prodomain complex and anti-PD-1 antibody clone RMP1-14.
69. A composition comprising an agent that stabilizes LRRC33-TGF-β prodomain complex and a checkpoint inhibitor.
70. The composition of paragraph 69, wherein the agent comprises an antibody or antigen-binding fragment thereof.
71. The composition of paragraph 70, wherein the antibody or antigen-binding fragment thereof specifically binds an epitope on LRRC33.
72. The composition of paragraph 70, wherein the antibody or antigen-binding fragment thereof specifically binds an epitope comprised only by the LRRC33-TGF-β prodomain-TGF-β complex.
73. The composition of paragraph 69, wherein the checkpoint inhibitor is selected from the group consisting of: an anti-PD-1 agent, an anti-PDL-1 agent, an anti-CTLA4 agent, an anti-LAG3 agent, and an anti-TIM3 agent.
74. The composition of paragraph 73, wherein the anti-PD-1 agent is anti-PD-1 antibody clone RMP1-14.
75. A composition comprising an agent that stabilizes LRRC33-TGF-β prodomain complex and an anti-PD-1 agent.
76. A composition comprising an agent that stabilizes LRRC33-TGF-β prodomain complex and anti-PD-1 antibody clone RMP1-14.
77. A composition comprising any of the antibodies or antigen binding fragments of paragraphs 42-46 and a checkpoint inhibitor.
78. A composition comprising any of the antibodies or antigen binding fragments of paragraphs 42-46 and an anti-PD-1 agent.
79. A composition comprising any of the antibodies or antigen binding fragments of paragraphs 42-46 and anti-PD-1 antibody clone RMP1-14.
80. The composition of any of paragraphs 38 or 39, further comprising a checkpoint inhibitor.
81. The composition of any of paragraphs 38 or 39, further comprising an anti-PD-1 agent.
82. The composition of any of paragraphs 38 or 39, further comprising anti-PD-1 antibody clone RMP1-14.
83. The composition of any of paragraphs 53-55, further comprising a checkpoint inhibitor.
84. The composition of any of paragraphs 53-55, further comprising an anti-PD-1 agent.
85. The composition of any of paragraphs 53-55, further comprising anti-PD-1 antibody clone RMP1-14.
86. The composition of any of paragraphs 69-85, further comprising an adjuvant.
87. Use of any of the compositions from paragraphs 69-86 for the treatment of cancer.
88. Use of any of the compositions from paragraphs 69-86 for the treatment of carcinoma.
89. Use of any of the compositions from paragraphs 69-86 for the treatment of melanoma or colon cancer.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The technology described herein is further illustrated by the following examples which in no way should be construed as being further limiting.

Example 1

Materials and Methods

Figures 9A, 9B:
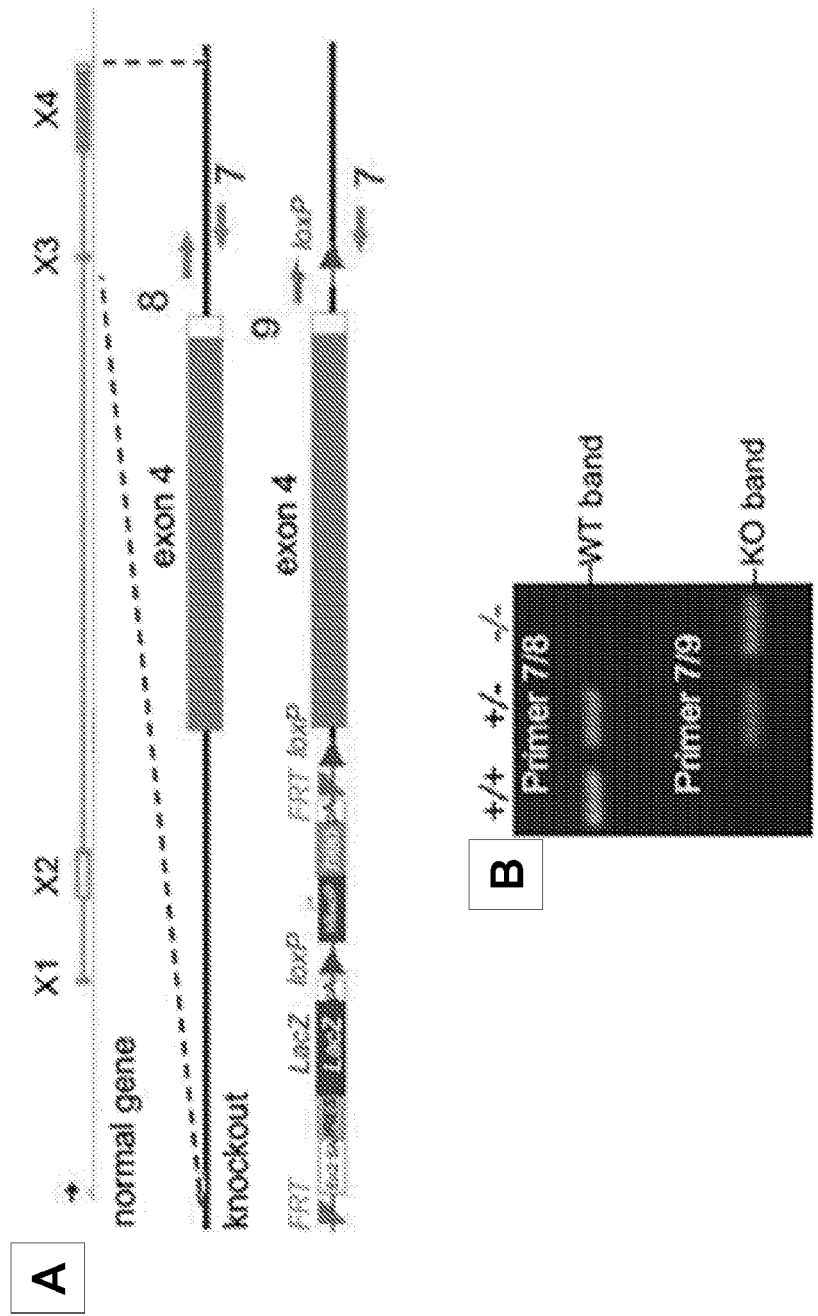
FIGS. 9A and 9B show Lrrc33−/− mice genotyping. (A) Lrrc33 knockout construct. (B) Genotyping results show the WT band and knockout (KO) band.

Mice. C57BL/6N embryonic stem (ES) cells with the Lrrc33 gene inactivated by homologous recombination (FIG. 9A) from the knockout mouse project (KOMP) were injected into C57BL/6N blastocysts. C57BL/6N Lac33$^{+/-}$ mice were fertile and do not show any pathological abnormalities and breed well and used to obtain the Lac33$^{-/-}$ mice. Progeny mice were intercrossed at least six generations before all experimental procedures. Genotyping uses two sets of PCR primers (FIG. 9A). Mice were routinely genotyped by PCR using the following primers (FIG. 9B): primer 7: 5'-GAA CCC AGG ACA TCT GGA AA-3' (SEQ ID NO: 7), primer 8: 5'-TGA GTG ACA GCA TCC TGG AG-3' (SEQ ID NO: 8), primer 9: 5'-GCG CAA CGC AAT TAA TGA TA-3'(SEQ ID NO: 9). All animal experiments were approved by the Institutional Animal Care and Use Committee (IACUC) at Harvard Medical School.

Generation of Anti-LRRC33 Monoclonal Antibody (mAb).

Figure 8A:
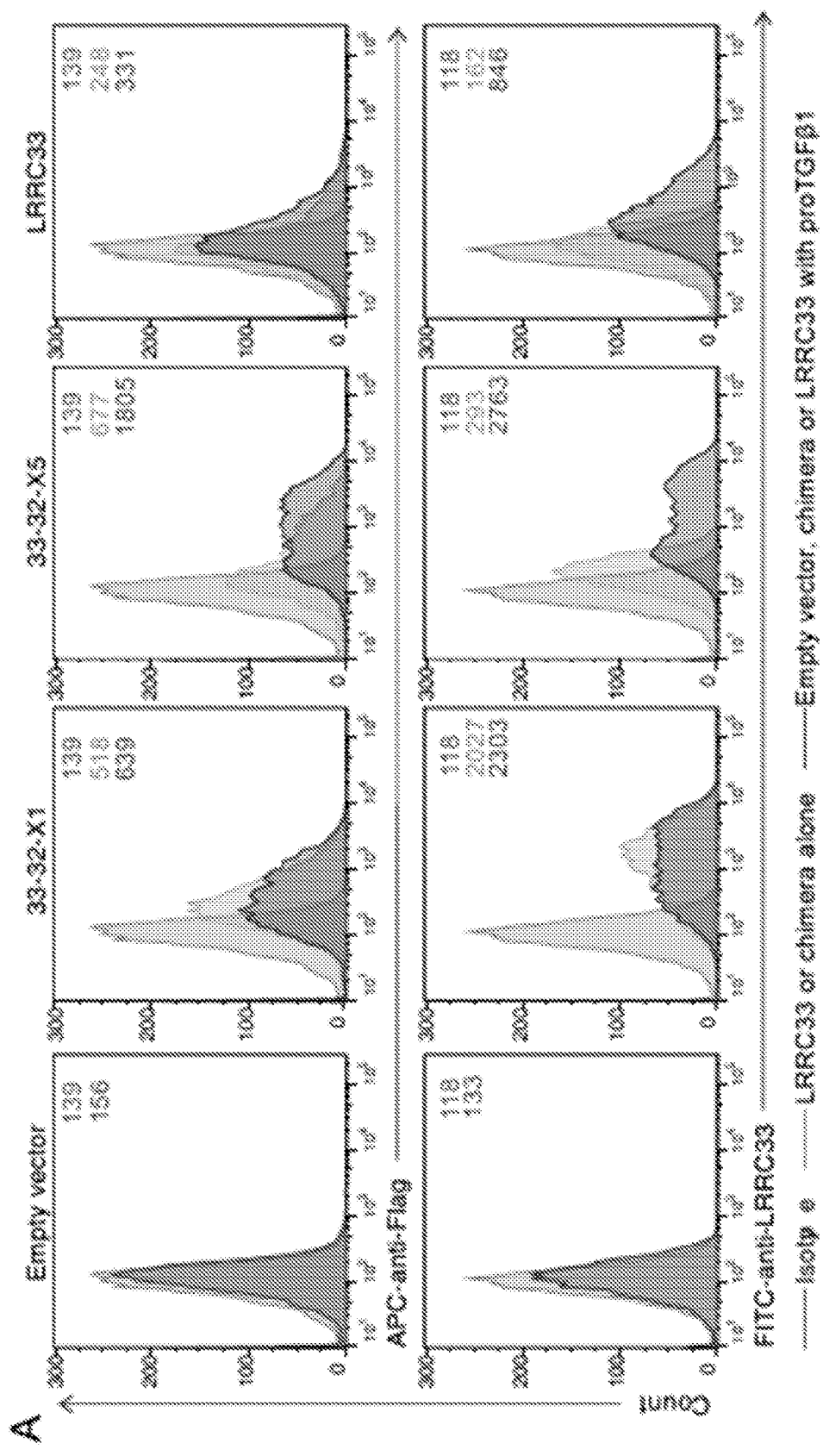
FIGS. 8A-8C shows anti-LRRC33 antibody characterization. (A) LRRC33, chimera 33-32-X1 and 33-32-X5 are detected on cell surface of 293T transfectants when co-expressed with proTGF-β1 by using anti-LRRC33 antibody. Cell surface expression of FLAG-LRRC33, FLAG-33-32-X1, and FLAG-33-32-X5 were measured using FACS. Numbers show the MFI (mean fluorescence intensity). (B, C) The specificity of anti-LRRC33 antibody. L1.2 transfectant lysates (B) and 293T transfectant lysates (C) were immunoprecipitated (IP) by anti-LRRC33 antibody, subjected to 10% reducing SDS-PAGE and blotted (IB) as indicated.
Figures 8B, 8C:
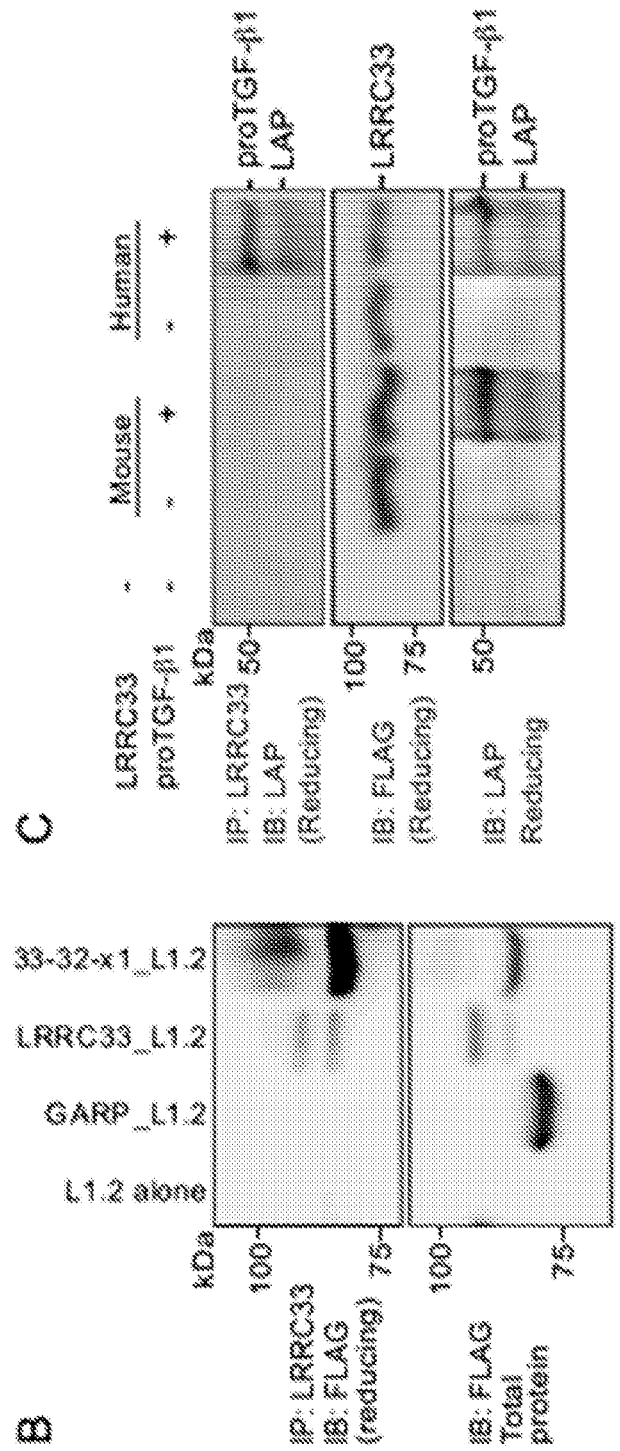

Anti-LRRC33 mAb was generated by immunizing Lac33$^{-/-}$ mice with L1.2 cells that stably express the 33-32-X1 chimera on the cell surface. Hybridoma supernatants were screened by immunofluorescence flow cytometry (FACS) and an LRRC33 positive hybridoma was identified. This anti-LRRC33 mAb only recognizes human LRRC33, not GARP, in L1.2 transfectants by immunoprecipitates (IP) (FIG. 8B, line 2, 3). And this anti-LRRC33 mAb can also recognizes human LRRC33 complexed with pro-TGF-β1 from 293T cell lysates of co-transfectants by immunoprecipitates (IP) (FIG. 8C, line 5) and FACS (FIG. 8A). However, this antibody does not cross-react with mouse LRRC33 complexes (FIG. 8C, line 3).

Plasmids

Transfection-ready, untagged human GARP and LRRC33 cDNA was purchased from Origene (Rockville, Md.). Human TGF-β1 cDNA was provided by Katri Koli (University of Helsinki, Helsinki, Finland) GARP, LRRC33, 33-32-X1, 33-32-X5 and proTGF-β1 were subcloned into a modified pLEXm vector with a FLAG tag at the N-terminus respectively. LRRC33 was also subcloned into pcDNA3.1 myc-his (Invitrogen). Human LTBP1 cDNA was provided by Vesna Todorovic (New York University).

Cell Culture and Transfection 293T cells were transfected with the indicated plasmid using Lipofectamine 2000 (Life Technologies) according to manufacturer's instructions. After 48 hours of transfection, cells were collected and lysed in IP lysis buffer (50 mM Tris pH7.4, 150 mM NaCl, 2 mM EDTA, 1% NP-40), which was supplemented with a protease inhibitor cocktail (Roche) and subjected to western blot analysis or were used for immunoprecipitation with the indicated antibody. Performed as described previously {Wang et al, 2012}. L1.2 cells were transfected with indicated plasmid using electroporation. For microglia cell culture, freshly isolated microglia (at age 3 weeks) were cultured in 6-well ($2 \times 10^5$ cells per well in 2 ml) poly-D-lysine-coated plates, and grown in serum free microglia culture medium: Neurobasal medium with B-27 supplements (Thermo Fisher), 5 ug/ml insulin, 2 mM L-glutamine, 1 mM sodium pyruvate, 5 μg/ml N-acetyl cysteine (NAC), 100 U/ml penicillin, 100 mg/ml streptomycin, 10 μM thyroxine, 1×SATO (100 μg/ml transferrin, 100 μg/ml BSA, 16 μg/ml putrescine, 60 ng/ml progesterone, 40 ng/ml sodium selenite) (sigma) and mouse recombinant carrier free CSF 10 ng/ml (R&D Systems) at 37° C., 5% $CO^2$. Cells were cultured for at least 5 d without changing medium.

Cells Isolation and Sorting

For peritoneal macrophages, WT and Lrrc33$^{-/-}$ mice were injected with 1 ml of 4% thioglycollate medium and 4 days later peritoneal cells were collected by lavage using 10 ml PBS. Cells were allowed to adhere for 24 hours. Adherent cells were collected, counted and co-cultured with TMLC for luciferase assay. For microglia, WT and Lrrc33$^{-/-}$ mice were transcardially perfused with ice-cold phosphate-buffer saline (PBS), and gently scoop the brain out of the skull by starting at the olfactory bulb. Single cell suspensions were prepared by dounce homogenization or papain (Worthington) digestion and centrifuged over a 37% Percoll (GE Healthcare). Resident microglia were sorted with combination of CD45 (APC-CD45.2, clone 30-F11, Biolegend), Mac1 (PE-cy7-Mac 1, clone M1/70, Biolegend) and CD39 (PE-CD39, clone 5F2, Biolegend) antibodies followed by total RNA isolation and gene expression profiling. Resident microglia also purified by immune-panning method {Zhang, 2014 #24481} with anti-CD45 antibody (Biolegend).

FACS

293T, L1.2 transfectant, leukemia cell lines and brain cells were stained and analyzed as described previously {Wang, 2009 #19693; Wang, 2012 #20133; Butovsky, 2014 #22570}. In brief, cells were incubated with primary antibodies or direct conjugated antibodies in FACS buffer (PBS with 2% FBS) for 30-60 min on ice. After washing, cells were incubated with secondary antibodies for 30 min on ice and wash twice with FACS buffer and analyzed by FACScanto (BD Biosciences). FACS data was analyzed by Flowjo software.

Immunofluorescence Staining

Brains were harvested from mice after transcardial perfusion with 4% paraformaldehyde (PFA). Sagittal sections of the brain (8 μm) were treated with permeabilization and blocking solution containing 5% BSA, 2% bovine serum and 0.05% Triton X-100 (Sigma-Aldrich). Primary and secondary antibodies were diluted in PBS containing 5% BSA and 0.05% Triton X-100. Sections were incubated with the primary antibody overnight at 4° C., washed with PBS, and incubated with the secondary Alexa-conjugated antibodies for 1 h at room temperature (20-22° C.) while protected from light. Sections were then washed with PBS and coverslipped in ProLong Gold antifade reagent with DAPI (Invitrogen) and imaged using Olympus Fluoview FV1000 confocal laser scanning microscope.

Antibodies

The following antibodies were used in the present study: anti-FLAG antibody (Sigma-Aldrich), mouse anti-LAP1 antibody (37232; R&D Systems), mouse anti-pro-TGF-β1 antibody (TW4-2F8; Biolegend), biotinylated goat anti-LAP1 antibody (BAF246; R&D Systems), MYC antibody (clone 9E10, from BWH core), Penta-His HRP Conjugate (QIAGEN), APC or Alexa 546-labeled goat anti mouse immunoglobulin G (Invitrogen), APC-anti-FLAG (Biolegend), mouse anti-CD68 antibody (clone FA-11, Abcam) and horseradish peroxidase (HRP)-conjugated sheep antimouse IgG and streptavidin-HRP (GE Healthcare). Mouse anti-Iba1 antibody (Wako), mouse anti-OSP antibody (Abcam), mouse anti-NF-H antibody (Biolegend), mouse anti-NeuN antibody (clone EPR12763, Abcam).

Microarray Analysis

Microarray processing was performed by the Molecular Biology Core Facilities at the Dana-Farber Cancer Institute. Briefly, total RNA was isolated from 3-week old mice brain for FACS-sorted microglia (CD45low CD11b+ CD39+ Ter119− PI−) using Trizol (Invitrogen) according to the manufacturer's protocol. RNA quality and integrity were verified using a Bioanalyzer 2100 (Agilent Technologies), and then hybridized with Affymetrix Mouse Exon 1.0 ST arrays. Arrays were processed using the oligo BioConductor package {Carvalho, 2010 #24670} and normalized using RMA {Irizarry, 2003 #24671} to provide expression summaries at the exon level, and quality assessment was performed with the arrayQualityMetrics Bioconductor package. Affymetrix annotation files were used to collapse probesets to the 'core' set of annotations and summarize the expression data at the gene level, which was used as input for differential expression analysis and significant genes were identified using limma {Smyth, 2005 #24672}. Gene Set Enrichment Analysis (GSEA) {Subramanian, 2005 #24494} was carried out on the full expression data matrix and the 'hallmark (H)' gene sets database was selected for enrichment analysis, which represents 50 specific well-defined biological states or processes.

Statistical Analysis

GraphPad Prism 6 software (La Jolla, Calif.) was used for all statistical tests in this paper. Analyses used include unpaired Student's t-test and log-rank (MantelCox) test (as mentioned in figure legends) and data are presented as mean±SEM. No statistical methods were used to pre-determine sample sizes. However, sample sizes are similar to those studies in previous publication {Bialas, 2013 #22826, Zhang, 2014 #24481}. Data collection and analysis were performed blind to the conditions of all experiments. Data for each experiment was processed randomly and mice were assigned to different experimental groups randomly as well. All p and n values and statistical tests are indicated in figure legends; a p-value of less than 0.05 was considered as significant.

Example 2

LRRC33 associates with proTGF-β1 on cell surface.

Figure 1B:
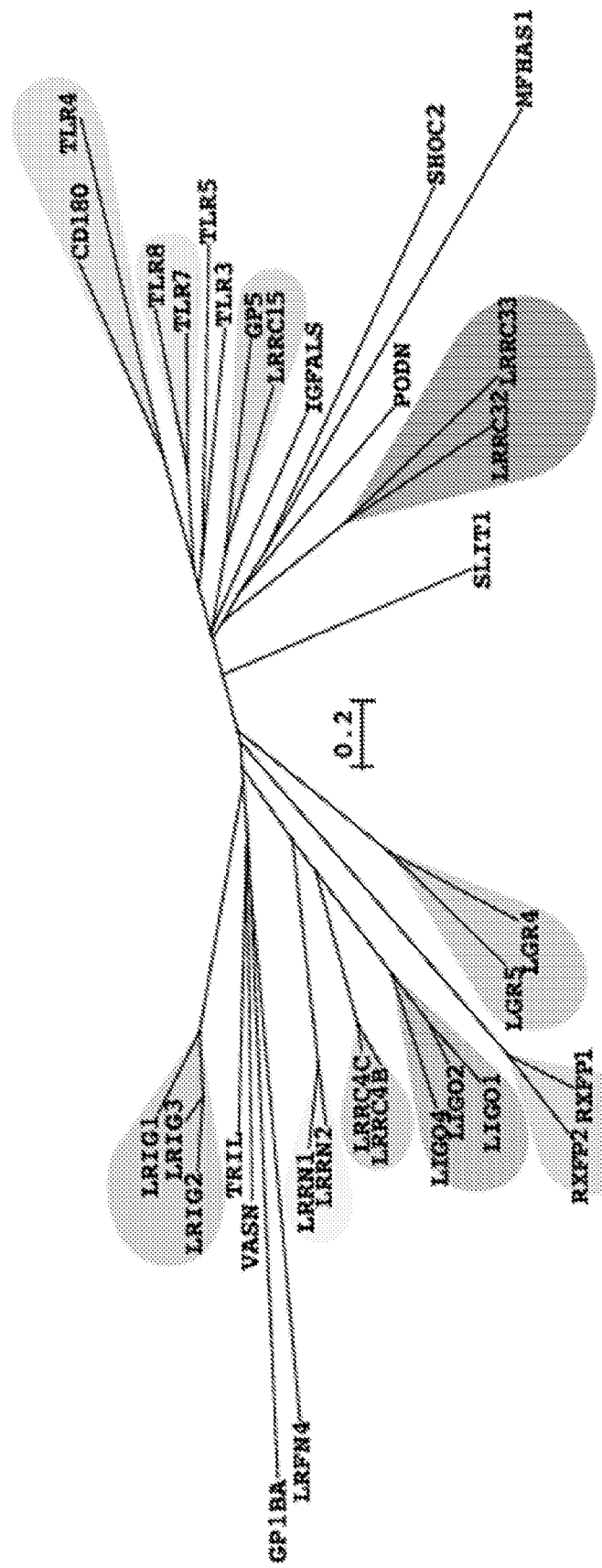

LRRC33 became of interest because BLAST searches revealed close homology to GARP (LRRC32) and GARP associates with latent TGF-β and displays it on cell surfaces for activation {Stockis, 2009 #19432; Tran, 2009 #19465; Wang, 2012 #20133}. The ectodomains of LRRC33 and GARP are more highly related to one another (35% amino acid sequence identity, >99% clustering in bootstrap calculations) than to any other leucine-rich repeat (LLR) family proteins (FIGS. 1A and 1B). The phylogram in FIG. 1B shows closely related LRR proteins with branch lengths scaled to sequence difference and significant subfamilies (>95% by bootstrap calculations) in colored teardrops. The identity between LRRC33 and GARP is comparable to that between TLR4 and CD180, between TLR7 and TLR8, greater than that among TLRs 3, 5, 7, 8 and CD180, and comparable to that among extracellular protein families that associate with related ligands.

Figure 1C:
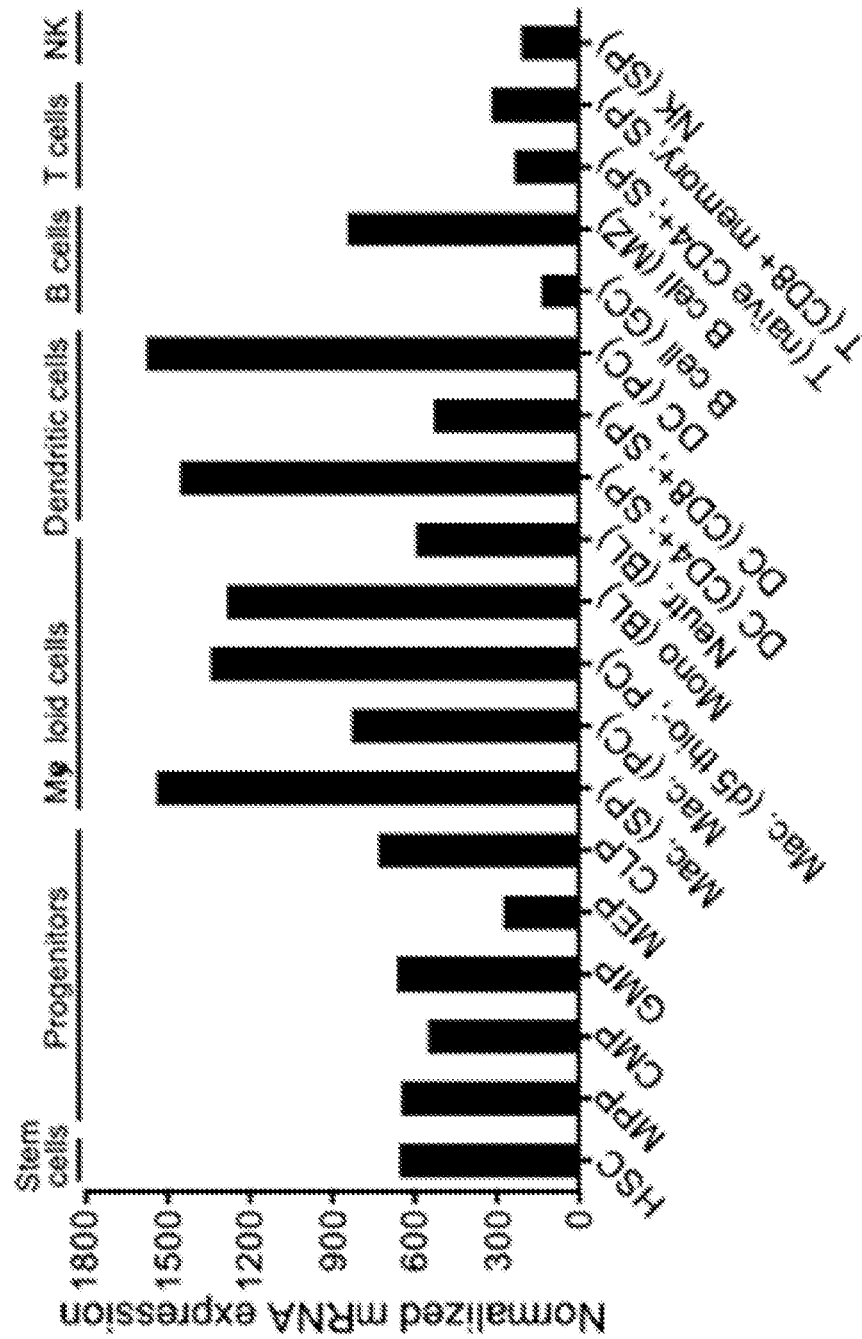
Figures 1D, 1E:
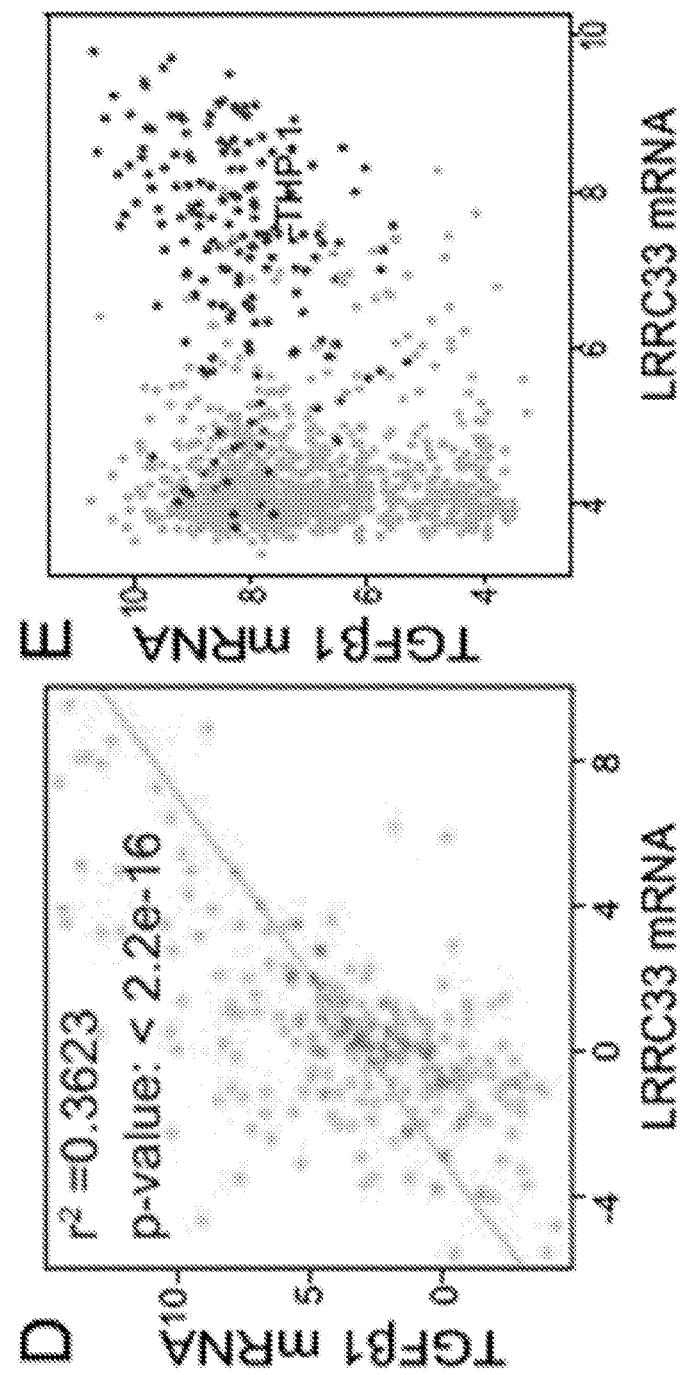

LRRC33 and GARP each contain a signal sequence, an ectodomain containing 23 LRRs, a transmembrane domain, and an 11 residue cytoplasmic domain (FIG. 1A). Cysteine residues 192 and 331 in GARP disulfide link to a Cys in each pro-TGF-β monomer to form a 1:2 complex {Wang, 2012 #20133}. The conservation of these Cys residues in LRRC33 (FIG. 1A, asterisks), and in none of the other aligned LRR family proteins (not shown), strongly indicated that LRRC33 would also associate with and disulfide link to pro-TGF-β. LRRC33 is expressed on myeloid cells (FIG. 1C), and among normal human tissues, mRNA expression of LRRC33 and TGF-β1 correlate (FIG. 1D)

Figures 2A, 2B:
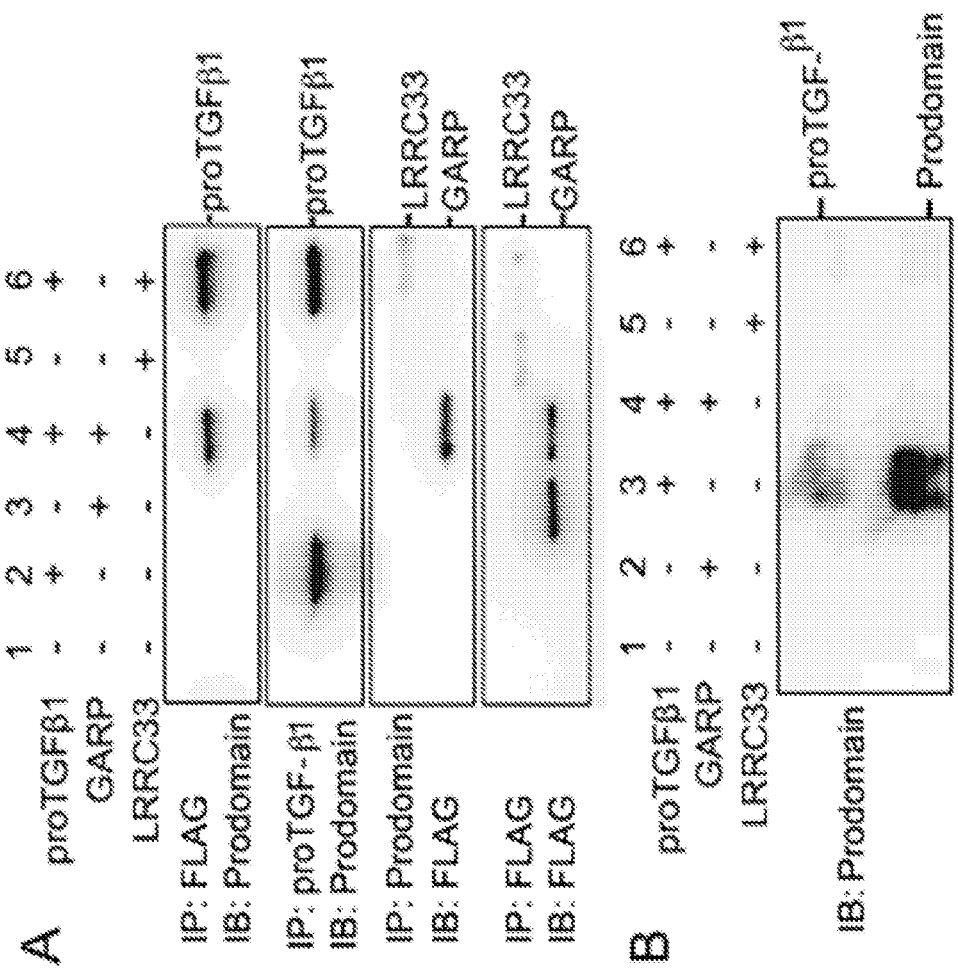
FIGS. 2A-2G shows that LRRC33 is expressed on THP-1 cell surface and 293T transfection experiments with immunoprecipitation and immunoblotting that show that LRRC33 associates with pro-TGF-β1 through a disulfide bond. (A) LRRC33 is associated with proTGF-β1 in the cell lysate and (B) regulates the secretion of proTGF-β1. 293T transfectant lysates (A) or supernatants (B) were immunoprecipitated (IP), subjected to 10% reducing SDS-PAGE and blotted (IB) as indicated. (C) Cys-200 and Cys-344 of LRRC33 disulfide link to proTGF-β1. The cell lysates were immunoprecipitated with anti-LRRC33 antibody, subjected to 7.5% non-reducing and 10% reducing SDS-PAGE, and blotted with the indicated antibodies. (D) LRRC33 outcompetes LTBP for proTGF-β1. 293T cells were transfected with the indicated cDNA expression vectors. Lysates were immunoprecipitated (IP), subjected to 7.5% non-reducing SDS-PAGE, and blotted (IB) as indicated. (E) LRRC33-proTGF-β1 complex is detected in THP-1 cells. THP-1 cells were stimulated by PMA (80 nM) and cell lysates were immunoprecipitated (IP), subjected to 7.5% reducing and non-reducing SDS-PAGE and blotted (IB) as indicated. (F) LRRC33, proTGF-β1 and integrin αVβ6 on cell surface of THP-1 cells are detected by using anti-LRRC33, anti-LAP, anti-proTGF-β1 and anti-integrin αVβ6 antibodies with or without 24 hours PMA stimulation (80 nM). (G) TGF-β1 can be activated from LRRC33-proTGF-β1 complex on THP-1 cells. DMSO or PMA (80 nM) stimulated THP-1 cells (cell number as indicated) co-cultured with TMLC to measure active TGF-β production. Data represent mean+ SEM of quadruplicate samples.

Using immunoprecipitation and Western blotting, the prediction that LRRC33 associates with pro-TGF-β1 was confirmed. 293T cells were transfected with N-terminally FLAG-tagged GARP or LRRC33 in presence or absence of pro-TGF-β1 as indicated (FIGS. 2A and 2B). IP of cell lysates with FLAG antibody followed by blotting with antibody to the TGF-β1 prodomain, or IP with the prodomain followed by blotting with the FLAG antibody, showed association of both GARP and LRRC33 with pro-TGF-β1 (FIG. 2A; lanes 4 and 6). Cells transfected with pro-TGF-β1 alone secrete it into the supernatant {Wang, 2012 #20133} (FIG. 2B, lane 3) and such secretion is prevented by co-expression with GARP (FIG. 2B, lane 4). Similarly, co-expression with LRRC33 completely prevented pro-TGF-β1 secretion (FIG. 2B, lane 6), providing further evidence for LRRC33 association with pro-TGF-β1.

Figure 2C:
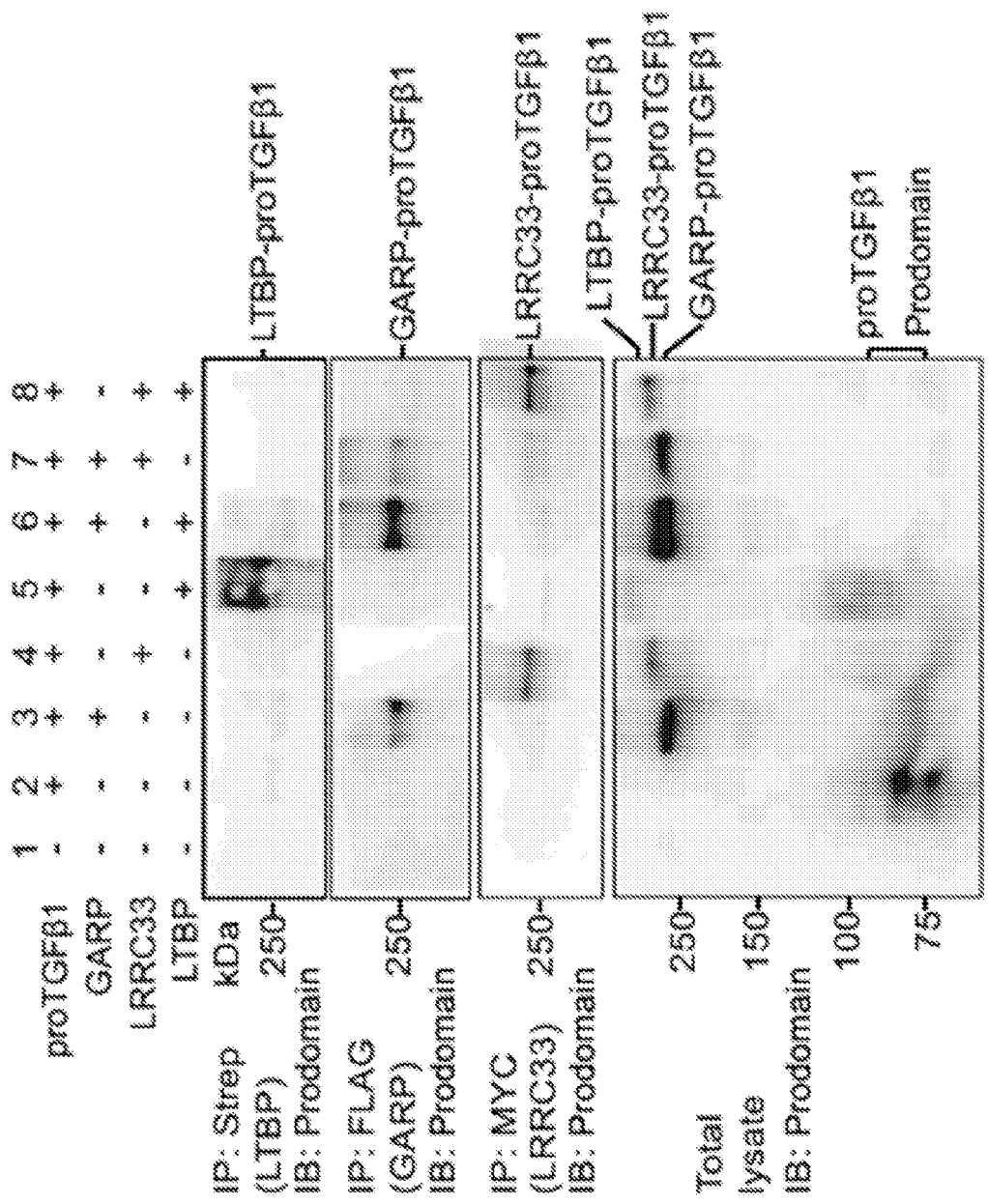

Not only did LRRC33 co-associate with pro-TGF-β1, it also disulfide linked to it as shown in non-reducing SDS-PAGE (FIG. 2C). Whereas pro-TGF-β1 migrated at 75 to 100 kDa in non-reducing SDS-PAGE, LRRC33 co-expression shifted the Mr of proTGF-β1 immunoreactive material to >250 kDa (FIG. 2C, lower panel); IP of Myc tagged LRRC33 showed that LRRC33 co-migrated at the same high Mr in non-reducing SDS-PAGE (FIG. 2C, upper panel). The previous finding that when GARP, LTBP, and pro-TGF-β1 are co-expressed, GARP outcompetes LTBP and binds all the pro-TGF-131 {Wang, 2012 #20133} was confirmed herein (FIG. 2C, upper two panels, lanes 5 and 6). Unexpectedly, LRRC33 also outcompetes LTBP for pro-TGF-β1 (FIG. 2C, panels 1 and 3, lanes 6 and 8). Moreover, GARP and LRRC33 compete equally with one another for pro-TGF-β1 (FIG. 2C, panels 2 and 3, lanes 3, 4, and 7).

Figure 2D:
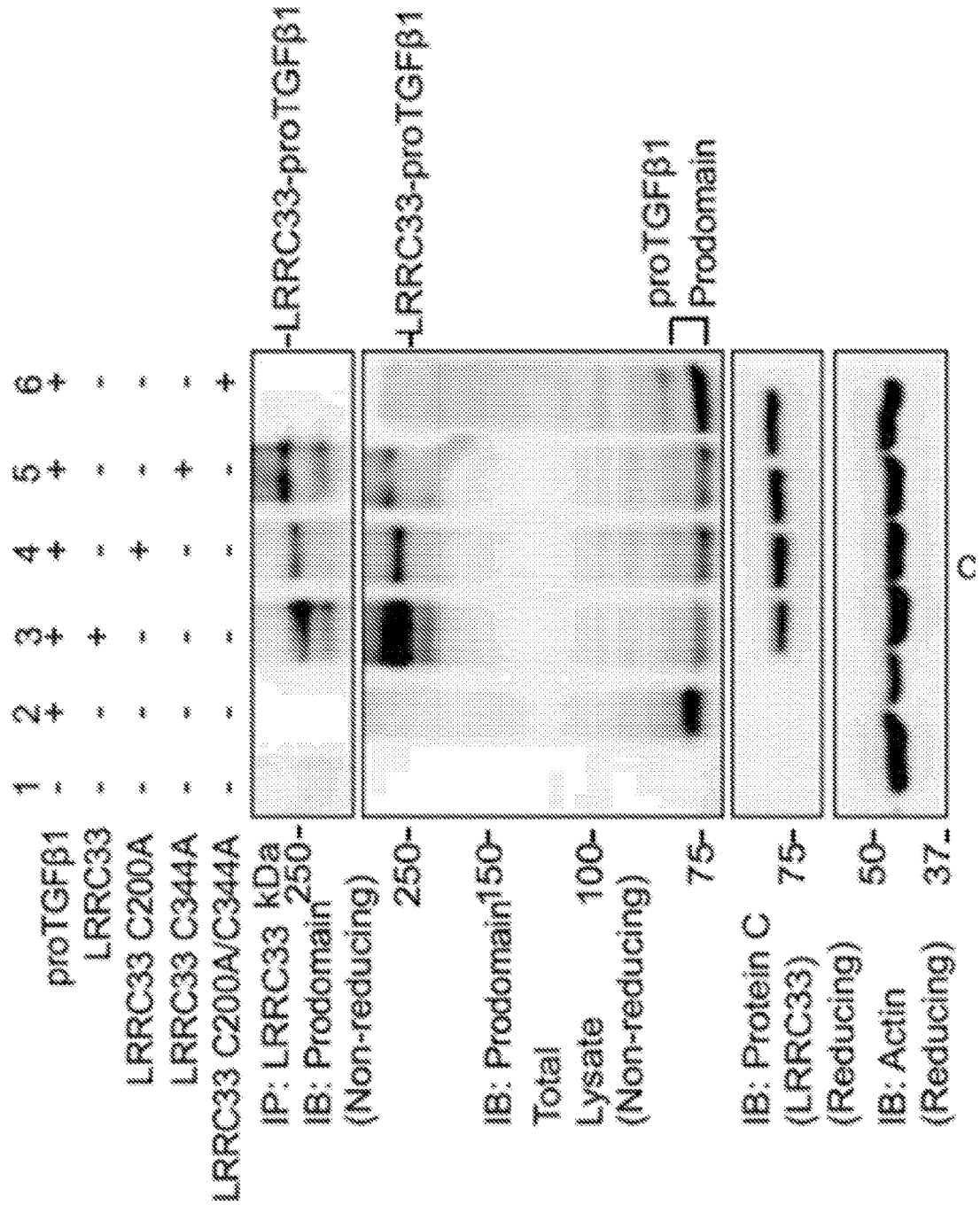

These results demonstrate that LRCC33 is functionally homologous to GARP in its ability to bind and disulfide link to pro-TGF-β1 and prevent secretion of pro-TGF-β1 from cells. Structural and functional homology was further tested by mutation of Cys residues 200 and 344 in LRRC33 (asterisked in FIG. 1A). Double, but not single, mutation of homologous Cys residues 192 and 331 in GARP abrogates disulfide linkage to pro-TGF-β1, showing that they disulfide link to Cys-4 in the prodomain monomers of latent pro-TGF-β1 complex {Wang, 2012 #20133}. The LRRC33 C200A and C344A single mutants and C200A/C344A double mutant were expressed at similar levels as WT LRRC33 in 293T cells (FIG. 2D, third panel). Single cysteine mutations did not abolish disulfide formation, but slowed migration in SDS-PAGE (FIG. 2D, upper two panes, lanes 4 and 5 compared to 3), as expected from greater elongation in SDS of the LRRC33-pro-TGF-β1 complex after removal of one disulfide cross-link, as also observed with GARP {Wang, 2012, #20133}. In contrast, the C200A/C344A double mutant failed to disulfide crosslink to pro-TGF-β (FIG. 2D, panels 1 and 2, lane 6). Thus, LRRC33 not only resembles GARP in covalently associating with pro-TGF-β1, but uses homologous cysteines to do so.

Figure 2E:
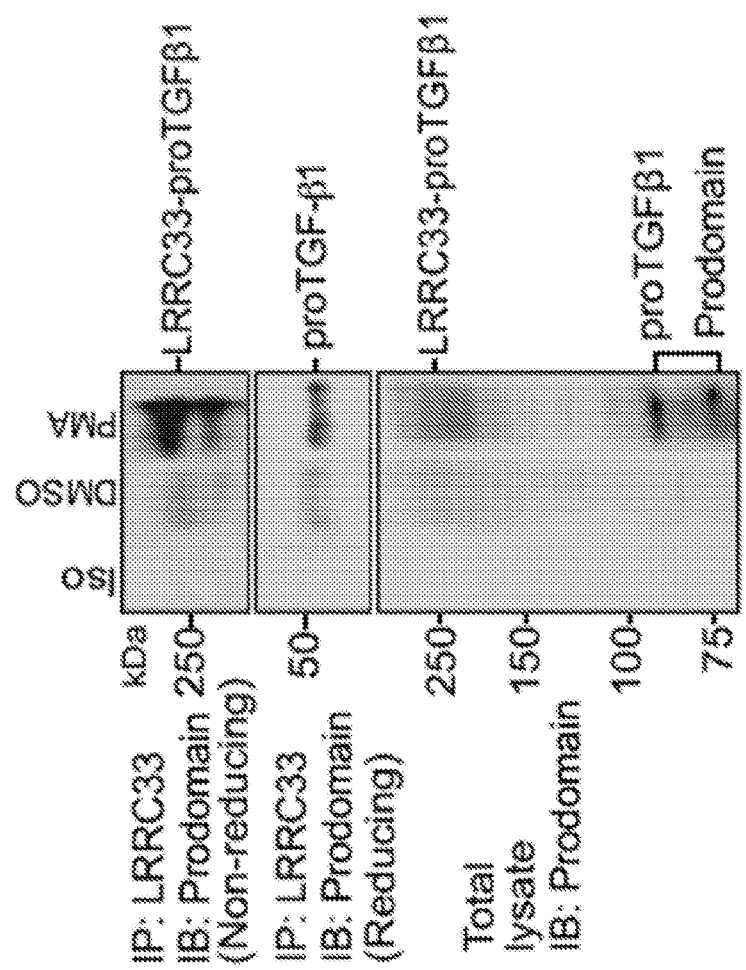
Figures 2F, 2G:
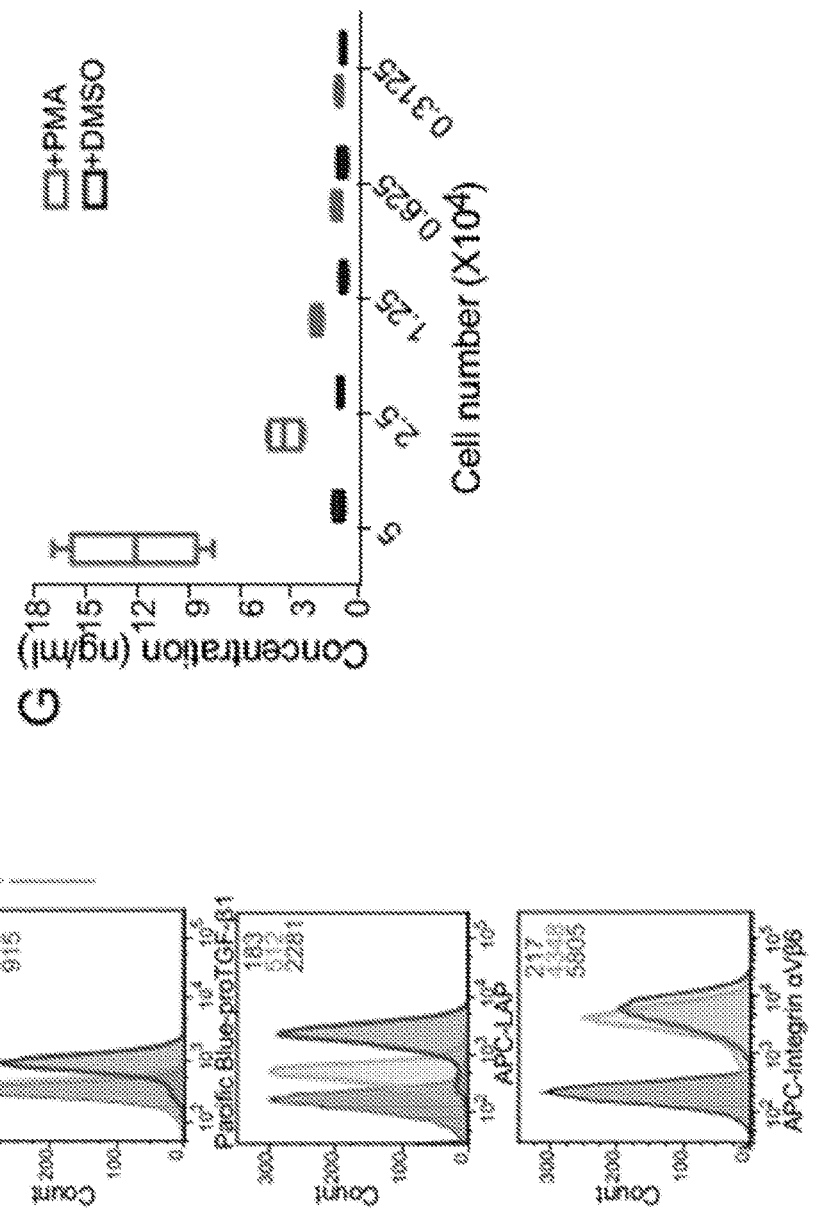

To characterize native LRRC33, a mouse antibody that reacts with human but not mouse LRRC33 was prepared. This antibody recognized both LRRC33 and the LRRC33-pro-TGF-β1 complex (FIG. 8A). LRRC33 was characterized on the myelomonocytic cell line THP-1, which, like other myeloid tumor lines, shows high LRRC33 mRNA expression (FIG. 1E), and when terminally differentiated with phorbol myristyl acetate (PMA), increases pro-TGF-β1 expression {Taipale, 1994 #24496}. Native LRRC33-pro-TGF-β1 disulfide-linked complexes were present in THP1 cells, and were increased in amount after differentiation for 1 day in PMA (FIG. 2E). Furthermore, LRRC33 and pro-TGF-β1 were present on the surface of THP1 cells as shown by immunofluorescent flow cytometry, and expression was increased by PMA (FIG. 2F).

Because THP-1 has endogenous expression of LRRC33-pro-TGF-β1 complex, the localization of LRRC33 was investigated. FACS results using anti-LRRC33 mAb indicate that LRRC33 is expressed on THP-1 cell surface, and the expression is significantly increased after PMA stimulation (FIG. 2F, upper panel). LRRC33 can bring large amount of proTGF-β1 to cell surface after PMA stimulation, as shown with antibody to the proTGF-β1 (TW4-2F8). AML193 and MV4-11 also shown consistent results (data not shown), which confirmed that, like GARP, LRRC33 can also anchoring proTGF-β1 on cell surface for activation. However GARP is only present TGF-β1 on platelets and activated Treg cells {Tran, 2009 #19465}. LRRC33 anchors TGF-β1 on myeloid cells such as macrophages and microglia (FIG. 4B), which has been known as major source of TGF-β1 production in CNS {Lehrmann, 1998 #22606}.

Several αV integrins were shown to activate TGF-β in different context {Munger, 1999 #14536; Ludbrook, 2003 #16510; Wipff, 2007 #18474}, and previous studies indicate that αl/36 and Vβ8 integrins can be activated TGF-β from GARP-proTGF-β1 complex {Wang, 2012 #20133}. Thus, whether the LRRC33-proTGF-β complex on THP-1 cell surface could serve as a source of activated TGF-β was determined. αVβ6 integrin was found to have very high expression on THP-1 cell surface by FACS (FIG. 2F DMSO or PMA stimulated THP-1 cells cocultured with transformed mink lung TGF-β-reporter cell line (TMLC) {Abe, 1994 #19452} and results indicated that there are large amount of activated TGF-β released from PMA stimulated THP-1 cells.

Unlike GARP, LRRC33 by itself barely expressed on cell surface of 293T transfectant, but co-express with proTGF-β1 can bring both LRRC33 and proTGF-β1 to cell surface (FIG. 8A), indicating that unlike GARP, LRRC33 need to form a complex with proTGF-β1 to express on the cell surface. Moreover, a "hybrid LRR" strategy {Jin, 2008 #22724} was used to make chimeras between LRRC33 and GARP at positions shown in FIG. 1A: X1 and X5. In the absence of co-expression with proTGF-β1, the chimera with surface expression comparable to GARP was 33-32-X1 (FIG. 8A), which contains the N-terminal 188 amino acids of LRRC33. 33-32-X5, which contains the EC domain of LRRC33 and TM-IC domain of GARP, can also express on cell surface but the expression level of 33-G-X5 is significantly enhanced when co-express with pro-TGF-β1 (FIG. 8A). Together, these results conclude that 1) that pro-TGF-β1 and LRRC33 require are co-dependent for surface expression, and 2) that GARP differs from LRRC33; surface expression of GARP is not dependent on pro-TGF-β1.

Disruption of Lrrc33 results in ascending paraparesis in Lrrc33$^{-/-}$ mice.

To test in vivo function, Lrrc33 was knocked out by capturing its expression with LacZ and terminating its transcription prior to exon 4, which encodes >90% of the protein (FIG. 9A). Heterozygous mice were fertile and healthy (FIGS. 3A-3E). Homozygous Lrrc33$^{-/-}$ mice were sometimes runted (FIG. 3A) with a yield at weaning of 10% compared to the Mendelian expectation of 25%. They developed normally for the first 2 months with no unusual features detected in tissue sections of major organs from euthanized mice except for a higher incidence of pneumonia, otitis media, and rhinitis than littermates.

Figures 3A, 3B, 3C, 3D:
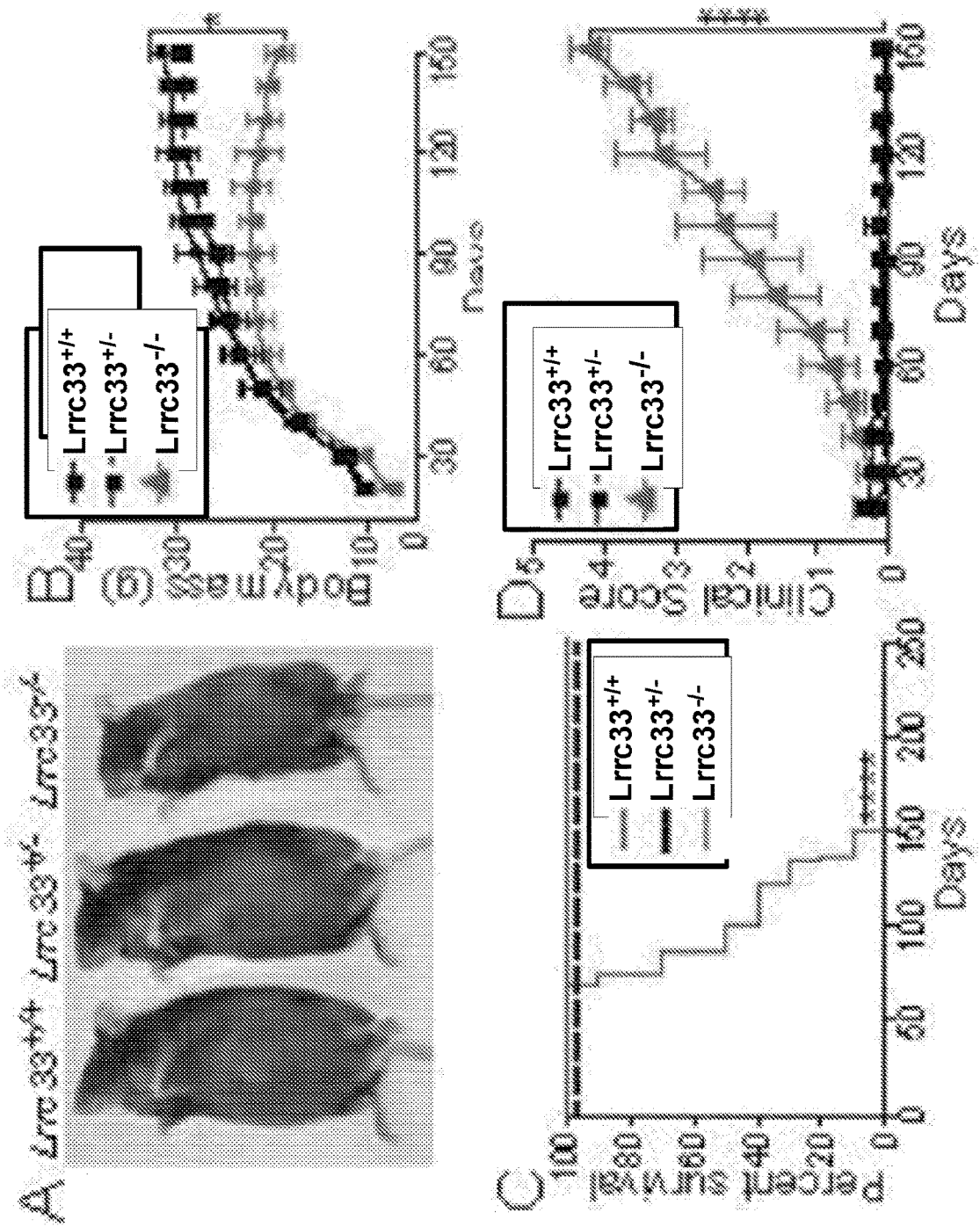
FIGS. 3A-3F show Lrrc33−/− mice have shortened life span and progressive spastic paraparesis. (A) Lac33+/+, Lrrc33+/− and Lrrc33−/−. (B) Body mass and (C) Kaplan-Meier survival curve of Lrrc33+/+, Lrrc33+/− and Lrrc33−/− mice. Data are mean±SEM. *P<0.05, **P<0.0001. Unpaired Student's t-test (B) and log-rank (MantelCox) test (C). (D) Clinical scores and (E) Rotarod test. Data are mean±SEM, **P<0.0001 (unpaired Student's t-test). (F) Quantification of NeuN+ cells. Data represent mean±SEM. (4-month, n=3).
Figures 3E, 3F:
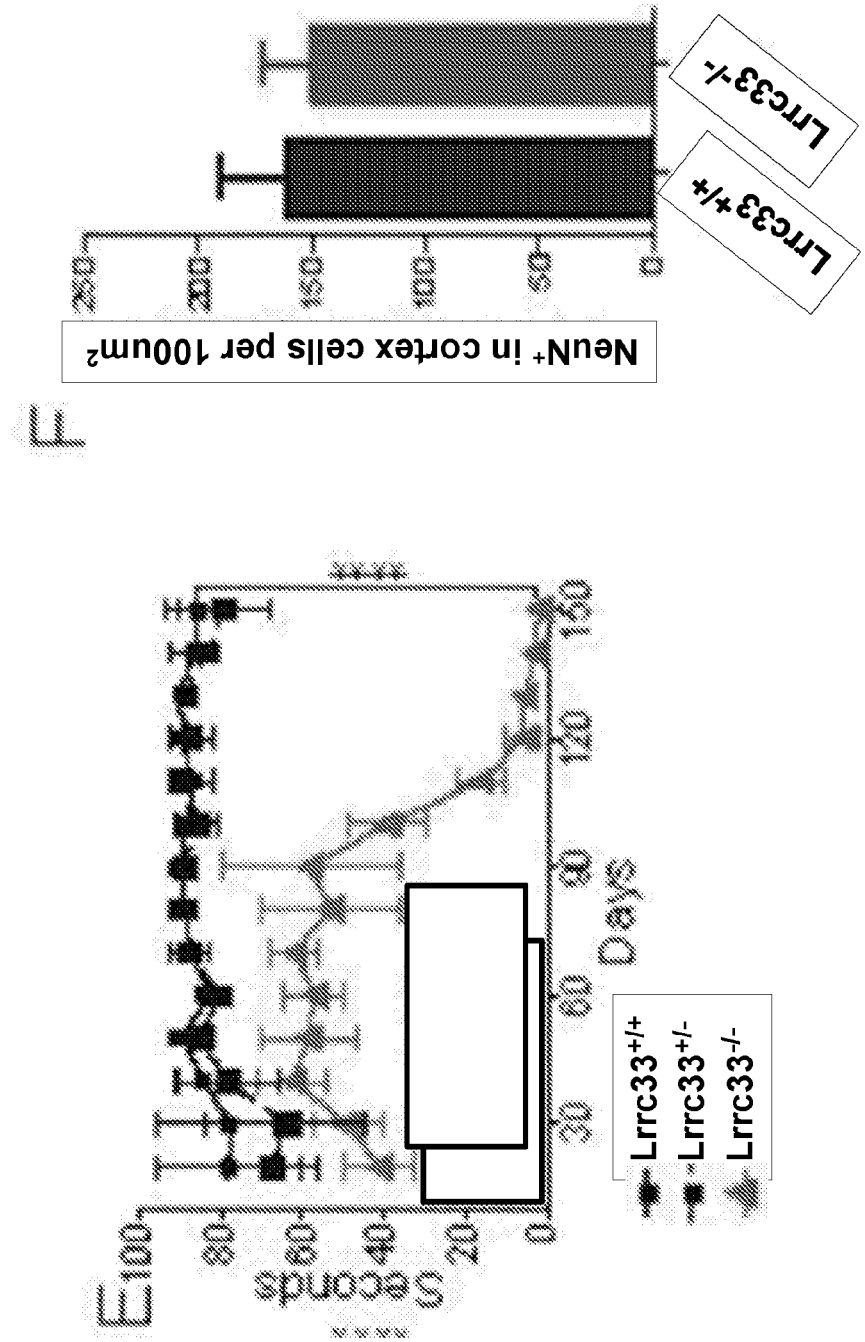

However, by 60 days, growth slowed in Lrrc33$^{-/-}$ mice and they developed ascending paraparesis with progressive loss of hind limb grasp, hind limb coordination, and bladder control, an inability to right themselves, and quadriplegia requiring euthanasia. These five symptoms were aggregated into a 5-point clinical scale, which rose steadily after 60 days (FIG. 3D). Lack of bladder control assessed by fur wetness correlated with a failure of reflex urination: euthanized Lrrc33$^{-/-}$ mice had highly distended bladders. Diuresis was not present as shown by normal water consumption. All Lrrc33$^{-/-}$ mice had died by 150 days (FIG. 3C). A rotarod test to monitor coordination showed that Lrrc33$^{-/-}$ mice were unable to maintain themselves on a rotating cylinder as long as their littermates, and performance greatly decreased after 90 days (FIG. 3E). Hematoxylin-eosin stained brain and spinal cord sections of 4-5 month-old Lrrc33$^{-/-}$ mice showed signs of myelin loss with accumulation of lipid-laden (foamy) macrophages (data not shown). Immunohistochemistry demonstrated a lack of infiltrating B or T lymphocytes and thus ruled out an autoimmune etiology (data not shown).

Further histochemistry and immunohistochemistry showed that progressive paraparesis was associated with loss of myelin and axonal degeneration. In contrast to well organized linear myelin tracts in Lac33$^{+/+}$ mice, myelin staining with luxol fast blue and anti-oligodendrocyte specific protein (OSP) revealed disorganized or deficient myelin, respectively, in Lac33$^{-/-}$ cerebral cortex and spinal cord (data not shown). Myelin was disorganized in the spinal cords of Lac33$^{-/-}$ mice, with depletion of Luxol fast blue-staining material in the outer white matter and unusual staining in the grey matter (data not shown). Axons were examined because their loss is often associated with demyelination. Bielschowsky silver stain and anti-neurofilament-heavy (NF-H) to visualize axons revealed substantial loss of axons in Lrrc33-/- cerebral cortex (data not shown). Silver stain showed loss of axons in spinal cord white matter and NF-H staining similarly showed loss of axons in Lac33$^{-/-}$ mice compared to WT mice (data not shown). In contrast to loss of axons in cerebral cortex, there was little effect on the overall number of neurons, as shown by quantification of NeuN+ cells (FIG. 3F). Loss of myelin and axons in Lrrc33$^{-/-}$ mice correlates with and provides a cellular mechanistic basis for the observed neurological phenotypes. Loss of axons in humans as well as mice is associated with ascending paraparesis, because longer axons such as those that innervate the hind limbs and bladder are generally more susceptible and are lost prior to shorter axons such as those that innervate the forelimbs.

Expression LRRC33 and Association of its Loss with Microglia Abnormalities and Activation.

Figures 1F, 1G:
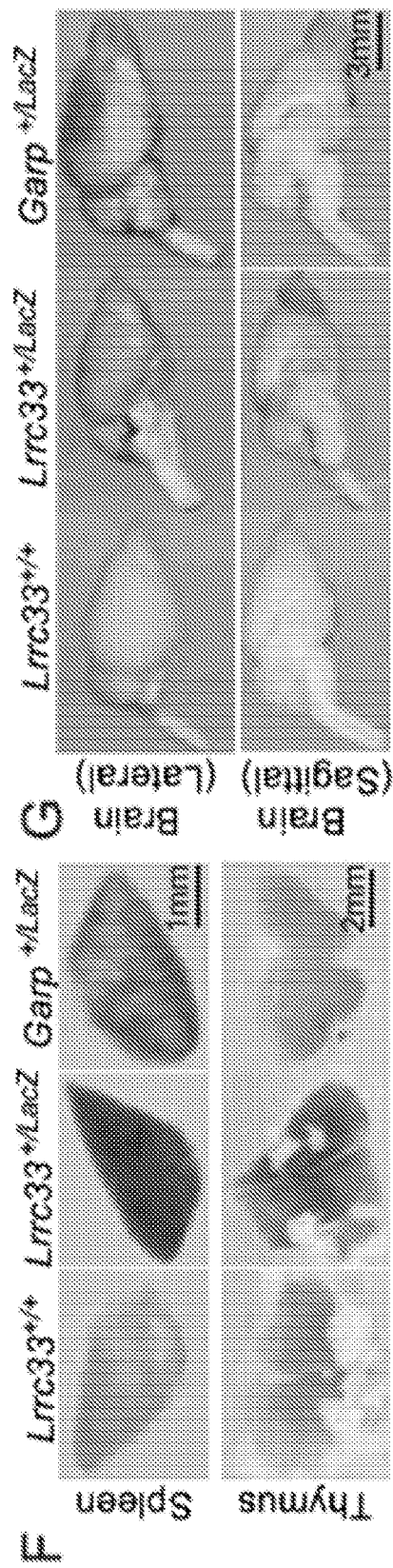
Figure 1H:
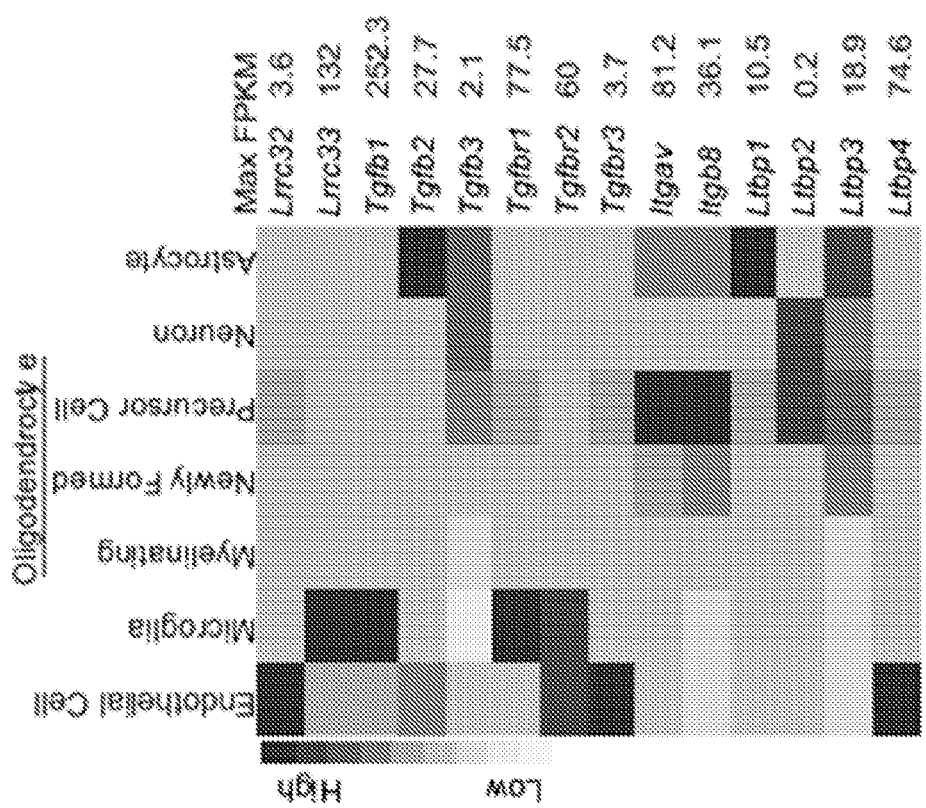
Figures 4A, 4B, 4C, 4D:
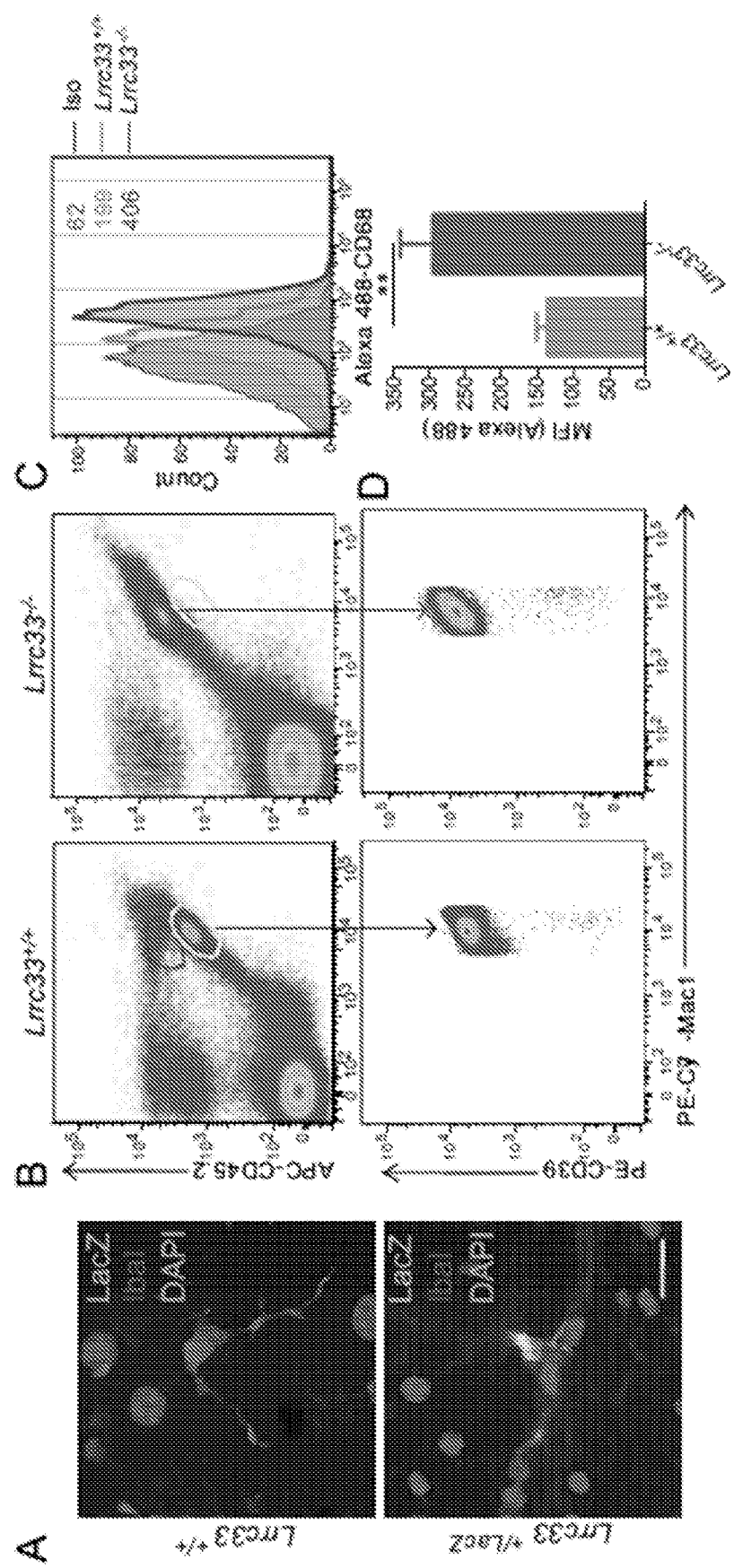
FIGS. 4A-4G show microglia alterations and activation in Lrrc33−/− mice. (A) Immunostaining of brain sections using anti-beta gal and anti-Iba1. Scale bar=10 um. (B-D) Lrrc33−/− mice possess altered microglia and express more CD68. Representative FACS analysis (B) of microglia cells stained for Mac1 and CD39 among CD45+ cells at day 21 (n=3); Representative FACS analysis (C) and MFI (D) of microglia cells stained for CD68 cells at day 21 (n=3), data are presented as mean±SEM; (F) Immunostaining of brain sections using anti-Iba1 and anti-CD68. Scale bar=50 um. (F) Less pro-TGF-β production in microglia and peritoneal macrophage of Lrrc33−/− mice. Freshly isolated microglia (day 21) and peritoneal macrophages co-cultured with TMLC cells and luciferase activities were detected after 24 hours culture. Data are presented as mean±SEM; P<0.01, **P<0.0001 (unpaired Student's t-test). (G) WT donor derived microglia in Lrrc33−/− recipients. Immunostaining of brain sections using anti-Iba1 and anti-CD45.2. Scale bar=10 um.

Human and mouse microarray and RNAseq datasets showed that Lrrc33 expression is largely if not completely limited to cells of hematopoietic origin. Among these cells, Lrrc33 expression is highest on myeloid lineage cells including macrophages and dendritic cells, is also high on B cells, and is generally low on T cells and NK cells (FIGS. 1C-1E). Heterozygous mice carrying one allele in which expression of the Lrrc33 or Garp genes was captured with a LacZ reporter used to compare expression. The lacZ substrate X-gal generates an insoluble blue product that maps gene expression in tissues. Lrrc33 was strongly expressed in spleen, and at lower levels in thymus where its expression was greater than seen with endogenous b-galactosidase in WT (FIG. 1F). In contrast, Garp was not detectable over background in either organ. Little Lrrc33 was expressed in liver, kidney, heart, lung, and skin, confirming expression limited to hematopoietic cells. In the brain, Lrrc33 was widely and diffusely expressed (FIG. 1G). In contrast, Garp was localized diffusely within the frontal cerebral cortex, and strongly expressed in blood vessels (FIG. 1G). Expression of Lrrc33, Garp and other TGF-β context and signaling molecules were examined by cell populations isolated from murine brain using a high quality RNA-Seq database {Zhang, 2014 #24481} (FIG. 1H). Lrrc33 is highly expressed on microglia, in agreement with its diffuse distribution in the brain by LacZ staining, and shows little expression on endothelial cells, pericytes, neurons, astrocytes, or newly formed, myelinating, or precursor oligodendrocytes. TGF-β1 is also more highly expressed in microglia than other cell types in the brain. In contrast, Garp is highest on pericytes and endothelial cells, in agreement with its presence in blood vessels in the brain by LacZ staining. To localize Lrrc33 expression in cerebral cortex, immunofluorescence microscopy was used. Antibody to Iba1, a marker for microglia {Butovsky, 2014 #22570}, identified these cells with their characteristic highly ramified, long processes. Antibody to lacZ was selective for LacZ, as shown by staining of sections from Lrrc33$^{+/LacZ}$ and not WT mice, and co-localized with Iba1 to highly ramified microglial cells (FIG. 4C). Thus, by RNA-Seq, as well as fluorescent microscopic localization of Lrrc33 expression in brain sections, LRRC33 is specifically expressed in microglial cells within the brain.

The finding that Lac33$^{-/-}$ is selectively expressed in microglia in the CNS indicated that microglia is be responsible for the neurological phenotype; furthermore, mice that are genetically deficient in Tgfb1$^{-/-}$, but are protected from autoimmune disease by TGF-β1 expression in T lymphocytes (CNS Tgfb1$^{-/-}$ mice), develop neurological symptoms very similar to those of Lrrc33$^{-/-}$ mice and display perturbation or loss of microglia {Butovsky, 2014 #22570}. Studies on microglia in Lac33$^{+/+}$ mice to Lrrc33$^{-/-}$ microglia were performed to investigate how loss of Lrrc33 affects microglia immunophenotype and morphology. Microglia immunophenotype was examined in brain cells isolated from 3 week old Lrrc33-/- mice using flow cytometry. Microglia were identified as CD45$^{low}$ and Mac1$^+$ cells, as well as being identified as CD39$^{high}$ cells in flow cytometry to exclude CD39$^{neg/low}$ monocytes/macrophages from the microglia gating strategy described herein {Butovsky, 2014 #22570}. Interestingly, CD45$^+$ cells in Lac33$^{-/-}$ brain (mostly leukocytes) express more CD45 than their counterparts in WT brain, as shown by higher expression in both Mac1$^-$ and Mac$^+$ subsets (FIG. 4B upper). However, when CD45 and Mac1 gates were appropriately adjusted (FIG. 4B upper), all gated cells were CD39$^{high}$, confirming their identity as microglia (FIG. 4B, lower). Sorted microglia showed increased expression of the lysosome associated membrane protein CD68 (macrosialin), a marker of microglia activation (FIG. 4C). The increase was statistically significant in microglia sorted from brains of multiple Lac33$^{-/-}$ mice (FIG. 4F).

Figures 4E, 4F, 4G:
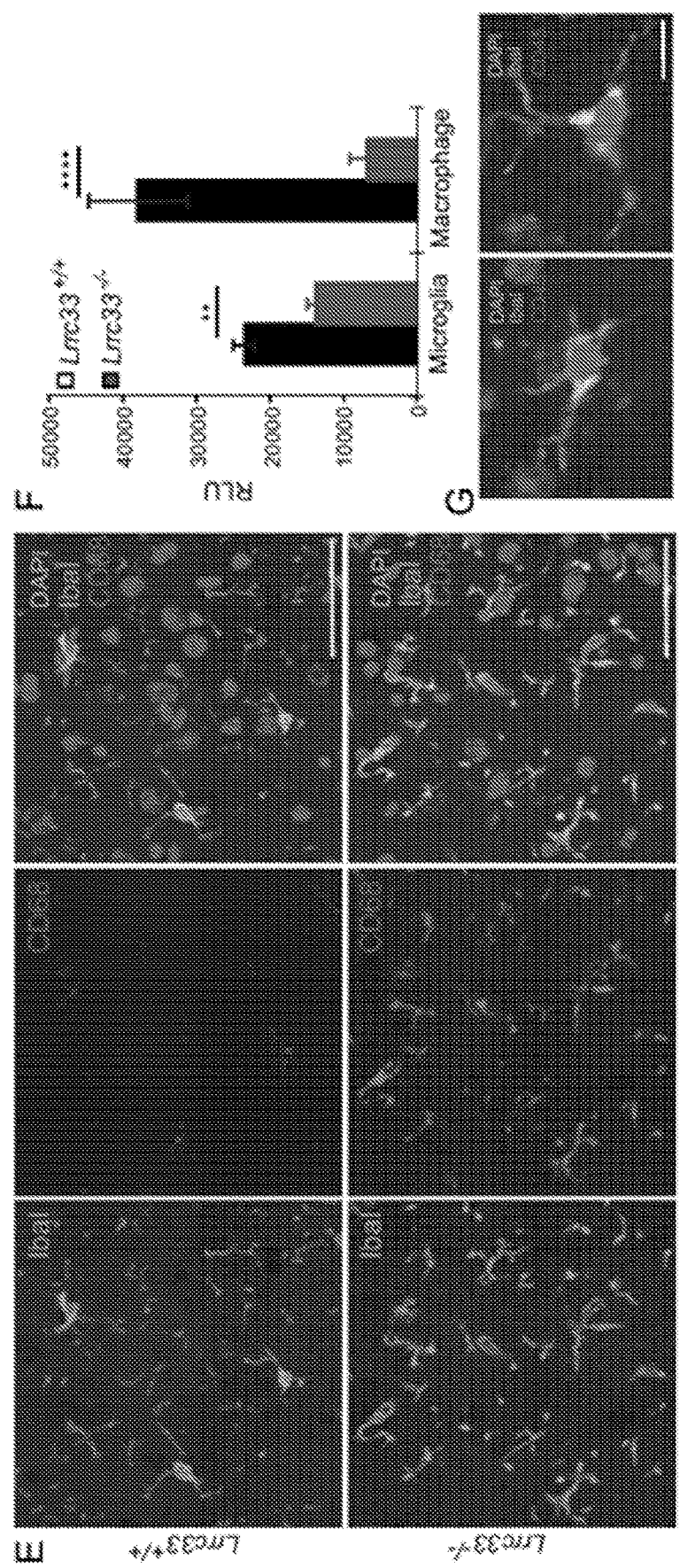

Immunofluorescent microscopy of cerebral cortex sections further demonstrated that CD68 was markedly upregulated on microglia, as confirmed by co-expression with Iba1 (FIG. 4E). Moreover, the morphology of the microglia in Lac33$^{-/-}$ mice defined them as reactive (activated) microglia, because they had fewer cellular processes which were thicker, less ramified, and did not extend as far into their cellular neighborhoods as the WT microglia, which had a typical resting, ramified morphology (FIG. 4E).

Next, the TGF-β reporter cells were utilized to assay how loss of LRRC33 affects active TGF-β production by microglia and peritoneal macrophages (FIG. 4I). Loss of LRRC33 was found to lead to a significant decrease in active TGF-β production by Lac33$^{-/-}$ microglia and macrophages, verifying an important role for LRRC33 in TGF-β biosynthesis or activation.

Disease Progression of Lrrc33$^{-/-}$ Mice is Arrested by Wild Type Whole Bone Marrow Transplantation and Accompanied by Microglia Repopulation.

Without wishing to be bound by a particular theory, it is hypothesized that the neurological defects observed in Lrrc33$^{-/-}$ mice could be reversed by whole bone marrow transplantation (wBMT) for several reasons: 1) there was a lack of evidence for T cell infiltration into the brain or any autoimmune component, 2) LRRC33 expression is limited in the brain to microglia indicating microglia are the primary driver of disease in the Lrrc33-/- mice, and 3) wBMT is effective in rescuing other microglia-related pathologies {Wirenfeldt et al., 2011}. A mouse congenic system was utilized, in which donor and recipient blood-derived cells can be differentiated through their surface expression of the CD45.1 or CD45.2 alleles of the pan-hematopoietic cell marker CD45, to intravenously transplant 8 million freshly harvested whole BM cells into lethally irradiated mouse recipients. Four possible transplantation combinations utilizing Lac33$^{+/+}$ and Lac33$^{-/-}$ mice, including Lac33$^{+/+}$ wBM into irradiated Lrrc33$^{+/+}$ and Lac33$^{-/-}$ recipients, and Lrrc33$^{-/-}$ wBM into irradiated Lac33$^{+/+}$ and Lrrc33$^{-/-}$ recipients were performed. Utilizing the same neurological scoring as FIG. 3D, transplanted mice were screened for neurological defects and ultimately sacrificed at 5 month post wBM transplantation to determine by flow cytometry and immunohistochemistry donor cell contribution to the host CNS. Two independent transplantation experiments gave similar results (FIGS. 5 and 8A).

Following the transplants, Lac33$^{-/-}$ mice were 0-5 weeks old, and already showed clinical symptoms; nonetheless, transplantation with WT wBM rescued 60% of Lac33$^{-/-}$ mice from disease progression and death, whereas transplantation with Lrrc33$^{-/-}$ wBM did not (FIG. 5A). Notably, Lac33$^{-/-}$ recipients of Lrrc33$^{+/+}$ wBM showed significantly decreased progression of neurological symptoms (FIG. 5B), while Lac33$^{-/-}$ recipients of Lrrc33$^{-/-}$ BM showed neurological disease progression similar as observed in naive Lac33$^{-/-}$ mice (FIG. 5C), demonstrating that not only does transplantation of wild type wBM arrest Lrrc33$^{-/-}$ neurodegeneration, but also this arrest is not due simply to the irradiation. WT mice transplanted with WT or Lac33$^{-/-}$ wBM showed no deaths or neurological signs (FIG. 5A; data not shown).

Figures 5E, 5F:
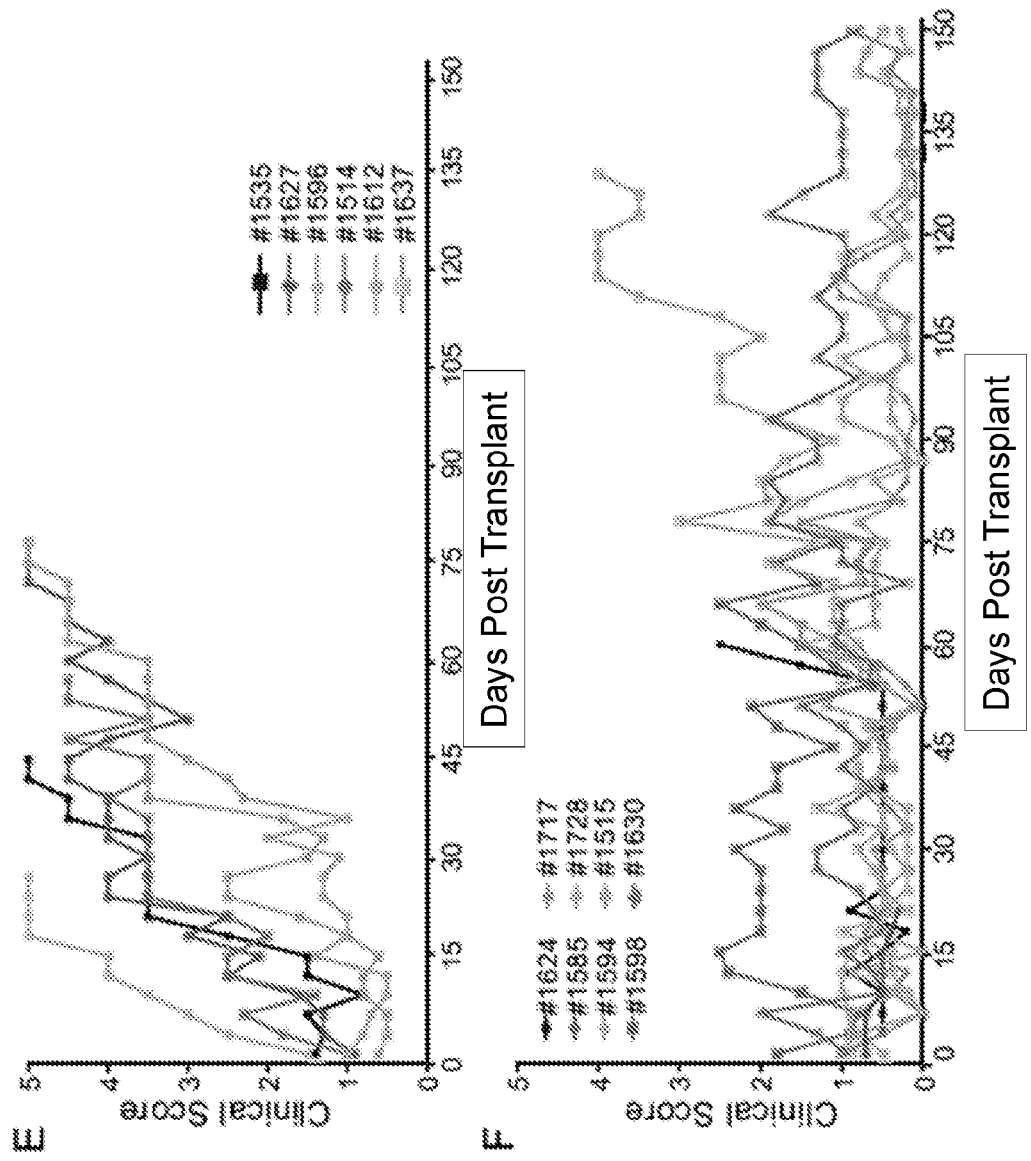
Figures 5G, 5H:
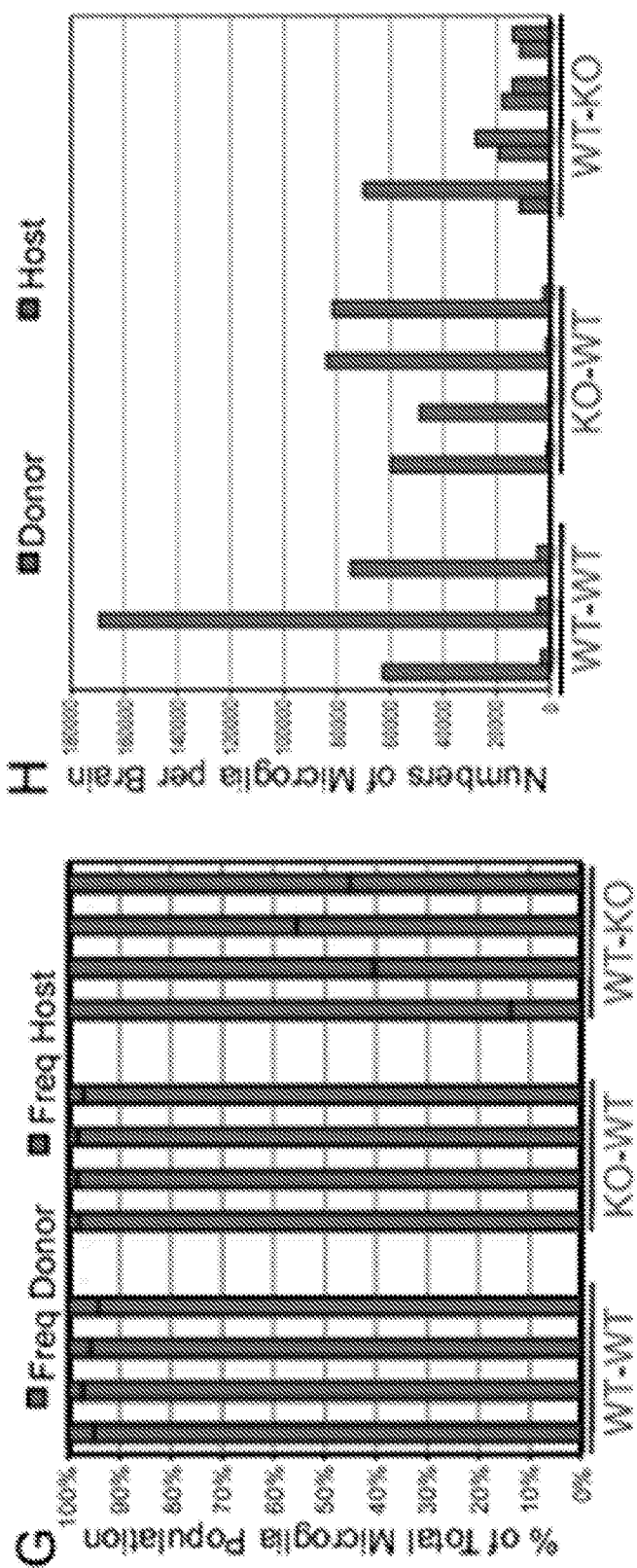

Transplanted mice were sacrificed to assess whether their microglia were of donor or host origin using the CD45.1 and CD45.2 alleles. Microglia were assessed by flow cytometry as CD45.1$^{low}$ or CD45.2$^{low}$, Mac1$^+$, and CD39$^{high}$ (FIGS. 5B-5D, left). Including CD39$^{high}$ as a microglia marker within the microglia flow cytometry analysis described herein excludes possible donor-derived CD39$^{neg/low}$ monocytes/macrophages that could also have engrafted into recipient mouse brains. Donor and recipient microglia were then quantitated using CD45.1 and CD45.2 (FIGS. 5D-5F, right). Microglia chimerism was measured in 4 mice each for three transplant groups, and expressed as % of total microglia (FIG. 5G) or as number of microglia recovered per brain (FIG. 5H). There was little chimerism in wild type mice receiving wild type wBM (4.1±1.4%) or in wild type mice receiving Lrrc33$^{-/-}$ wBM (2.4±0.65%). In marked contrast, Lrrc33$^{-/-}$ transplant recipients receiving wild type wBM showed significantly higher levels of donor-derived wild type microglia within their brains (68±16% of total microglia) (FIG. 5G). Moreover, the total number of microglia per Lrrc33$^{-/-}$ brain was increased by WT donor microglia and in one animal approached levels found in WT recipients (FIG. 5H). Thus, the high level of donor-derived wild type microglia in Lrrc33$^{-/-}$ recipient mice correlated with their extended lifespan and decreased neurological scores and likely contributed to their improved health.

Brain sections from Lrrc33-/- recipients of wild type wBM were additionally examined. Donor BM-derived microglia cells were present as shown by their staining with antibodies to both CD45.1 and IbaI (FIG. 4J). Moreover, donor cells showed normal microglia morphology with well ramified cellular processes. Unlike untreated Lrrc33$^{-/-}$ mice that show signs of demyelination and loss of axons at 4 to 5-months old (data not shown), most Lac33$^{-/-}$ transplant recipients of wild type wBM exhibited relatively normal myelination and axon morphology (data not shown) at 8 months of age, 5-months post-BMT.

Molecular signature of Lrrc33$^{-/-}$ microglia.

Figures 6A, 6B:
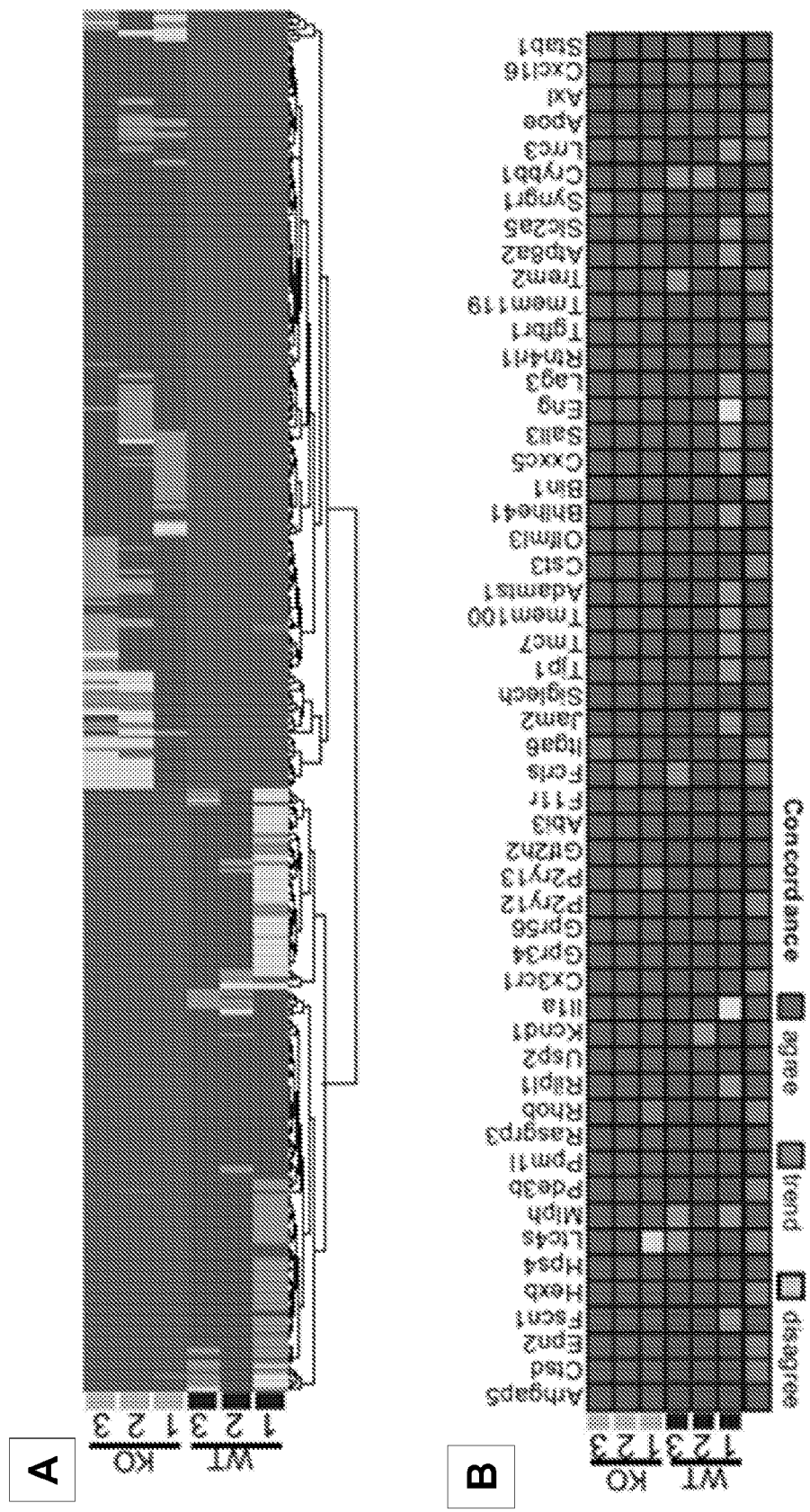
FIGS. 6A-6D show effect of Lrrc33 deficiency on transcriptional phenotype of microglia. (A) Replication of Lrrc33−/− microglia signature in 3 WT and 3 KO animals. Dark red and blue correspond to genes with Log FC>1.5; adjusted p value<0.05. (B) Lrrc33−/− microglia and CNS tgfb1−/− microglia have very similar signatures (see key). Agree means change in both datasets with Log FC>1.5; p-value<0.05; trend means same direction of change in two datasets but Log FC<1.5 or p-value<0.05; disagree means opposite direction of change in two datasets. (C) GSEA showing significantly enrichment TGF-β signaling in WT microglia. (D) GSEA results showing all Hallmarks with false discovery rate (FDR)<0.2 and family wise-error rate (FWER)<0.66. ES, enrichment scores.
Figures 10A, 10B:
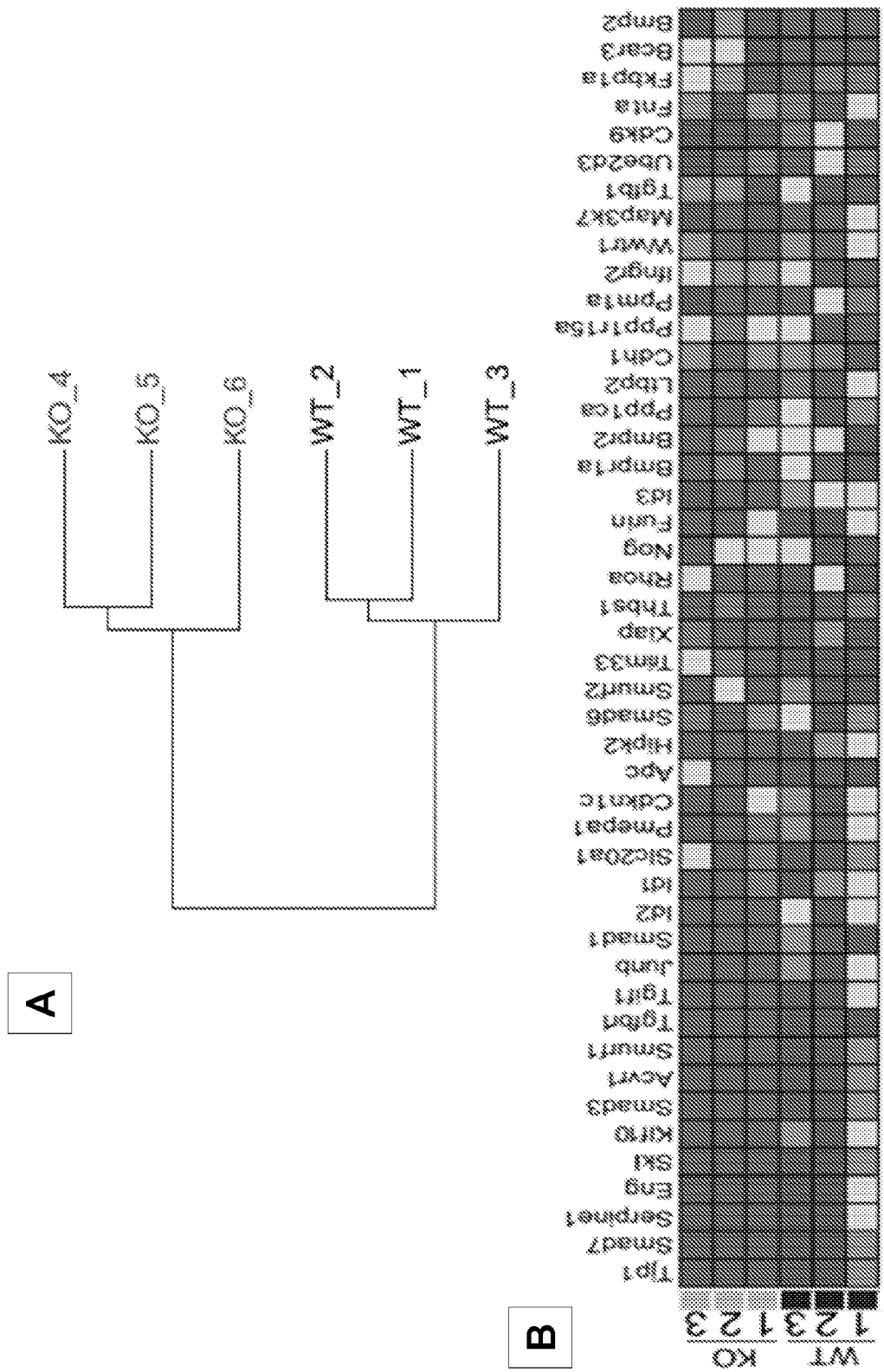
FIGS. 10A-10C show gene expression comparison for WT and knockout (KO) samples. (A) Unsupervised Global Hierarchical Clustering shows the WT and KO samples fall into 2 separate groups. (B) GSEA showing significantly down-regulated TGF-β target gene in knockout microglia. (C) GSEA showing five significantly enrichment signaling in knockout microglia, including E2F targets, G2M checkpoint, mitotic spindle, IFN-α and IFN-γ response.

Having identified microglia as a key player in Lrrc33-/- neuropathology, how loss of LRRC33 affects microglia function was next assessed by performing a transcriptional comparative analysis between wild type and Lrrc33−/− microglia. Sacrificed mice were perfused to minimize possible contamination of microglia with monocytes, macrophages, and other blood cells. Utilizing the immunophenotype $CD45^{low}$, $Mac1^+$, $CD39^{high}$ $Ter119^-$, microglia were sorted from 3 wild type and 3 $Lac33^{-/-}$ 3-week old mice and their transcriptional profiles were analyzed using the Affymetrix Murine Exon 1.0 ST platform. The six transcriptome datasets clearly clustered in an unsupervised hierarchical manner into two distinct wild type and $Lrrc33^{-/-}$ groups (FIG. 10A) with $Lrrc33^{-/-}$ microglia possessing 180 down-regulated and 232 up-regulated genes (FIG. 6A). Both wild type and $Lrrc33^{-/-}$ cell populations expressed unique, previously identified microglia-specific markers, e.g. CD39 and Fcrls {Butovsky, 2014 #22570}, ensuring their microglia origin and excluding monocyte/macrophage contamination. Previously, 354 genes were found to be selectively expressed in microglia compared to macrophages, and 62 of these were found to differ in expression more than 5-fold between WT and CNS Tgfb1−/− microglia {Butovsky, 2014 #22570}. Differential expression of these 62 genes was completely concordant between CNS Tgfb1−/− microglia and Lrrc33−/− microglia (FIG. 6B; all-green concordance bar). This concordance strongly indicates that Lrrc33 is required for Tgfβ1 signaling in microglia, is consistent with the biochemical evidence that LRRC33 TGF-β1 noncovalently and covalently associate, and further indicates that LRRC33 is the only context molecule required for TGF-β1 function in microglia.

Gene Set Enrichment Analysis.

Figures 6C, 6D:
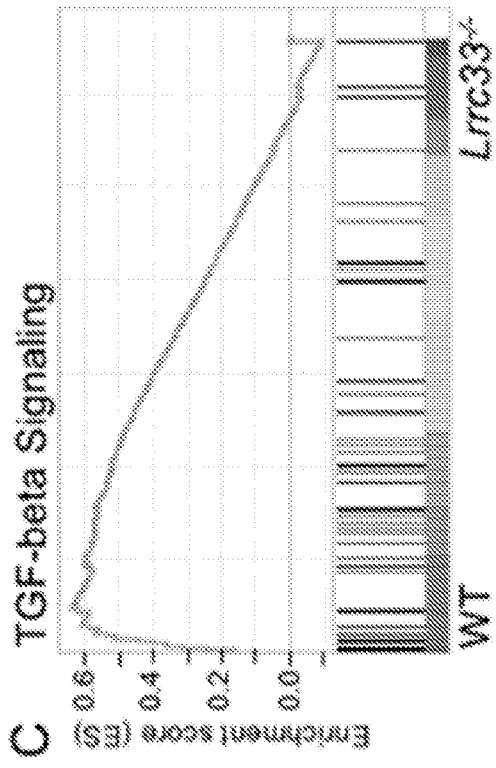
Figure 10C:
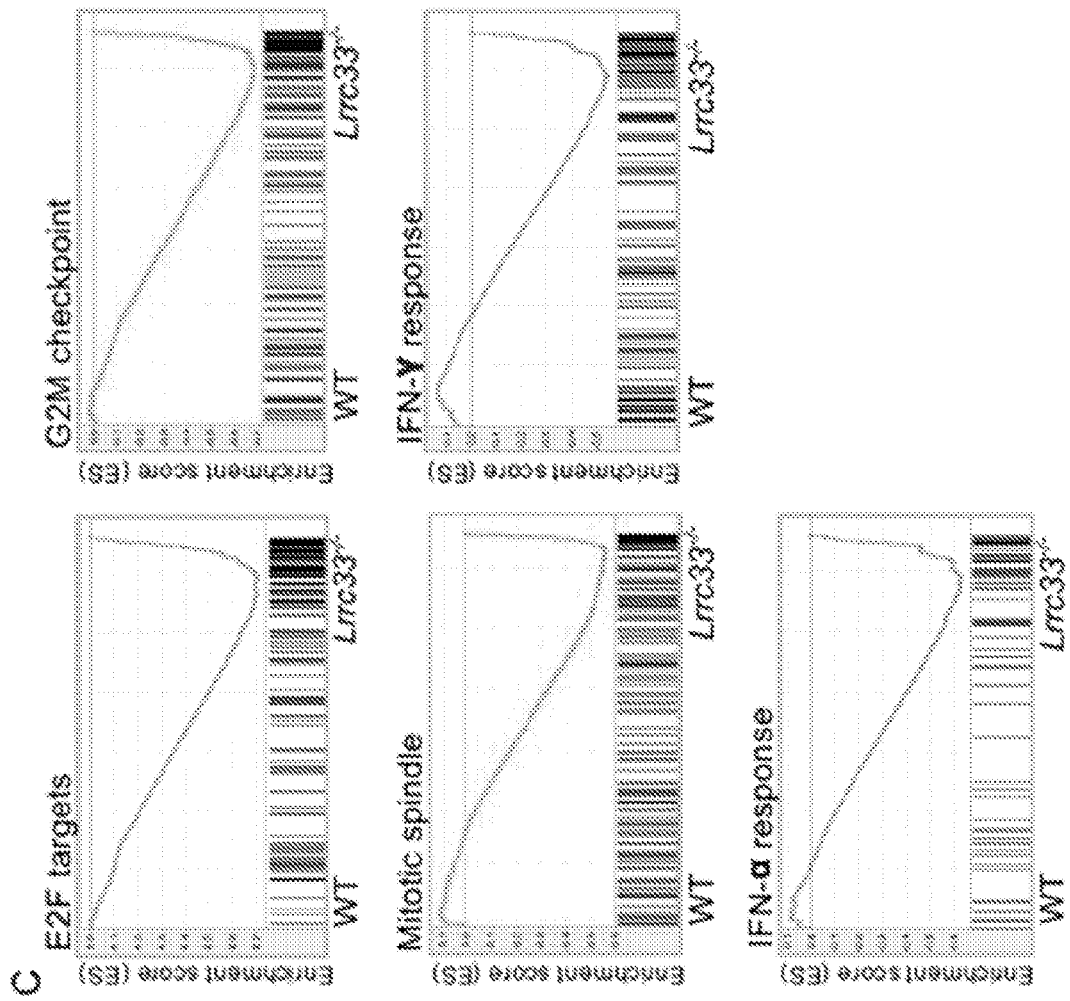

(GSEA) examines sets of genes that function together in key biological functions including signaling, metabolism, cell division, and biosynthesis and show coordinate differential expression {Subramanian, 2005 #24494}. "Hallmark" gene sets characteristic of 50 different signaling pathways have been curated that enable an unbiased, inductive approach to identifying signaling pathways that are affected in disease, cellular treatments, or genetic deficiency. In this method, differentially expressed genes are ranked, and enrichment scores (ES) are calculated based on the frequency of occurrence of hallmark genes near the top (positive ES) or bottom (negative ES) of these rankings (FIGS. 6C and 6D). Quite strikingly, among 50 biological pathways, "TGF-β signaling" was the most statistically enriched pathway in wild type microglia compared to Lrrc33−/− microglia (FIGS. 6C 6D, and FIG. 10B), providing independent support for the model that LRRC33 is required for TGF-β signaling in microglia. GSEA further revealed significant negative ES scores (enrichment in Lrrc33−/− relative to wild type microglia) for "Interferon-α response" and "Interferon-γ response" pathways (FIG. 6D and FIG. 10C). Enrichment of these pathways indicate activation of $Lac33^{-/-}$ microglia. $Lac33^{-/-}$ microglia were also significantly enriched for "E2F targets" "G2M checkpoint," and "Mitotic spindle" (FIG. 6D and FIG. 10C). These pathways are all associated with cell cycling. However, there was also a trend for enrichment of the "Apoptosis" gene set in $Lac33^{-/-}$ microglia, although it did not reach significance (FIG. 10C).

Discussion

The level of sequence identity between LRRC33 and GARP (also known as LRRC32) of 35% is much higher than that needed to show proteins are in the same family (20%) and comparable to that between proteins often found to have similar functions. Multiple, independent lines of evidence show herein the Examples that LRRC33 complexes with TGF-β1, and provides a milieu that is distinct biochemically and in cellular localization for display and activation of TGF-β1. It is thus remarkable that previous publications on LRRC33 have proposed two distinct associations. LRRC33 has been proposed to be a TLR homologue and to associate with and negatively regulate TLRs (Liu et al., 2013). However, a previous paper cited by this group on sequence homology among the LRR superfamily found that GARP and LRRC33 form a branch of the LRR superfamily distinct from TLRs, that this subfamily contains LRRC33 and GARP as its only two members, and note that the alternative gene name for LRRC33 is Garp1 (GARP-like 1) (Dolan et al., 2007). These results are consistent with findings described herein (FIG. 1B). Yet another paper proposed LRRC33 as a negative regulator of reactive oxygen species that when associated with the NAPDH oxidase 2 in the ER results in its degradation (Noubade et al., 2014). Although the co-association studies based on IP-Western blotting from these two groups and findings described herein appear incompatible with one another, IP-Westerns have the inherent limitation that they may be done under conditions in which a large number of proteins co-immunoprecipitate, while only the single protein recognized by the antibody used in Western blotting is detected. Work described herein uniquely extended beyond the typical non-covalent association demonstrated in IP-Western blotting to demonstrate highly specific association between LRRC33 and TGF-β1 by four independent means. 1) Co-transfection with LRRC33 prevented secretion of overexpressed TGF-β1 into culture medium. 2) LRRC33 and TGF-β1 formed a covalent, disulfide-linked complex both in transfectants and a myeloid cell line. 3) Mutation of two cysteines in LRRC33 predicted to associate with TGF-β1 abolished covalent association. 4) LRRC33 completely competed away LTBP association with TGF-β1, and partially competed away GARP association. These multiple lines of evidence definitively demonstrate that LRRC33 noncovalently and covalently associates with TGF-β1, and establish LRRC33 as a presenter and anchor for TGF-β1 in myeloid and microglia milieus.

Phenoypes previous described for Lrrc33 knockouts (Noubade et al., 2014; Su et al., 2014) are consistent with by finding that LRRC33 is required for TGF-β1 signaling in a myeloid milieu described herein. The ~2-fold decline in reactive oxygen species production by Lrrc33−/− macrophages (Noubade et al., 2014) is consistent with the long-standing observation that TGF-β potently deactivates macrophages, i.e., inhibits stimulus-specific peroxide secretion (Tsunawaki et al., 1988). GSEA revealed no alteration in "Reactive oxygen species" hallmark genes in Lrrc33−/− microglia. An increase in sensitivity to TLR ligand challenges in $Lrrc33^{-/-}$ mice (Su et al., 2014) is consistent with general attenuation of innate immunity by TGF-β signaling (Flavell et al., 2010) and work described herein the examples demonstrated enhanced IFN-α and IFN-γ signaling in $Lrrc33^{-/-}$ microglia. Consistent with experimental findings presented herein, previous studies have demonstrated that treatment of microglia with TGF-β1 downregulates both secretion of pro-inflammatory cytokines and reactive oxygen species production (Liu et al., 2016; Qian et al., 2008).

Despite no previous overall description of $Lac33^{-/-}$ phenotype in knockout mice, including whether mice were maintained by breeding heterozygotes or homozygotes, curious features indicate possible similarities. The short lifespan of Lrrc33$^{-/-}$ mice and low yield of Lac33$^{-/-}$ mice from heterozygote breeding reported herein is consistent with the paucity of previous experiments on Lrrc33$^{-/-}$ mice. Rather than use such mice, one study instead used WT mice that were transplanted with wBM from Lrrc33$^{-/-}$ mice (Noubade et al., 2014). Experimental findings described herein show that such mice maintain their WT microglia and do not develop neurological disease. Another study reported several in vivo experiments that used WT and heterozygote Lac33$^{+/-}$ mice and omitted homozygote Lac33$^{-/-}$ mice (Su et al., 2014). Furthermore, the latter study reported enlarged bladders in all older Lrrc33$^{-/-}$ mice, consistent with the neurological phenotype described here.

One of the main findings presented herein relates to a previously undescribed milieu molecule that associates with TGF-β, LRRC33, and its importance in the CNS. Macrophages and microglia do not express other proteins known to associate with TGF-β, i.e. GARP or LTBPs 1, 3, and 4. Results showing deficient TGF-β1 signaling in Lrrc33$^{-/-}$ macrophages and microglia in vitro and microglia in vivo are consistent with the requirement for TGF-β for association with a milieu partner molecule for normal biosynthesis in the ER, passage through ER quality control, and subsequent maturation and availability for activation. Such a requirement is common for multi-subunit proteins, including integrins which require both an "a" and a "b" subunit for maturation.

The limitation of Lrrc33 expression in the CNS to microglia together with transplantation experiments described herein provide strong evidence that defects in microglia are responsible for the most obvious phenotype in these mice, ascending paraparesis. In two independent experiments, WT wBM was able to rescue a large portion of transplanted mice from disease progression and otherwise inevitable death. Survival was associated with reconstitution with WT microglia, which displayed a normal ramified morphology. Not all transplanted Lrrc33$^{-/-}$ mice survived, but this may relate to transplantation at an age at which symptoms were already apparent and the time required after transplantation for repopulation of the CNS with microglia. Ascending paraparesis developed in Lrrc33$^{-/-}$ mice between 2 to 5 months, although a rotarod deficit was apparent earlier. As early as 3 weeks, microglia in Lrrc33$^{-/-}$ mice are strongly perturbed as shown by transcriptional profiles, surface marker expression, and morphology in brain sections. However, brain development appeared normal at this age, consistent with results in Tgfb1$^{-/-}$ mice and the stronger expression of TGF-β2 and TGF-β3 than TGF-β1 in early development (Brionne et al., 2003; Butovsky et al., 2014; Kiefer et al., 1995; Krieglstein et al., 1995). Ascending paraparesis was associated with a loss of myelin and axons in the spinal cord. Myelination occurs in mice largely in the first two months after birth. The relatively late appearance of symptoms in Lrrc33$^{-/-}$ mice relates to an important function of microglia in CNS maintenance, including in phagocytosis, synapse pruning, and interactions with neurons and other glial cells including myelin-producing oligodendrocytes {Bilimoria PM and Stevens}{Wirenfeldt, 2011 #24692}. The ramified processes of microglia are highly dynamic, suiting them for surveillance and maintenance functions.

The close similarity in CNS phenotypes and microglia transcriptional profiles in Tgfb1 and Lrrc33 deficient mice strongly indicate that LRRC33 is the only milieu molecule important for TGF-β1 activation in microglia. Microgliosis is evident in Tgfb1$^{-/-}$ mice (Brionne et al., 2003) and Il2-Tgfb1;Tgfb1$^{-/-}$ mice (Butovsky et al., 2014). Similarly, microgliosis in Lrrc33$^{-/-}$ mice is demonstrated by microglia morphology, CD68 expression, and transcriptional profile. Il2-Tgfb1;Tgfb1$^{-/-}$ mice develop motor abnormalities at 3-4 months, show rotarod deficits, and paralysis steadily progresses until death at 6 months (Butovsky et al., 2014). The neurological symptoms, the time of onset, the progression, and the time of death are remarkably similar to those reported herein in Lrrc33$^{-/-}$ mice. Moreover, the TGF-β1-dependent signature reported in microglia from Il2-Tgfb1; Tgfb1$^{-/-}$ mice (Butovsky et al., 2014) and Lrrc33$^{-/-}$ mice are essentially identical. All 58 of 58 upregulated genes and all 4 of 4 downregulated genes in WT compared to Tgfb1$^{-/-}$ microglia were regulated similarly in WT compared to Il2-Tgfb1;Tgfb1$^{-/-}$ microglia. This corresponds to a most unusually high concordance between knockouts of two different genes. These results established that loss of LRRC33 leads to a loss of microglia-derived TGF-β in the CNS that yields a Tgfb1$^{-/-}$-like neurological phenotype.

Extracellular milieus and TGF-β activation, as distinct from intracellular canonical SMAD and noncanonical signaling pathways and distinct cellular transcriptional contexts, are already established to contribute to TGF-β functional diversity. Herein, the term "milieu" specifically is used to distinguish extracellular diversity mechanisms in TGF-β signaling from diversity provided by distinct intracellular "contexts." Milieus can operate on three different levels. They enable TGF-β to be recognized: 1) on the plasma membrane of specific cells (e.g., those expressing LRRC33 or GARP) vs within extracellular matrices (LTBPs), 2) on one cell type (e.g. LRRC33 on microglia and macrophages) vs another (e.g. GARP on endothelium and pericytes), and 3) because milieus differ in expression of many other molecules as well, they will inevitably favor the colocalization of distinctive cells that bear TGF-β activating integrins, e.g. integrin $\alpha_v\beta_6$-bearing epithelial cells, integrin $\alpha_v\beta_8$-bearing glial cells in the CNS and dendritic cells in the immune system, and integrin $\alpha_v\beta_1$-bearing fibroblasts. This makes activation specific for presence of an additional cell type in the milieu, and such cells are also targets for the active TGF-β. Milieus enable cellular selectivity in TGF-β activation, in much the same way that the area code hypothesis for cell localization in tissues or the three-step model for leukocyte emigration from the blood stream enable selectivity. Importantly, milieus enable TGF-β activation to be localized to the interface between an integrin-bearing activating cell and another cell or matrix bearing the proTGF-β-milieu molecule complex. Since active TGF-β is rapidly cleared in vivo, this confines TGF-β activation to highly localized milieus, and distinguishes TGF-β from other members of the family such as bone morphogenetic proteins that diffuse over long distances to establish morphogenetic gradients (Robertson and Rifkin, 2016).

The clear correspondence between the neurological phenotypes of Tgfb1 and Lrrc33 deficiency provides more compelling evidence for the milieu than previous knockouts of milieu molecules (Robertson and Rifkin, 2016). GARP deficient mice are not viable (unpublished data), and their defects have not been characterized. Among the four LTBPs, LTBP1 and LTBP3 associate the best with proTGF-β and show the greatest importance in TGF-β activation. Ltbp1 deficiency results in cardiac and vascular defects and embryonic lethality. Ltbp3 deficiency results in bone defects including osteopetrosis. Tgfb2-deficient mice show defects in multiple organs including heart, lung, craniofacial, limb, spinal cord, eye, inner ear, urogenital system and CNS (Morikawa et al., 2016). Tgfb3-deficient mice defects include pulmonary and palate development (Morikawa et al., 2016). Association of LTBPs and GARP with multiple TGF-β isoforms and some redundancy among milieu molecules may contribute to the difficulty of teasing out the importance of specific milieu molecules for each of the functions of the three TGF-β isoforms. Sorting out milieu molecule functions in white blood cell lineages is easier, because these cells express TGF-β1 and not TGF-βs 2 or 3, and LRRC33 is expressed only in these lineages.

Figure 7:
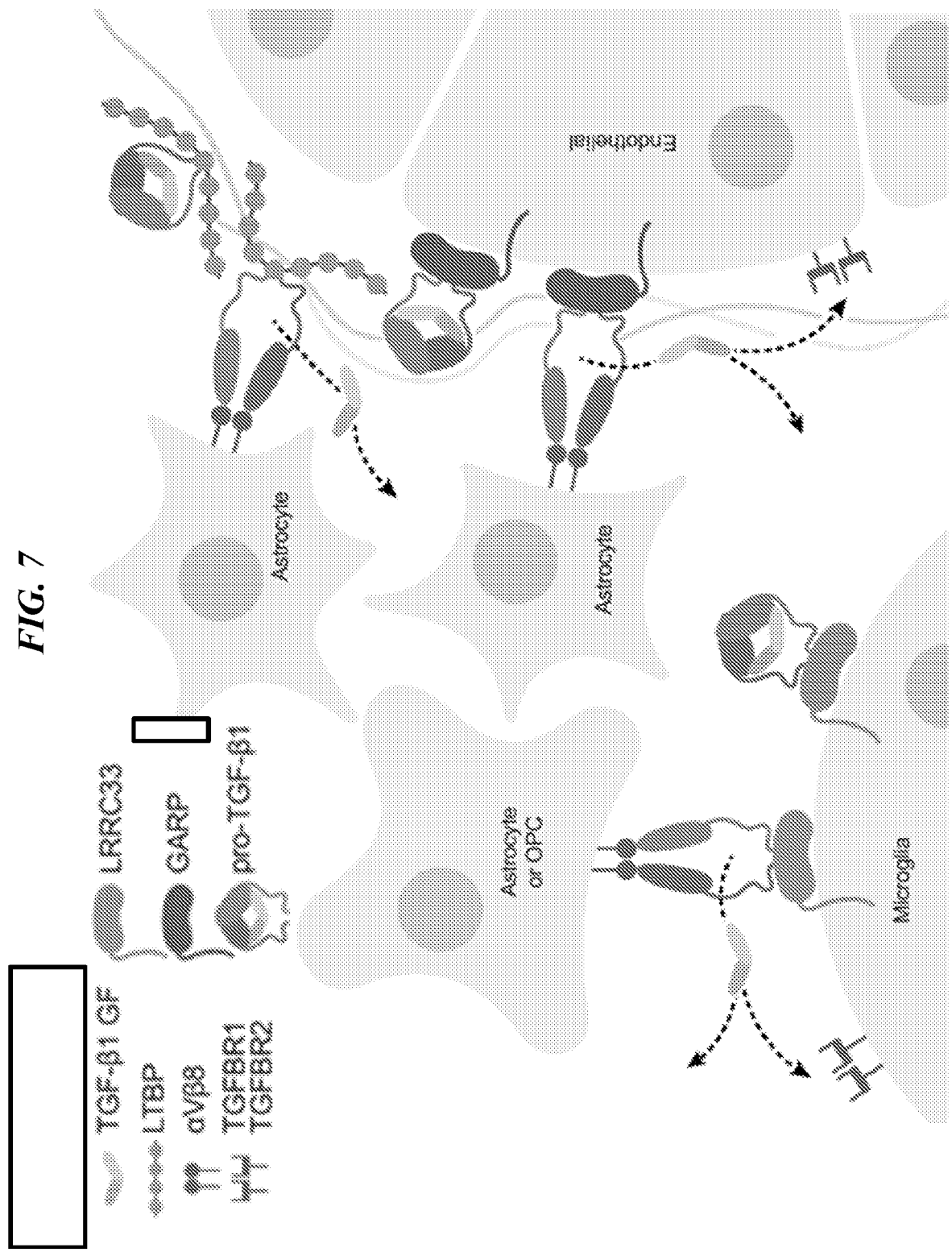
FIG. 7 shows a proposed model to illustrate LRRC33 interaction with proTGF-β1 and the comparison with GARP and LTBP in CNS.

Understanding of milieu-dependent TGF-β signaling in the CNS can only be achieved by combining functional data in which distinct steps of TGF-β signaling have been disrupted with transcriptomics data showing which cells actually express the TGF-β-related genes. Integration of these data allow for the formulation of a model for milieu-dependent TGF-β1 signaling in the CNS (FIG. 7). Transcriptional profiling of CNS cell populations shows that TGF-β1 and LRRC33 are both most highly expressed within microglia. Thus, microglia are not only the richest source of TGF-β1, but TGF-β1 in these cells appears to exclusively associate with LRRC33, because microglia do not express significant levels of GARP or LTBPs. These results are consistent with the essentially identical neurological phenotypes of Il2-Tgfb1;Tgfb1$^{-/-}$ and Lrrc33$^{-/-}$ mice and the transcriptional profiles of their microglia. Among genes encoding TGF-β-activating integrins, none of the profiled cells express the Itgb6 gene for the integrin β6 subunit, whereas Itgb8 and Itgav encoding integrin $\alpha_v\beta_8$ are well expressed on oligodendrocyte precursor cells, newly formed oligodendrocytes, and astrocytes, in lesser amounts on myelinating oligodendrocytes and neurons, but not on microglia (FIG. 7). Integrin $\alpha_v\beta_8$ is far more abundantly expressed in the brain than any other organ (Moyle et al., 1991), and in the brain localizes to the tips of neuronal dendritic spine and glial cell processes (Nishimura et al., 1998). Thus, the model presented herein predicts that these $\alpha_v\beta_8$-bearing cells release active TGF-β1 into the milieu of their cellular interfaces with TGF-β1-LRRC33-bearing microglia. (FIG. 7) Once activated, TGF-β1 can bind to its receptors on either the microglia (autocrine effect) or that of other glial cells or neurons (paracrine effect). This model indicates that disruption of microglia TGF-β1 secretion through Lrrc33 deletion has the potential to directly affect both microglia and neighboring cells and is consistent with loss of myelin and axons in Lrrc33$^{-/-}$ mice.

A role for activation by integrin $\alpha_v\beta_8$ of TGF-β1-LRRC33 complexes on microglia is supported by similarities in the phenotypes of mice deficient in Itgav, Itgb8, and Lrrc33. Mice deficient in Itgb8 or conditionally deficient in Itgav show defects in neurological function. Itgb8 mice in one genetic background developed hind limb weakness at 7-10 weeks and then lost mobility (Aluwihare et al., 2009). On another background, Itgb8$^{-/-}$ mice developed neurological phenotypes including paresis and ataxia that progressed until death by 5 months (Mobley et al., 2009). Mice conditionally deficient in Itgav in neural cells (glia and neurons but not microglia) similarly developed defects in hind limb coordination by 2-3 months. Symptoms progressed as shown by more severe paraparesis and urinary dysfunction, as documented in Lrrc33$^{-/-}$ mice. Moreover, Itgav-deficient mice showed both glial and axonal degeneration in the spinal cord (McCarty et al., 2005). The results on Itgav, Itgb8, Lrrc33, and Tgfb1-deficient mice together with the transcriptional profiles of CNS cell types provide strong support for the model that interactions in the milieu between integrin $\alpha_v\beta_8$-bearing neural cells and TGF-β1-LRRC33-microglia are required for maintenance of the neural integrity of myelinated axons (FIG. 7).

CNS vascular defects in mice mutant for Itgav and Itgb8 indicate an additional, Lrrc33$^-$ independent milieu for TGF-β activation in vascular development. Itgav$^{-/-}$ and Itgb8$^{-/-}$ mice show brain-specific hemorrhage and vascular abnormalities at birth (Aluwihare et al., 2009; McCarty et al., 2005; Mobley et al., 2009). Conditional Itgav$^{-/-}$ mutations show that the $\alpha_v$ integrin requirement is in neural cells (which include neurons, astrocytes, and oligodendrocytes but not microglia) but not in endothelial cells. Astrocytes and pericytes underly endothelium and are important in brain blood barrier formation. Among these cells, only astrocytes both express the subunits for integrin $\alpha_v\beta_8$ and are genetically implicated in Itgav-dependent vasculogenesis. Furthermore, astrocytes, pericytes, and endothelium express all three TGF-β isoforms together with LTBP1 and LTBP3, while pericytes and endothelium additionally express GARP. While integrin $\alpha_v\beta_8$ is important in both the astrocyte-pericyte-endothelium milieu for TGF-β activation, only LRRC33 is important in the microglia-neural cell milieu. Both microglia and blood capillaries are widely distributed throughout the brain and are typically within a few cell diameters of one another. Nonetheless, the severe effects of Lrrc33 deficiency on microglia and neurologic function indicate that these cell types are in a distinct milieu for TGF-β activation than vascular cells. Thus, findings presented herein related to the previously uncharacterized TGF-β milieu molecule support the model that TGF-β activation is highly localized in vivo. Furthermore, the association of milieu molecules with different in vivo functions of TGF-β opens up new approaches for therapy with antibodies or other antagonists that target TGF-β associated with specific milieu molecules.

References for Example 1 and 2

Abe, M., Harpel, J. G., Metz, C. N., Nunes, I., Loskutoff, D. J., and Rifkin, D. B. (1994). An assay for transforming growth factor-beta using cells transfected with a plasminogen activator inhibitor-1 promoter-luciferase construct. Anal Biochem 216, 276-284.

Aluwihare, P., Mu, Z., Zhao, Z., Yu, D., Weinreb, P. H., Horan, G. S., Violette, S. M., and Munger, J. S. (2009). Mice that lack activity of αVβ6- and αVβ8-integrins reproduce the abnormalities of TGFβ1- and TGFβ3-null mice. J Cell Sci 122, 227-232.

Bialas, A. R., and Stevens, B. (2013). TGF-beta signaling regulates neuronal C1q expression and developmental synaptic refinement. Nat Neurosci 16, 1773-1782.

Brionne, T. C., Tesseur, I., Masliah, E., and Wyss-Coray, T. (2003). Loss of TGF-β1 leads to increased neuronal cell death and microgliosis in mouse brain. Neuron 40, 1133-1145.

Brunner, A. M., Marquardt, H., Malacko, A. R., Lioubin, M. N., and Purchio, A. F. (1989). Site-directed mutagenesis of cysteine residues in the pro region of the transforming growth factor beta 1 precursor. Expression and characterization of mutant proteins. J Biol Chem 264, 13660-13664.

Butovsky, O., Jedrychowski, M. P., Moore, C. S., Cialic, R., Lanser, A. J., Gabriely, G., Koeglsperger, T., Dake, B., Wu, P. M., Doykan, C. E., et al. (2014). Identification of a unique TGF-β-dependent molecular and functional signature in microglia. Nat Neurosci 17, 131-143.

Carvalho, B. S., and Irizarry, R. A. (2010). A framework for oligonucleotide microarray preprocessing. Bioinformatics 26, 2363-2367.

Constam, D. B., Philipp, J., Malipiero, U. V., ten Dijke, P., Schachner, M., and Fontana, A. (1992). Differential expression of transforming growth factor-beta 1, -beta 2, and -beta 3 by glioblastoma cells, astrocytes, and microglia. J Immunol 148, 1404-1410.

Dolan, J., Walshe, K., Alsbury, S., Hokamp, K., O'Keeffe, S., Okafuji, T., Miller, S. F., Tear, G., and Mitchell, K. J. (2007). The extracellular leucine-rich repeat superfamily; a comparative survey and analysis of evolutionary relationships and expression patterns. BCM Genomics 8, 320.

Flavell, R. A., Sanjabi, S., Wrzesinski, S. H., and Licona-Limón, P. (2010). The polarization of immune cells in the tumour environment by TGFβ. Nat Rev Immunol 10, 554-567.

Irizarry, R. A., Hobbs, B., Collin, F., Beazer-Barclay, Y. D., Antonellis, K. J., Scherf, U., and Speed, T. P. (2003). Exploration, normalization, and summaries of high density oligonucleotide array probe level data. Biostatistics 4, 249-264.

Jin, M. S., and Lee, J.-o. (2008). Application of hybrid LRR technique to protein crystallization. BMB Rep 41, 353-357.

Katoh, K. S., D M. (2013). MAFFT multiple sequence alignment software version 7: improvements in performance and usability. Mol Biol Evol 30, 772-780.

Kiefer, R., Streit, W. J., Toyka, K. V., Kreutzberg, G. W., and Hartung, H. P. (1995). Transforming growth factor-01: a lesion-associated cytokine of the nervous system. Int J Dev Neurosci 13, 331-339.

Koeglsperger, T., Li, S., Brenneis, C., Saulnier, J. L., Mayo, L., Carrier, Y., Selkoe, D. J., and Weiner, H. L. (2013). Impaired glutamate recycling and GluN2B-mediated neuronal calcium overload in mice lacking TGF-β1 in the CNS. Glia 61, 985-1002.

Krieglstein, K., Rufer, M., Suter-Crazzolara, C., and Unsicker, K. (1995). Neural functions of the transforming growth factors β. Int J Dev Neurosci 13, 301-315.

Kulkarni, a. B., Huh, C. G., Becker, D., Geiser, a., Lyght, M., Flanders, K. C., Roberts, a. B., Sporn, M. B., Ward, J. M., and Karlsson, S. (1993). Transforming growth factor beta 1 null mutation in mice causes excessive inflammatory response and early death. Proc Natl Acad Sci USA 90, 770-774.

Lehrmann, E., Kiefer, R., Christensen, T., Toyka, K. V., Zimmer, J., Diemer, N. H., Hartung, H. P., and Finsen, B. (1998). Microglia and macrophages are major sources of locally produced transforming growth factor-beta1 after transient middle cerebral artery occlusion in rats. Glia 24, 437-448.

Liu, J., Zhang, Z., Chai, L., Che, Y., Min, S., and Yang, R. (2013). Identification and characterization of a unique leucine-rich repeat protein (LRRC33) that inhibits Toll-like receptor-mediated N F-K B activation. Biochem Biophys Res Commun 434, 28-34.

Liu, Z., Chen, H., Huang, Y., Qiu, Y., and Peng, Y. (2016). Transforming growth factor-01 acts via TβR-I on microglia to protect against MPP(+)-induced dopaminergic neuronal loss. Brain Behav Immun 51, 131-143.

Ludbrook, S. B., Barry, S. T., Delves, C. J., and Horgan, C. M. (2003). The integrin avb3 is a receptor for the latency-associated peptides of transforming growth factors b1 and b3. Biochem J 369, 311-318.

McCarty, J. H., Lacy-Hulbert, A., Charest, A., Bronson, R. T., Crowley, D., Housman, D., Savill, J., Roes, J., and Hynes, R. O. (2005). Selective ablation of αv integrins in the central nervous system leads to cerebral hemorrhage, seizures, axonal degeneration and premature death. Development 132, 165-176.

Mobley, A. K., Tchaicha, J. H., Shin, J., Hossain, M. G., and McCarty, J. H. (2009). Beta8 integrin regulates neurogenesis and neurovascular homeostasis in the adult brain. J Cell Sci 122, 1842-1851.

Morikawa, M., Derynck, R., and Miyazono, K. (2016). TGF-β and the TGF-β Family: Context-Dependent Roles in Cell and Tissue Physiology. Cold Spring Harb Perspect Biol 8.

Moyle, M., Napier, M. A., and McLean, J. W. (1991). Cloning and expression of a divergent integrin subunit $b_8$. J Biol Chem 266, 19650-19658.

Munger, J. S., Huang, X., Kawakatsu, H., Griffiths, M. J. D., Dalton, S. L., Wu, J., Pittet, J.-F., Kaminski, N., Garat, C., Matthay, M. A., et al. (1999). The integrin αvβ6 binds and activates latent TGFβ1: A mechanism for regulating pulmonary inflammation and fibrosis. Cell 96, 319-328.

Nishimura, S. L., Boylen, K. P., Einheber, S., Milner, T. a., Ramos, D. M., and Pytela, R. (1998). Synaptic and glial localization of the integrin αvβ8 in mouse and rat brain. Brain Res 791, 271-282.

Noubade, R., Wong, K., Ota, N., Rutz, S., Eidenschenk, C., Valdez, P. a., Ding, J., Peng, I., Sebrell, A., Caplazi, P., et al. (2014). NRROS negatively regulates reactive oxygen species during host defence and autoimmunity. Nature 509, 235-239.

Qian, L., Wei, S., Zhang, D., Hu, X., Xu, Z., Wilson, B., El-Benna, J., Hong, J., and Flood, P. (2008). Potent anti-inflammatory and neuroprotective effects of TGF-beta1 are mediated through the inhibition of ERK and p47phox-Ser345 phosphorylation and translocation in microglia. J Immunol 181, 660-668.

Robertson, I. B., and Rifkin, D. B. (2016). Regulation of the Bioavailability of TGF-β and TGF-β-Related Proteins. Cold Spring Harb Perspect Biol 8.

Smyth, G. K., Michaud, J., and Scott, H. S. (2005). Use of within-array replicate spots for assessing differential expression in microarray experiments. Bioinformatics 21, 2067-2075.

Stockis, J., Colau, D., Coulie, P. G., and Lucas, S. (2009). Membrane protein GARP is a receptor for latent TGF-β on the surface of activated human Treg. Eur J Immunol 39, 3315-3322.

Su, X., Mei, S., Liang, X., Wang, S., Liu, J., Zhang, Y., Bao, Y., Chen, Y., Che, Y., Chunhua Zhao, R., et al. (2014). Epigenetically modulated LRRC33 acts as a negative physiological regulator for multiple Toll-like receptors. J Leukoc Biol 95, 1-10.

Subramanian, A. T., P; Mootha, V K; Mukherjee, S; Ebert, B L; Gillette, M A; Paulovich, A; Pomeroy, S L; Golub, T R; Lander, E S; Mesirov, J P. (2005). Gene set enrichment analysis: a knowledge-based approach for interpreting genome-wide expression profiles. Proc Natl Acad Sci USA 102, 15545-15550.

Taipale, J. M., S; Hurme, M; Keski-Oja, J. (1994). Induction of transforming growth factor β1 and its receptor expression during myeloid leukemia cell differentiation. Cell Growth Differ 5, 1309-1319.

Tran, D. Q., Andersson, J., Wang, R., Ramsey, H., Unutmaz, D., and Shevach, E. M. (2009). GARP (LRRC32) is essential for the surface expression of latent TGF-β on platelets and activated FOXP3+ regulatory T cells. Proc Natl Acad Sci USA 106, 13445-13450.

Tsunawaki, S., Sporn, m., Ding, a., and Nathan, C. (1988). Deactivation of macrophages by transforming growth factor-β. Nature 334, 260-264.

Wang, R., Kozhaya, L., Mercer, F., Khaitan, A., Fujii, H., and Unutmaz, D. (2009). Expression of GARP selectively identifies activated human FOXP3+ regulatory T cells. Proc Natl Acad Sci USA 106, 13439-13444.

Wang, R., Zhu, J., Dong, X., Shi, M., Lu, C., and Springer, T. A. (2012). GARP regulates the bioavailability and activation of TGFβ. Mol Biol Cell 23, 1129-1139.

Wipff, P. J., Rifkin, D. B., Meister, J. J., and Hinz, B. (2007). Myofibroblast contraction activates latent TGF-β1 from the extracellular matrix. J Cell Biol 179, 1311-1323.

Wirenfeldt, M., Babcock, A. A., and Vinters, H. V. (2011). Microglia—insights into immune system structure, function, and reactivity in the central nervous system. Histol Histopathol 26, 519-530.

Zhang, Y. C., K; Sloan, S A; Bennett, M L; Scholze, A R; O'Keeffe, S; Phatnani, H P; Guarnieri, P; Caneda, C; Ruderisch, N; Deng, S; Liddelow, S A; Zhang, C; Daneman, R; Maniatis, T; Barres, B A; Wu, J. (2014). An RNA-sequencing transcriptome and splicing database of glia, neurons, and vascular cells of the cerebral cortex. J Neurosci 34, 11929-11947.

Example 3

Introduction

Although T-cells have dominated the focus of immuno-oncology, harnessing both the innate and adaptive arms of the immune system will produce superior tumor reduction and elimination. Myeloid cells play an important role in tumor progression by affecting the tumor microenvironment [1-5]. Among myeloid cells, tumor associated macrophages (TAMs) have been found to substantially infiltrate the tumor microenvironment in tumor-bearing mice as well as cancers patients, and can make up 50% of the mass of most solid tumors [6-8]. Clinically, a high tumor density of TAMs has been associated with resistance to chemotherapy and a significantly worse clinical outcome for cancer patients. Importantly, "M2" polarized TAMs exhibit increased production of transforming growth factor beta (TGF-β), which has been found to be necessary for downregulating tumor immune-surveillance in vivo and thus provides an important immune-evading mechanism used by tumors [9].

A leucine-rich repeat-containing protein 33 (LRRC33), whose expression is largely restricted to myeloid lineages, was identified as a novel protein that disulfide links to the latent form of TGF-β1 and presents it on the surface of macrophages for activation. Without wishing to be bound by a particular theory, it was reasoned that given its restricted expression on myeloid cells, LRRC33 is specifically involved in TGF-β1 activation on the cell surface of TAMs and plays a role in regulating immune responses in the tumor microenvironment. Described herein is experimental data showing that LRRC33 is an important immune-oncology target for specifically inhibiting TGF-β1's pro-tumorigenic role in the tumor microenvironment.

TGF-β is a multifunctional cytokine that regulates many cellular and organismal processes, including immunity and tumorigenesis. TGF-β is overexpressed in both human and murine tumors, suppresses antitumor immunity, and is correlated with poor prognosis for cancer patients [10-14]. Paradoxically, TGF-β functions as both a tumor suppressor and a tumor promoter. The multifunctional roles of TGF-β are highly context-dependent and influenced by cell type, culture conditions, interaction with other signaling pathways, developmental or disease stage in vivo, and innate genetic variation among individuals. This makes the pathway a particular challenge for drug development since TGF-β-targeted therapeutics can yield adverse side effects unrelated to cancer, such as widespread inflammation, autoimmunity, or cardiovascular defect. As described herein, LRRC33 provides a mechanism for macrophage-specific or tumor microenvironment-specific therapeutic targeting of TGF-β and inhibition of its pro-tumorigenic role. Given its restricted expression pattern, LRRC33-based treatments target TAMs, and therefore are combined with other therapies, including anti-PD-1 (which targets T cells), currently in clinical trials to enhance efficacy.

Loss of LRRC33 Function Confers Increased Resistance to Tumor Growth.

Macrophages can be classified as classically activated (M1) or alternatively activated (M2) that exhibit distinct phenotypes and functions. The M1 phenotype exhibits higher inflammatory activity and is anti-tumorigenic. In contrast, the M2 phenotype generally dampens immune activity that can be pro-tumorigenic. TAMs exhibit a pro-tumor, polarized M2 phenotype and characterized with increased TGF-β production that contributes to the ability of tumors to evade the immune system. The M2 phenotype in monocyte-derived macrophages is correlated with increased LRRC33 expression, whereas the M1 phenotype in LPS/IFN-γ/TNF-α-stimulated macrophages is correlated with decreased LRRC33[15]. Moreover, Lac33$^{-/-}$ mice showed increased reactive oxygen species, inflammatory cytokines production from macrophages (a hallmark of the M1 phenotype), and enhanced bacterial killing ability, which may be downstream of defective TGF-β signaling[15-18]. These rationales, indicate that the tumor-challenged Lrrc33' mice, without TGF-β activation on macrophages, is associated with a decrease in TAM cell population or a change in the phenotype of TAMs from M2 to M1, decreased TGF-β signaling and thus show more tumor-resistant phenotype.

Figures 11A, 11B, 11C, 11D, 11E:
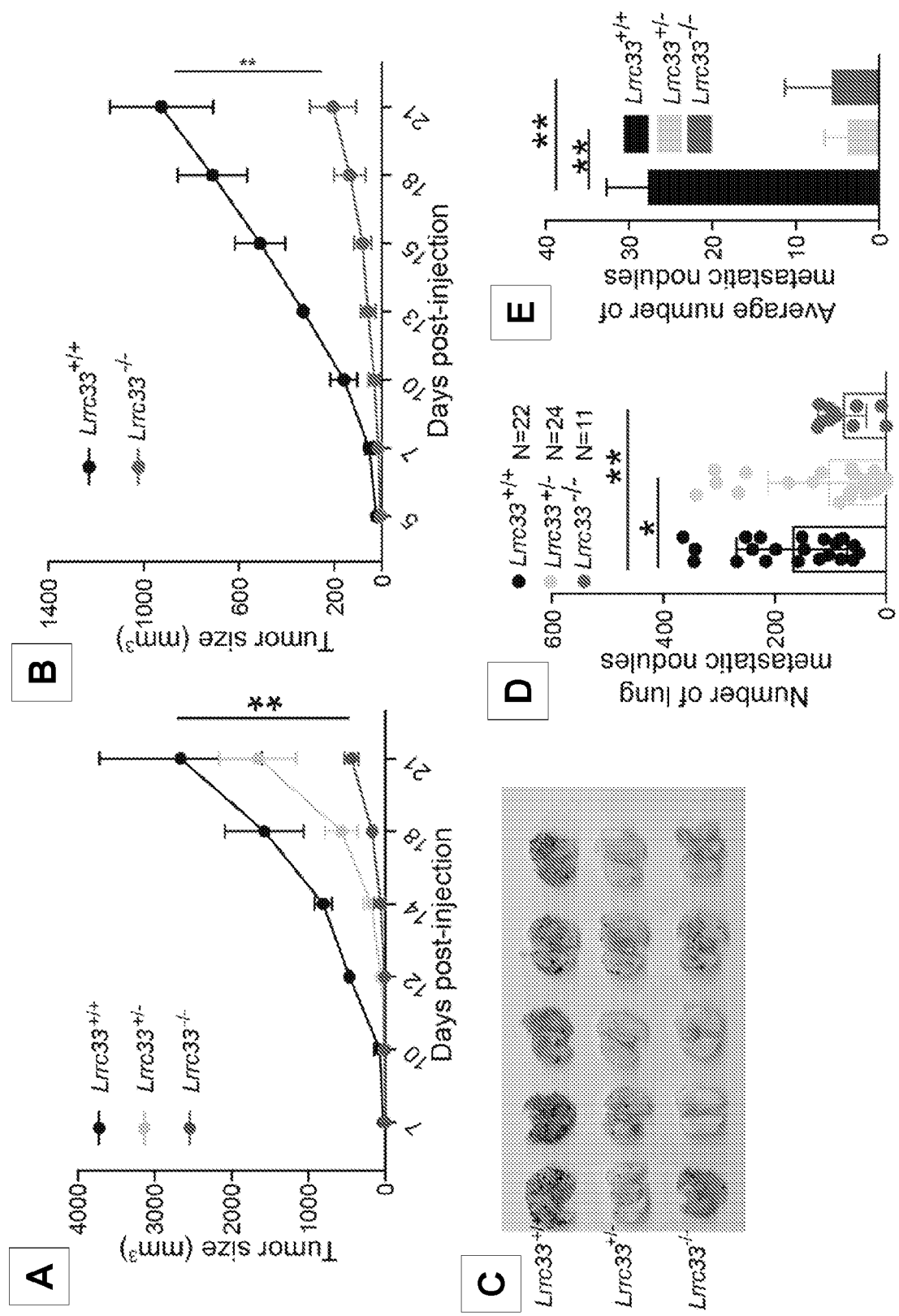
FIGS. 11A-11F show that Lrrc33-deficient mice exhibit decreased tumor growth and metastasis. (A) $1\times10^5$ B16.F10 cells were subcutaneously injected into 3 groups of mice, and melanoma tumor sizes were measured after the indicated times. Data is presented as mean+SEM; N=6 tumors for each group. T test, p<0.01. (B) $5\times10^5$ MC38 cells were subcutaneously injected into 2 groups of mice and tumor sizes were measured after the indicated times. Data are presented is mean+SEM; N=6 tumors for each group. p<0.01. (C, D) B16.F10 ($3\times10^5$) cells were intravenously injected into 3 groups of mice, and metastasis was observed after 13 days post-injection. The appearance of the lungs after perfusion indicating gross numbers of tumors on lungs (C) and the tumor nodules on the lungs were counted (D). (E, F) Lungs were removed and H&E staining was performed to identify metastatic lesions (F) The average number of lesions per 6 whole-lung sections is shown (E) Data is presented as mean+SEM; the mouse amount for each group is indicated. **p<0.01, *p<0.05.
Figure 11F:
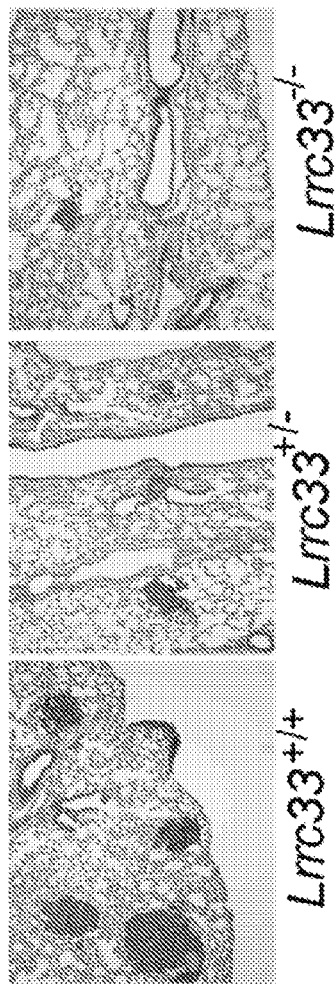

Data present herein show that Lrrc33$^{-/-}$ mice exhibited smaller tumor size than Lac33$^{+/+}$ mice as early as 12 and 10 days post-injection with B16.F10 and MC38 cells, respectively (FIGS. 11A and 11B). This reduced tumor size persisted throughout the course of the experiment such that by day 21, tumor size in B16.F10 and MC38-injected Lac33$^{-/-}$ mice were 6.5 and 4.3 folds smaller, respectively, than in Lrrc33$^{+/+}$ mice (FIGS. 11A and 11B). Lac33$^{+/-}$ heterozygotes also showed resistance to tumor growth after B16.F10 injection, albeit weaker than Lac33$^{-/-}$ homozygotes (~3 folds smaller tumor than WT on day 21, FIG. 11A).

Methods and Materials

Two different syngeneic tumor models were utilized herein: melanoma and colon carcinoma. The syngeneic tumor models were established by subcutaneous inoculation with murine melanoma cell line (B16.F10), and colon carcinoma cell line (MC38) as previously described[19, 20-22]. Briefly, subcutaneously implanted B16.F10 (1×10$^5$), MC38 (5×10$^5$) cells into the backs of syngeneic C57BL6/NJ Lrrc33$^{+/+}$, Lac33$^{+/-}$, and Lac33$^{-/-}$ mice at 8 weeks old (N=6 mice per genotype per tumor model). Tumor size was measured blind (length×width2×0.5) on indicated days (FIGS. 11A and 11B).

Loss of LRRC33 Function Confers Increased Resistance to Metastasis.

Loss of Lrrc33 exhibited dose-dependent resistance against B16.F10 lung metastasis. Lac33$^{+/-}$ and Lrrc33$^{-/-}$ mice displayed 37% and 56% fewer pulmonary metastatic modules on the lung surface than wildtype after B16.F10 challenge (FIG. 11D). Meanwhile, quantification of metastases using H&E staining revealed a more substantial decrease of 89% and 82% in Lac3$^{+/-}$ and Lac33$^{-/-}$ mice, respectively, compared to wildtype (FIGS. 11E and F).

B16.F10 (3×10$^5$) cells were intravenously injected into Lac33' (N=24 per model), Lac33$^{+/-}$ (N=24 per model), and Lrrc33$^{-/-}$ (N=12 per model) mice and allowed 13 days of inoculation, which is sufficient for lung metastasis [19]. Mice were then sacrificed and their lungs were harvested to compare the extent of lung metastasis. In B16.F10-challenged mice, pigmented melanomas were visible on the lung surface allowing for the detection of metastatic foci number (pulmonary nodules) (FIG. 11C). Melanoma metastasis was additionally assessed using haemotoxylin and eosin (H&E) staining of lung tissue sections.

Therapeutic Efficiency of Targeting LRRC33/Pro-TGF-β1 Complex in Combination with Checkpoint Antibody to Treat Cancers.

Only a small proportion of cancer patients respond to anti-PD-1 agent, and multiple mechanisms of immune resistance exist in tumors. Among the key mechanisms, myeloid cells have a major role in limiting effective tumor immunity [23]. Experimental data described herein the examples show that combination agent with LRRC33 function blocking therapeutics (e.g. antibodies) that target myeloid cells will improve anti-PD-1 efficacy. LRRC33 deficiency improves the effectiveness of anti-PD-1 agent in a B16.F10 melanoma tumor model, which has been shown to be resistant to anti-PD-1 treatment [23, 26].

Figure 12:
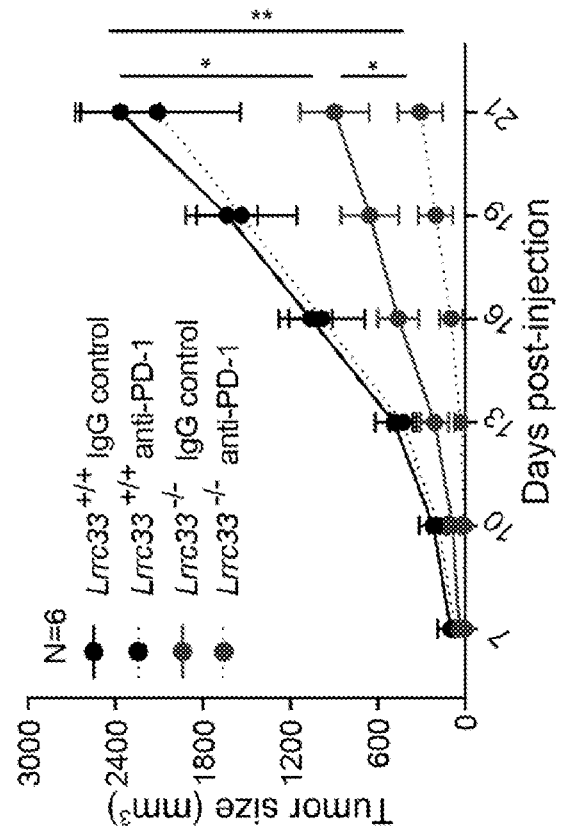
FIG. 12 shows that LRRC33 deficiency and PD-1 blockade synergistically inhibit tumor growth in a B16.F10 melanoma model. Mice were subcutaneously injected with B16.F10 cells and tumor sizes were measured and plotted as average total tumor burden. For PD-1 checkpoint blockade, mice were randomly placed into two groups and then intraperitoneally injected with 250 ug of anti-PD-1 or IgG control antibody on day 4, 7, 10, 13, 16. T test, *p<0.05, **p<0.01. Error bars represent s.e.m.

There was no significant difference in tumor size between IgG control-treated and anti-PD-1-treated Lac33$^{+/+}$ mice, indicating that melanoma of Lac33$^{+/+}$ mice are highly resistant to anti-PD-1 treatment (FIG. 12). In contrast, Lac33$^{-/-}$ mice displayed a much smaller tumor size, confirming the previous experimental observation presented in FIG. 11A. Anti-PD-1-treated Lac33$^{-/-}$ mice exhibited a significantly smaller tumor size than IgG control-treated Lac33$^{-/-}$ mic, indicating that the resistance of the B16.F10 tumor to anti-PD-1 agent is overcome when combined with the loss of LRRC33 (FIG. 12). The reduced tumor size was evident by day 10 and persisted throughout the course of the experiment. At day 21, tumor size in anti-PD-1-treated Lrrc33$^{-/-}$ mice was ~4.5 fold smaller than in IgG control-treated Lrrc33$^{-/-}$ mice. It is contemplated that the combination therapy of Lrcc33 inhibition and anti-PD-1 treatment will be effective in treating MC38 colon carcinoma, due to the observed sensitivity of MC38 colon carcinoma to anti-PD-1 treatment [28].

Methods and Materials

B16.F10 cells are subcutaneously implanted separately into Lac33$^{+/+}$ (N=12) and Lrrc33$^{-/-}$ mice (N=12) and tumor sizes are measured. For PD-1 checkpoint blockade, mice are randomly divided into two groups (N=6 per group) after 4 days inoculation and then intraperitoneally injected with 250 ug of anti-PD-1 (BioXCell clone RMP1-14; cat. BE0146) or IgG control (BioXCell Rat IgG2a) on day 4, 7, 10, 13, 16. All animal experiments presented herein in Example 3 were approved by the Institutional Animal Care and Use Committees (IACUC) at Harvard Medical School (protocol #IS00000227) and Children's Hospital (protocol #15-01-2859R). The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

References for Example 3

1. Yang, L., et al., *Abrogation of TGF beta signaling in mammary carcinomas recruits Gr-1+CD11b+ myeloid cells that promote metastasis*. Cancer Cell, 2008. 13(1): p. 23-35.
2. Pollard, J. W., *Trophic macrophages in development and disease*. Nat Rev Immunol, 2009. 9(4): p. 259-70.
3. Mantovani, A., *Cancer: Inflaming metastasis*. Nature, 2009. 457(7225): p. 36-7.
4. Yang, L., et al., *Expansion of myeloid immune suppressor Gr+CD11b+ cells in tumor-bearing host directly promotes tumor angiogenesis*. Cancer Cell, 2004. 6(4): p. 409-21.
5. Marvel, D. and D. I. Gabrilovich, *Myeloid-derived suppressor cells in the tumor microenvironment: expect the unexpected*. J Clin Invest, 2015. 125(9): p. 3356-64.
6. Guo, Q., et al., *New Mechanisms of Tumor Associated Macrophages on Promoting Tumor Progression: Recent Research Advances and Potential Targets for Tumor Immunotherapy*. J Immunol Res, 2016. 2016: p. 9720912.
7. Morrison, C., *Immuno-oncologists eye up macrophage targets*. Nat Rev Drug Discov, 2016. 15(6): p. 373-4.
8. Yang, L. and Y. Zhang, *Tumor-associated macrophages: from basic research to clinical application*. J Hematol Oncol, 2017. 10(1): p. 58.
9. Gabrilovich, D. I., S. Ostrand-Rosenberg, and V. Bronte, *Coordinated regulation of myeloid cells by tumours*. Nat Rev Immunol, 2012. 12(4): p. 253-68.
10. Wikstrom, P., et al., *Transforming growth factor beta1 is associated with angiogenesis, metastasis, and poor clinical outcome in prostate cancer*. Prostate, 1998. 37(1): p. 19-29.
11. Hasegawa, Y., et al., *Transforming growth factor-beta1 level correlates with angiogenesis, tumor progression, and prognosis in patients with nonsmall cell lung carcinoma*. Cancer, 2001. 91(5): p. 964-71.

12. Lee, J. C., et al., *Elevated TGF-beta1 secretion and down-modulation of NKG2D underlies impaired NK cytotoxicity in cancer patients*. J Immunol, 2004. 172(12): p. 7335-40.
13. Castriconi, R., et al., *Transforming growth factor beta 1 inhibits expression of NKp30 and NKG2D receptors: consequences for the NK-mediated killing of dendritic cells*. Proc Natl Acad Sci USA, 2003. 100(7): p. 4120-5.
14. Thomas, D. A. and J. Massague, *TGF-beta directly targets cytotoxic T cell functions during tumor evasion of immune surveillance*. Cancer Cell, 2005. 8(5): p. 369-80.
15. Noubade, R., et al., *NRROS negatively regulates reactive oxygen species during host defence and autoimmunity*. Nature, 2014. 509(7499): p. 235-9.
16. Flavell, R. A., et al., *The polarization of immune cells in the tumour environment by TGFbeta*. Nat Rev Immunol, 2010. 10(8): p. 554-67.
17. Tsunawaki, S., et al., *Deactivation of macrophages by transforming growth factor-beta*. Nature, 1988. 334 (6179): p. 260-2.
18. Su, X., et al., *Epigenetically modulated LRRC33 acts as a negative physiological regulator for multiple Toll-like receptors*. J Leukoc Biol, 2014. 96(1): p. 17-26.
19. Overwijk, W. W. and N. P. Restifo, *B16 as a mouse model for human melanoma*. Curr Protoc Immunol, 2001. Chapter 20: p. Unit 20 1.
20. Wang, D., et al., *An enhanced immune response of Mclk1(+)/(−) mutant mice is associated with partial protection from fibrosis, cancer and the development of biomarkers of aging*. PLoS One, 2012. 7(11): p. e49606.
21. Kellar, A., C. Egan, and D. Morris, *Preclinical Murine Models for Lung Cancer: Clinical Trial Applications*. Biomed Res Int, 2015. 2015: p. 621324.
22. Kodumudi, K. N., et al., *Immune Checkpoint Blockade to Improve Tumor Infiltrating Lymphocytes for Adoptive Cell Therapy*. PLoS One, 2016. 11(4): p. e0153053.
23. De Henau, O., et al., *Overcoming resistance to checkpoint blockade therapy by targeting PI3Kgamma in myeloid cells*. Nature, 2016. 539(7629): p. 443-447.
24. Cuende, J., et al., *Monoclonal antibodies against GARP/TGF-beta1 complexes inhibit the immunosuppressive activity of human regulatory T cells in vivo*. Sci Transl Med, 2015. 7(284): p. 284ra56.
25. Gabriely, G., et al., *Targeting latency-associated peptide promotes antitumor immunity*. Sci Immunol, 2017. 2(11).
26. Mosely, S. I., et al., *Rational Selection of Syngeneic Preclinical Tumor Models for Immunotherapeutic Drug Discovery*. Cancer Immunol Res, 2017. 5(1): p. 29-41.
27. Chen, S., et al., *Combination of 4-1BB agonist and PD-1 antagonist promotes antitumor effector/memory CD8 T cells in a poorly immunogenic tumor model*. Cancer Immunol Res, 2015. 3(2): p. 149-60.
28. Juneja, V. R., et al., *PD-L1 on tumor cells is sufficient for immune evasion in immunogenic tumors and inhibits CD8 T cell cytotoxicity*. J Exp Med, 2017. 214(4): p. 895-904.

What is claimed is:

1. A composition comprising an agent that stabilizes Leucine-Rich Repeat-Containing 33 (LRRC33)-Transforming Growth Factor β (TGF-β) prodomain-TGF-β complex, wherein the agent is an antibody or antigen-binding fragment comprising the variable heavy chain sequence of SEQ ID NO: 2 and the variable light chain sequence of SEQ ID NO: 3, or a full set of 6 CDRs derived therefrom.

2. The composition of claim 1, wherein the antibody or antigen-binding fragment specifically binds to an LRRC33 polypeptide.

3. The composition of claim 2, wherein the LRRC33 polypeptide has the amino acid sequence of SEQ ID NO: 1.

4. The composition of claim 1, further comprising a checkpoint inhibitor.

5. The composition of claim 4, wherein the checkpoint inhibitor is selected from the group consisting of: an anti-programmed cell death 1 (PD-1) agent, an anti-programmed cell death-ligand 1 (PDL-1) agent, an anti-cytotoxic T-lymphocyte-associated protein 4 (CTLA4) agent, an anti-lymphocyte-activation gene 3 (LAG3) agent, and an anti-T cell immunoglobulin and mucin domain-3 (TIM3) agent.

6. The composition of claim 5, wherein the anti-PD-1 agent is anti-PD-1 antibody clone RMP1-14.

7. The composition of claim 1, further comprising an adjuvant.

8. A method of preventing release of active TGF-β from an LRRC33-TGF-β prodomain-TGF-β complex, the method comprising contacting a cell that comprises an LRRC33-TGF-β prodomain-TGF-β complex, with an agent that stabilizes the LRRC33-TGF-β prodomain-TGF-β complex, wherein the stabilizing prevents release of active TGF-β from the LRRC33-TGF-β prodomain-TGF-β complex,
wherein the agent is an antibody or antigen-binding fragment comprising the variable heavy chain sequence of SEQ ID NO: 2 and the variable light chain sequence of SEQ ID NO: 3, or a full set of 6 CDRs derived therefrom.

9. The method of claim 8, wherein the antibody or antigen-binding fragment specifically binds to an LRRC33 polypeptide.

10. The method of claim 8, wherein the LRRC33 polypeptide has the amino acid sequence of SEQ ID NO: 1.

* * * * *